(12) United States Patent
Skead et al.

(10) Patent No.: US 8,889,861 B2
(45) Date of Patent: Nov. 18, 2014

(54) CRYSTALLINE FORMS OF A PURINE DERIVATIVE

(75) Inventors: Benjamin Mark Skead, Cambridge (GB); Christopher Peter Worrall, Northwich (GB); Jonathan Charles Christian Atherton, Co Durham (GB); Julian Scott Northen, South Shields (GB); Philippe Fernades, Sunderland (GB)

(73) Assignee: Cyclacel Limited, London (GB)

( * ) Notice: Subject to any disclaimer, the term of this patent is extended or adjusted under 35 U.S.C. 154(b) by 0 days.

(21) Appl. No.: 13/574,488

(22) PCT Filed: Jan. 24, 2011

(86) PCT No.: PCT/GB2011/000087
§ 371 (c)(1),
(2), (4) Date: Nov. 15, 2012

(87) PCT Pub. No.: WO2011/089401
PCT Pub. Date: Jul. 28, 2011

(65) Prior Publication Data
US 2013/0072504 A1    Mar. 21, 2013

(30) Foreign Application Priority Data
Jan. 22, 2010  (GB) .................................. 1001075.9

(51) Int. Cl.
| | | |
|---|---|---|
| *C07D 473/00* | (2006.01) | |
| *C07C 59/265* | (2006.01) | |
| *C07D 473/16* | (2006.01) | |
| *G01P 5/07* | (2006.01) | |
| *C07C 65/05* | (2006.01) | |
| *G01F 1/115* | (2006.01) | |
| *C07C 309/04* | (2006.01) | |
| *C07C 59/255* | (2006.01) | |
| *C07C 51/41* | (2006.01) | |
| *C07C 309/29* | (2006.01) | |
| *C07C 59/245* | (2006.01) | |
| *C07C 303/32* | (2006.01) | |
| *C07C 57/145* | (2006.01) | |
| *G01P 3/48* | (2006.01) | |
| *C07C 57/15* | (2006.01) | |
| *A61K 31/52* | (2006.01) | |

(52) U.S. Cl.
CPC ............ *C07D 473/16* (2013.01); *C07C 59/265* (2013.01); *G01P 5/07* (2013.01); *C07C 65/05* (2013.01); *G01F 1/115* (2013.01); *C07C 309/04* (2013.01); *C07C 59/255* (2013.01); *C07C 51/412* (2013.01); *C07C 309/29* (2013.01); *C07C 59/245* (2013.01); *C07C 303/32* (2013.01); *C07C 57/145* (2013.01); *G01P 3/4802* (2013.01); *C07B 2200/13* (2013.01); *C07C 57/15* (2013.01); *A61K 31/52* (2013.01)
USPC ........................................................ 544/277

(58) Field of Classification Search
None
See application file for complete search history.

(56) References Cited

FOREIGN PATENT DOCUMENTS

| | | | | |
|---|---|---|---|---|
| GB | WO 2008122767 | A2 * | 10/2008 | ........... C07D 473/16 |
| WO | 03/002565 | A1 | 1/2003 | |
| WO | 2004/016612 | A2 | 2/2004 | |
| WO | 2004/016613 | A2 | 2/2004 | |
| WO | 2008/122767 | A2 | 10/2008 | |
| WO | WO 2008122767 | A2 * | 10/2008 | |

OTHER PUBLICATIONS

Norris, Experimental Organic Chemistry, 1924, McGraw-Hill Book Company, Inc., 2nd Edition, 1-4.*
Bastin et al., Organic Process Research & Development, 2000, 4, 427-435.*
Haynes et al. (Journal of Pharmaceutical Sciences, 2005, 94, 2111-2120).*
Morissette et al. in Drug Delivery Reviews, 56 (2004) 275-300.*
De Azevedo, Walter Filgueira et al., "Inhibition of cyclin-dependent kinases by purine analogues. Crystal structure of human cdk2 complexed with roscovitine," Eur. J. Biochem., vol. 243:518-526 (1997).
Haesslein, Jean-luc et al., "Recent Advances in Cyclin-Dependent Kinase Inhibition. Purine-Based Derivatives as Anti-Cancer Agents. Roles and Perspectives for the Future," Current Topics in Medicinal Chemistry, vol. 2:1037-1050 (2002).
International Preliminary Report on Patentability for Application No. PCT/GB2008/001173, 13 pages, dated Oct. 6, 2009.
International Preliminary Report on Patentability and Written Opinion for Application No. PCT/GB2011/000087, 7 pages, dated Jul. 24, 2012.

* cited by examiner

*Primary Examiner* — Dennis Heyer
*Assistant Examiner* — Daniel M Podgorski
(74) *Attorney, Agent, or Firm* — Nelson Mullins Riley & Scarborough LLP; Cynthia L. Kanik

(57) ABSTRACT

The present invention relates to new crystalline forms of a purine derivative which exhibits excellent anti-tumour activity. The invention also relates to a pharmaceutical composition containing said crystalline forms as an active ingredient, and use thereof in the prevention or treatment of disease. The invention further relates to a process for preparing the crystalline forms.

4 Claims, 20 Drawing Sheets

CRYSTALLINE FORMS OF A PURINE DERIVATIVE

RELATED APPLICATIONS

This application is a 35 U.S.C. §371 filing of International Application Number PCT/GB2011/000087 which was filed on Jan. 24, 2011, which claims priority to, and the benefit of, application Ser. No. 1001075.9, filed on Jan. 22, 2010. The contents of each of these applications are hereby incorporated herein by reference.

The present invention relates to crystalline forms of a purine derivative. The invention also relates to a pharmaceutical composition containing said crystalline forms as the active ingredient, and use thereof in the prevention or treatment of disease. The invention further relates to a process for preparing the crystalline forms.

BACKGROUND TO THE INVENTION

The purine derivative of formula (I), hereinafter referred to as "compound (I)", was first disclosed in the specification of WO 2008/122767 in the name Cyclacel Limited.

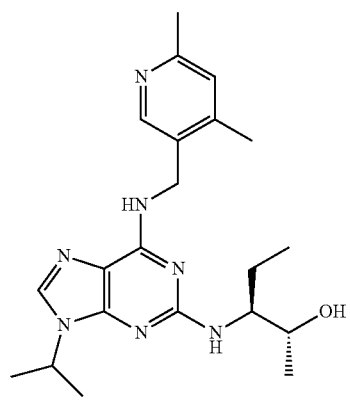

(I)

Studies have demonstrated that compound (I), having the chemical name (2R,3S)-3-(6-((4,6-dimethylpyridin-3-ylmethylamino)-9-isopropyl-9H-purin-2-ylamino)pentan-2-ol, exhibits potent CDK inhibitory activity and thus has potential therapeutic applications in the treatment of proliferative disorders, immune-mediated and inflammatory disorders, autoimmune and autoimmune-mediated disorders, kidney disorders, cardiovascular disorders, ophthalmic disorders, neurodegenerative disorders, psychiatric disorders, viral disorders, metabolic disorders and respiratory disorders.

Advantageously, compound (I) displays surprisingly high potency in cellular toxicity studies in a range of different cell lines.

The present invention seeks to provide compound (I) in crystalline form. In particular, the invention seeks to provide crystalline forms that retain the desired pharmacological activity of the compound. More specifically, but not exclusively, the present invention seeks to provide crystalline forms of compound (I) that exhibit one or more improved properties over the amorphous form.

STATEMENT OF INVENTION

A first aspect of the invention relates to a crystalline form of compound (I),

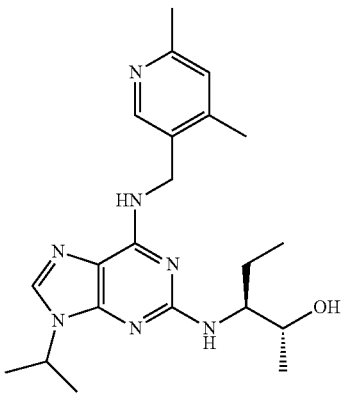

(I)

wherein said compound is in the form of the free base or a pharmaceutically acceptable salt thereof, or a solvated form of the free base or salt form thereof.

The crystalline forms of the invention typically demonstrate one or more improved properties over the amorphous form. Suitable properties include, for example, better storage stability, improved ease of handling (flowability, compressibility, stability), easier purification, and easier synthetic scale up A second aspect of the invention relates to a pharmaceutical composition comprising a crystalline form as described above as an active ingredient and a pharmaceutically acceptable diluent, excipient or carrier.

A third aspect of the invention relates to a crystalline form as described above for use in medicine.

A fourth aspect of the invention relates to a crystalline form as described above for use in the prevention or treatment of proliferative disorders, immune-mediated and inflammatory disorders, autoimmune and autoimmune-mediated disorders, kidney disorders, cardiovascular disorders, ophthalmic disorders, neurodegenerative disorders, psychiatric disorders, viral disorders, metabolic disorders and/or respiratory disorders.

A fifth aspect of the invention relates to use of a crystalline form as described above in the preparation of a medicament for the prevention or treatment of proliferative disorders, immune-mediated and inflammatory disorders, autoimmune and autoimmune-mediated disorders, kidney disorders, cardiovascular disorders, ophthalmic disorders, neurodegenerative disorders, psychiatric disorders, viral disorders, metabolic disorders and/or respiratory disorders.

A sixth aspect of the invention relates to a method for the prevention or treatment of proliferative disorders, immune-mediated and inflammatory disorders, autoimmune and autoimmune-mediated disorders, kidney disorders, cardiovascular disorders, ophthalmic disorders, neurodegenerative disorders, psychiatric disorders, viral disorders, metabolic disorders and/or respiratory disorders, said method comprising administering a pharmacologically effective amount of a crystalline form as described above to a subject in need thereof.

A seventh aspect of the invention relates to processes for preparing crystalline forms as described above.

DETAILED DESCRIPTION

The crystalline forms of the invention may be characterised by a range of different analytical techniques, including x-ray powder diffraction and differential scanning calorimetry. Further details of these techniques and equipment are set forth in the accompanying examples section.

As used herein, the term "solvate" or "solvated form" refers to a crystal having one or more molecules of solvent associated therewith as an inherent part of the crystal structure. Preferably, the solvate or solvated form is the hydrate.

In general, different plural crystalline forms (polymorphs) of the same compound can be produced by varying the crystallisation conditions used. These different crystalline forms have different three-dimensional structures and different physicochemical properties. However, the existence of polymorphs is inherently unpredictable and theoretical calculations to predict polymorphs are extremely unreliable, with many more polymorphs predicted than can actually be isolated in practice.

Preferably, the crystalline forms of the invention are at least 95% pure (in terms of the purity of the crystal form), more preferably, at least 97% pure, even more preferably, at least 98 or 99% pure (for example, as analysed by HPLC). More preferably still, the crystalline forms of the invention are at least 99.5% pure.

The present invention encompasses the crystalline form of the free base of compound (I) as well as crystalline forms of various pharmaceutically acceptable salts thereof. Specifically, the invention encompasses crystalline forms of the L-tartrate, citrate, benzenesulfonate, mesylate, maleate, L-malate, fumarate, gentisate, hydrochloride, hydrobromide and phosphate salts of compound (I).

A summary of the various crystalline forms and their properties is set forth in the following table. Each form is discussed in more detail below.

| Form Designation | Crystalline Form | Solvated? | Onset of melt (° C.) |
|---|---|---|---|
| A | Free base | No | 132 |
| B | Phosphate (from IPA) | Hydrate* | 116 |
| C | Phosphate (from ethanol) | Hydrate# | 123 |
| D | L-tartrate | No | 147 |
| E | L-tartrate | No | 178 |
| F | Citrate | No | 145 |
| G | Benzenesulfonate | No | 147 |
| H | Hydrochloride | Hydrate | 85 |
| I | Hydrochloride | No | 109 |
| J | Hydrobromide | No | 119 |
| K | Hydrobromide | Hydrate | 90 |
| L | Mesylate | No | 121 |
| M | Maleate | No | 112 |
| N | Gentisate | | |
| O | Gentisate | Yes | 92 |
| P | Fumarate | No | 135 |
| Q | L-malate | No | 83 |
| R | L-malate | No | 103 |

*Form B phosphate (from IPA) dehydrates at 67° C. to give an anhydrous form which melts at 116° C.
Form C phosphate (from ethanol) dehydrates at 68° C. to give an anhydrous form which melts at 123° C.

Summary of Selected Crystalline Forms:

| Salt/FreeBase | Summary |
|---|---|
| Free base | Anhydrous crystalline free base |
| L-tartrate | Two different crystalline polymorphs, one metastable lower melting form that readily transforms into the high melting thermodynamically stable form |
| Phosphate | Four different phosphate salts, 2 derived from isopropanol and 2 from ethanol. From each solvent there is an hydrated form that exists at lower temperature which then loses water on heating to give rise to a non-hydrated form |
| Citrate | Anhydrous mono-citrate salt |
| Benzenesulfonate | Anhydrous mono-benzene sulfonate salt |
| Hydrochloride | Four different XRPD patterns observed; one hydrated and one anhydrous suspected mono-chloride salts characterised, and two uncharacterised forms.<br>Anhydrous form converts to suspected hydrate upon storage at 40° C./75% RH |
| Hydrobromide | Two different XRPD patterns observed; one suspected hydrate and one anhydrous mono-bromide salts characterised.<br>Anhydrous form converts to suspected hydrate upon storage at 40° C./75% RH |
| Mesylate | Anhydrous mono-mesylate salt |
| Maleate | Anhydrous mono-maleate salt |
| Gentisate | Two different XRPD patterns observed; partially crystalline mono gentisate salt;<br>Crystalline mono-salt |
| Fumarate | Anhydrous mono fumarate salt |
| L-malate | Two different XRPD patterns observed; both anhydrous mono-malate salts. One form converts to the higher melting form upon storage at 40° C./75% RH |

The hydrochloride salt exhibited several forms with the observation of four XRPD patterns with deliquescence or form changes observed at elevated RH. The hydrobromide salt appeared to exist in two forms, one hygroscopic and the other only observed by storage at elevated RH. The mesylate salt exhibited deliquescence at both 25° C./97% RH and 40° C./75% RH. The maleate salt proved to be hygroscopic above 40° C./70% RH. L-malate exhibited two crystalline forms, one exhibiting deliquescence at 40° C./75% RH, the second proving to be non-hygroscopic. The gentisate salt appeared to exist in two forms, one a partially crystalline form and the other a crystalline mono salt that could be an acetonitrile solvate.

The crystalline free base (Form A) was found to be a non solvated form of compound (I), which melts at 132° C., is non-hygroscopic and has an aqueous solubility in water of 0.33 mg/ml.

Studies by the applicant have shown that the two phosphate salts (Forms B and C) can dehydrate on heating and/or reducing the ambient humidity to give two further anhydrous forms respectively. The dehydration step is reversible on cooling and/or increasing humidity. Of the two phosphate salts, Form C was discovered to be the most stable hydrate, exhibiting low hygroscopicity, complete dehydration below 100° C., melt of the respective anhydrous Form at 125° C., and high aqueous solubility (>20 mg. ml$^{-1}$).

The L-tartrate salt (Form D) was found to be a non-hydrated, non-solvated 1:1 salt with respect to tartaric acid and compound (I). It exhibits a melt at 147° C., high aqueous solubility (>20 mg. ml$^{-1}$) and is hygroscopic only above 70% RH. Form D is metastable and readily transforms into the Form E polymorph. The L-tartrate salt (Form E) was found to be a non-hydrated, non-solvated 1:1 salt with respect to tartaric acid and compound (I). It exhibits a melt at 178° C., has high aqueous solubility (43.9 mg. ml$^{-1}$) and is only slightly hygroscopic. Of the two tartrate salts Form E is the most stable form with a higher melting point. Form E is also less hygroscopic.

The citrate salt (Form F) was found to be a non-hydrated, non-solvated 1:1 salt with respect to citric acid and compound (I). It exhibits a melt at 145° C., followed by decomposition, high aqueous solubility (>15 mg. ml$^{-1}$) and is hygroscopic above only 70% RH.

The benzenesulfonate salt (Form G) was found to be a non-hydrated, non-solvated 1:1 salt with respect to benzenesulfonic acid and compound (I). It exhibits a melt at 147° C., high aqueous solubility (>20 mg. ml$^{-1}$) and is highly hygroscopic above 75% RH.

The crystalline free base Form A and the L-tartrate salt Form E are especially preferred as they are non-hydrated, are not highly hygroscopic and exhibit reasonably high melting points.

The Form E L-tartrate is the most preferred as it has a high melting point has good aqueous solubility and is only slightly hygroscopic. The fumarate (Form P) salt is also highly preferred for the same reasons.

The various forms disclosed herein can be listed in order of preference as follows:
1. L-tartrate (Form E) and crystalline free base (Form A);
2. fumarate (Form P);
3. L-malate Form (Form R);
4. citrate (Form F), phosphate (Form C) (from ethanol);
5. phosphate (Form B) (from IPA);
6. benzene sulfonate (Form G), maleate (Form M), mesylate (Form L);
7. L-malate [Form Q], tartrate [Form D];
8. hydrochlorides, hydrobromides, gentisate. (Forms H, I, J, K, N, O)

When the crystalline forms of compound (I) are allowed to stand so that they are open to the atmosphere or are mixed with water or a solvent, they may absorb water or a solvent to form a hydrate or solvate. The present invention encompasses these hydrates and solvates as well as the anhydrous/non-solvated forms.

Compound (I) can be prepared according to the procedure described in WO 2008/122767, or by a modified procedure described in the accompanying examples section.

In one preferred embodiment, the crystalline forms of the invention can be obtained from a supersaturated solution. The supersaturated solution can be prepared through dissolution of compound (I) in an appropriate solvent, optional pH adjustment of said solution, concentration of said solution, cooling said solution, addition of a solvent in which compound (I) is slightly soluble to a solution of compound (I) in a solvent in which compound (I) is readily soluble.

In another preferred embodiment, a suspension of a crystal or amorphous solid of compound (I) in an appropriate solvent is converted into a slurry and then is stirred to transform into an alternate crystalline form. This is known as solvent-mediated transformation.

In another preferred embodiment, precipitation of the crystals takes place spontaneously in the reaction vessel or can be started or accelerated by addition of a crystalline seed, by mechanical stimulation such as through use of ultrasonic waves or by scratching the inside of the reaction vessel.

The temperature for crystallisation of compound (I) or a pharmaceutically acceptable salt thereof is typically from about 0 to about 100° C., preferably from about 5° C. to about 75° C.

Precipitated crystals can be collected by filtration, centrifugation or decantation methods. Isolated crystals may be washed with an appropriate solvent.

Isolated crystals are typically dried at a temperature of from about 10 to about 100° C., preferably from about 30 to about 50° C., until the weight of the crystals becomes constant, if necessary, in the presence of a drying agent such as silica gel or calcium chloride and optionally under reduced pressure.

Dried crystals may absorb water under conditions of about 20 to 90% relative humidity at temperatures of from about 10 to about 30° C., preferably about 50 to about 80% relative humidity at temperatures of from about 20 about 30° C., until the weight of the crystalline form becomes constant.

Crystals obtained in accordance with the invention can be further purified by recrystallisation or slurry purification.

Recrystallisation may be accomplished by techniques familiar to those skilled in the art, including the following methods:
(1) Cooling method: compound (1), or a pharmaceutically acceptable salt thereof, is dissolved in a hot solvent and the resulting solution is cooled;
(2) Concentration method: a solution of compound (I), or a pharmaceutically acceptable salt thereof, is concentrated;
(3) Precipitation method: a solvent in which compound (I) or a pharmaceutically acceptable salt thereof is slightly soluble is added to a solution of compound (I) or a pharmaceutically acceptable salt thereof in a solvent in which compound (I) or a pharmaceutically acceptable salt thereof is readily soluble.

Slurry purification typically comprises stirring a suspension of compound (I), or a pharmaceutically acceptable salt thereof, in an appropriate solvent.

Solvents employed in the preparation of crystalline forms of compound (I) include ICH class 2 or preferably class 3 solvents. For example esters such as ethyl acetate, alcohols such as ethanol, ketones such as methyl ethyl ketone, ethers such as methyl t-butyl ether, alkanes such as heptane, and water. These solvents may be used singly or as mixtures. Preferred solvents include IMS, acetonitrile, tetralin, cumene, 3-methyl-1-butanol, ethanol, methanol, isopropanol, ethyl acetate, methyl acetate, isopropyl acetate, water, heptane, TBME, THF, MEK, methyl isobutyl ketone, nPrOH and nBuOAc.

The present invention encompasses individual crystalline forms as defined above, and mixtures thereof with one or more other crystalline forms.

Crystalline Free Base of Compound (I) (Form A)

One preferred embodiment of the invention relates to the crystalline form of the free base of compound (I).

Preferably, the crystalline form is characterized by an x-ray powder diffraction pattern having two or more diffraction peaks at 2[theta] values selected from 7.53±0.2, 9.60±0.2, 10.22±0.2, 11.29±0.2, 11.66±0.2, 12.26±0.2, 12.62±0.2, 13.17±0.2, 14.06±0.2, 14.85±0.2, 15.15±0.2, 15.57±0.2, 16.99±0.2, 17.68±0.2, 18.30±0.2, 18.39±0.2, 18.63±0.2, 18.97±0.2, 19.32±0.2 and 20.20±0.2. More preferably, the crystalline form is characterized by having three or more, four or more, five or more, or six or more of the aforementioned diffraction peaks. Even more preferably, the crystalline form is characterized by having at least 7, 8, 9, 10, 11, 12, 13, 14, 15, 16, 17 18 or 19 or more of the aforementioned diffraction peaks.

Even more preferably, the crystalline form is characterized by an x-ray powder diffraction pattern comprising two or more diffraction peaks at 2[theta] values selected from 7.53±0.2, 12.26±0.2, 14.06±0.2, 14.85±0.2 and 15.57±0.2. More preferably, the crystalline form is characterized by having three, four or five of the aforementioned diffraction peaks.

In one highly preferred embodiment, the crystalline form is characterized by an x-ray powder diffraction pattern in which the peak positions are substantially in accordance with the peak positions of the pattern shown in FIG. 5 or listed in Table 1.

In one preferred embodiment, the crystalline form is characterized by a differential scanning calorimetry trace recorded at a heating rate of 20° C. per minute which shows a maximum endothermic peak at a temperature between about 130° C. and about 140° C., more preferably between about 132° C. and about 138° C., even more preferably, between about 135° C. and about 138° C., more preferably still, between about 136° C. and about 138° C.

In one highly preferred embodiment, the crystalline form is characterized by a differential scanning calorimetry trace substantially in accordance with that shown in FIG. 6.

In one highly preferred embodiment, the crystalline form is monoclinic P21/c space group with unit cell dimensions of a=15.19±2 Å, b=18.34±2 Å, c=8.65±2 Å and [beta]=95.53±2°.

A further aspect of the invention relates to a process of preparing free base compound (I) in crystalline form, said process comprising crystallising amorphous compound (I) in free base form from methyl t-butyl ether (MTBE).

In one preferred embodiment, the crystalline form of the free base is obtained from a supersaturated solution.

Preferably, the process comprises heating compound (I) in MTBE to reflux, allowing the mixture to cool to room temperature, filtering the solid so formed, washing the solid with MTBE and drying under vacuum. More preferably, after refluxing, the reaction mixture is held for a period of 1 to 3 hours at a temperature below reflux (for example, 45-50° C.) before being allowed to cool to room temperature.

Another aspect of the invention relates to a product obtainable by, or obtained by, the above process.

Crystalline Citrate Salt (Form F)

In one preferred embodiment of the invention, the crystalline form is a citrate salt of compound (I).

Preferably, the crystalline form is characterized by an x-ray powder diffraction pattern having two or more diffraction peaks at 2[theta] values selected from 5.14±0.2, 7.73±0.2, 10.24±0.2, 12.70±0.2, 13.06±0.2, 14.42±0.2, 15.30±0.2, 15.98±0.2, 16.74±0.2, 17.24±0.2, 18.05±0.2, 19.04±0.2, 20.23±0.2, 21.04±0.2, 22.45±0.2, 22.75±0.2, 24.01±0.2, 25.43±0.2, 26.51±0.2, 27.48±0.2, 28.77±0.2 and 29.71±0.2 [Form F]. More preferably, the crystalline form is characterized by having three or more, four or more, five or more, or six or more of the aforementioned diffraction peaks. Even more preferably, the crystalline form is characterized by having at least 7, 8, 9, 10, 11, 12, 13, 14, 15, 16, 17, 18, 19, 20 or 21 or more of the aforementioned diffraction peaks.

More preferably, the crystalline form is characterized by an x-ray powder diffraction pattern comprising two or more diffraction peaks at 2[theta] values selected from 17.24±0.2, 18.05±0.2, 19.04±0.2, 22.45±0.2, 22.75±0.2, 24.01±0.2 and 25.43±0.2 [Form F. More preferably, the crystalline form is characterized by having three, four or five of the aforementioned diffraction peaks. Even more preferably, the crystalline form is characterized by having 6 or 7 of the aforementioned diffraction peaks.

In one highly preferred embodiment, the crystalline form is characterized by an x-ray powder diffraction pattern in which the peak positions are substantially in accordance with the peak positions of the pattern shown in FIG. 7 or listed in Table 3.

In one preferred embodiment, the crystalline form is characterized by a differential scanning calorimetry trace recorded at a heating rate of 20° C. per minute which shows maximum endothermic peaks at a temperature between about 145° C. and about 155° C. and between about 165° C. and about 200° C. More preferably, the crystalline form is characterized by a first maximum endothermic peak at a temperature between about 146° C. and about 152° C., more preferably between about 147° C. and about 151° C., and a broader second maximum endothermic peak between about 170° C. and about 195° C., more preferably between about 175° C. and about 190° C.

In one highly preferred embodiment, the crystalline form is characterized by a differential scanning calorimetry trace substantially in accordance with that shown in FIG. 8.

In one preferred embodiment, the crystalline form of the citrate salt of compound (I) is obtained from a supersaturated solution.

In one preferred embodiment, the invention relates to a process for preparing the citrate salt of compound (I) in crystalline form, said process comprising crystallizing the citrate salt from ethyl acetate.

More preferably, the invention relates to a process for preparing the citrate salt of compound (I) in crystalline form, said process comprising the steps of:
(i) preparing a reaction mixture comprising compound (I) in free base form, citric acid and ethyl acetate; and
(ii) isolating the crystalline citrate salt from the reaction mixture.

Preferably, the process comprises stirring a mixture of compound (I) and citric acid in ethyl acetate at ambient temperature, subjecting the mixture to a heat/cool cycle (60° C./RT, 4 hours) for at least 24 hours, more preferably, 48 hours, even more preferably 72 hours, filtering the solid so formed, washing the solid with ethyl acetate and drying under vacuum. More preferably, the mixture is stored in a shaker during the heat/cool cycle.

Another aspect of the invention relates to a product obtainable by, or obtained by, the above process.

Crystalline Phosphate Salt (Forms B and C)

In one preferred embodiment of the invention, the crystalline form is a phosphate salt.

Studies by the applicant have shown that the crystalline phosphate salt exists in at least two different forms, depending on the solvent used for crystallisation. In turn, each of these two different forms exist in hydrated and anhydrous forms, thereby giving rise to at least four different crystalline forms. At ambient temperature and humidity the two forms are designated Forms B and C.

In one preferred embodiment, the phosphate salt is crystallised from propan-2-ol (Form B).

In another preferred embodiment, the phosphate salt is crystallised from ethanol (Form C).

Crystalline Phosphate Salt—Propan-2-ol Preparation (Form B)

In one preferred embodiment, the crystalline form is characterized by an x-ray powder diffraction pattern having two or more diffraction peaks at 2[theta] values selected from 6.46±0.2, 8.88±0.2, 9.67±0.2, 10.47±0.2, 12.78±0.2, 15.33±0.2, 16.12±0.2, 16.82±0.2, 18.13±0.2, 19.38±0.2, 19.95±0.2, 20.97±0.2, 24.11±0.2, 24.83±0.2, 26.54±0.2 and 28.11±0.2 [Form B]. More preferably, the crystalline form is characterized by having three or more, four or more, five or more, or six or more of the aforementioned diffraction peaks. More preferably, the crystalline form is characterized by having 7, 8, 9, 10, 11, 12, 13, 14 or 15 or more of the aforementioned diffraction peaks.

Preferably, the crystalline form is characterized by an x-ray powder diffraction pattern comprising two or more diffraction peaks at 2[theta] values selected from 6.46±0.2, 16.12±0.2, 18.13±0.2, 19.38±0.2, 19.95±0.2, 20.97±0.2, 24.11±0.2 and 24.83±0.2 [Form B]. More preferably, the crystalline form is characterized by having three, four or five of the aforementioned diffraction peaks. More preferably, the crystalline form is characterized by having 6, 7 or 8 of the aforementioned diffraction peaks In one highly preferred embodiment, the crystalline form is characterized by an x-ray powder diffraction pattern in which the peak positions are substantially in accordance with the peak positions of the pattern shown in FIG. 11 or listed in Table 6.

In one preferred embodiment, the crystalline form is characterized by a differential scanning calorimetry trace recorded at a heating rate of 20° C. per minute which shows maximum endothermic peaks at a temperature between about 65° C. and about 90° C. and between about 114° C. and about 130° C. Preferably, the crystalline form is characterized by a first maximum endothermic peak at a temperature between about 70° C. and about 88° C., more preferably, between about 75° C. and about 85° C. Preferably, the crystalline form is characterized by a second maximum endothermic peak at a temperature between about 118° C. and about 125° C., more preferably, between about 120° C. and about 125° C.

In one highly preferred embodiment, the crystalline form is characterized by a differential scanning calorimetry trace substantially in accordance with that shown in FIG. 12.

The present invention encompasses the crystalline phosphate salts in anhydrous and hydrated forms.

In one preferred embodiment, the crystalline form of the phosphate salt of compound (I) is obtained by precipitation.

In one preferred embodiment, the invention relates to a process for preparing the phosphate salt of compound (I) in crystalline form, said process comprising crystallizing the phosphate salt from a solution of propan-2-ol.

More preferably, the invention relates to a process for preparing a crystalline phosphate salt of compound (I), said process comprising the steps of:
(i) preparing a reaction mixture comprising compound (I) in free base form, propan-2-ol and a solution of phosphoric acid in water; and
(ii) isolating the crystalline phosphate salt from the reaction mixture.

Preferably, the process comprises adding a solution of phosphoric acid in water to a stirring solution of compound (I) in propan-2-ol at room temperature in a cool water bath. More preferably, the process comprises adding further propan-2-ol to the mixture and stirring for at least 1 hour before filtering the solid so formed, washing the solid with propan-2-ol and drying under vacuum. Preferably, the solid is isolated by vacuum filtration.

Preferably, the solution of phosphoric acid in water is an 85% solution (w/w).

Another aspect of the invention relates to a product obtainable by, or obtained by, the above process.

Crystalline Phosphate Salt—Ethanol Preparation (Form C)

In another preferred embodiment, the crystalline form is characterized by an x-ray powder diffraction pattern having two or more diffraction peaks at 2[theta] values selected from 6.49±0.2, 8.91±0.2, 9.75±0.2, 10.52±0.2, 13.03±0.2, 15.44±0.2, 16.27±0.2, 17.85±0.2, 18.29±0.2, 19.52±0.2, 20.02±0.2, 21.11±0.2, 22.80±0.2, 24.92±0.2, 28.33±0.2 and 29.41±0.2 [Form C]. More preferably, the crystalline form is characterized by having three or more, four or more, five or more, or six or more of the aforementioned diffraction peaks. More preferably, the crystalline form is characterized by having 7, 8, 9, 10, 11, 12, 13, 14 or 15 or more of the aforementioned diffraction peaks.

Preferably, the crystalline form is characterized by an x-ray powder diffraction pattern comprising two or more diffraction peaks at 2[theta] values selected from 6.49±0.2, 16.27±0.2, 18.29±0.2, 19.52±0.2, 20.02±0.2, 21.11±0.2, 22.80±0.2, 24.92±0.2 and 29.41±0.2 [Form C]. More preferably, the crystalline form is characterized by having three, four or five of the aforementioned diffraction peaks. More preferably, the crystalline form is characterized by having 6, 7, 8 or 9 of the aforementioned diffraction peaks.

In one highly preferred embodiment, the crystalline form is characterized by an x-ray powder diffraction pattern in which the peak positions are substantially in accordance with the peak positions of the pattern shown in FIG. 13 or listed in Table 5.

In one highly preferred embodiment, the crystalline form is characterized by a differential scanning calorimetry trace recorded at a heating rate of 20° C. per minute which shows maximum endothermic peaks at a temperature between about 66° C. and about 90° C. and between about 120° C. and about 135° C. Preferably, the crystalline form is characterized by a first maximum endothermic peak at a temperature between about 70° C. and about 88° C., more preferably, between about 80° C. and about 87° C. Preferably, the crystalline form is characterized by a second maximum endothermic peak at a temperature between about 125° C. and about 135° C., more preferably, between about 130° C. and about 135° C.

In one highly preferred embodiment, the crystalline form is characterized by a differential scanning calorimetry trace substantially in accordance with that shown in FIG. 14.

The present invention encompasses the crystalline phosphate salts in anhydrous and hydrated forms.

In one preferred embodiment, the crystalline form of the phosphate salt of compound (I) is obtained by precipitation.

In one preferred embodiment, the invention relates to a process for preparing the phosphate salt of compound (I) in crystalline form, said process comprising crystallizing the phosphate salt from ethanol.

More preferably, the invention relates to a process for preparing a crystalline phosphate salt of compound (I), said process comprising the steps of:
(i) preparing a reaction mixture comprising compound (I) in free base form, ethanol and a solution of phosphoric acid in water; and (ii) isolating the crystalline phosphate salt from the reaction mixture.

Preferably, the process comprises adding a solution of phosphoric acid in water to a stirring solution of compound (I) in ethanol at room temperature in a cool water bath. More preferably, the process comprises further stirring the mixture at room temperature for at least 2 hours before filtering the solid so formed, washing the solid with ethanol and drying under vacuum. Preferably, the solid is isolated by vacuum filtration. Preferably, the solid is dried in a vacuum oven, for example, at a temperature of at least 40° C. for at least 12, more preferably 24 hours.

Preferably, the solution of phosphoric acid in water is an 85% solution (w/w).

Another aspect of the invention relates to a product obtainable by, or obtained by, the above process.

Crystalline L-Tartrate Salt

In one preferred embodiment of the invention, the crystalline form is a tartrate salt, more preferably, the L-tartrate salt. Studies by the applicant have revealed that the tartrate salt exists in at least two different forms, designated hereinafter as Form D and Form E.

L-Tartrate Salt (Form D)

In one preferred embodiment, the crystalline form is characterized by an x-ray powder diffraction pattern having two or more diffraction peaks at 2[theta] values selected from 3.82±0.2, 7.57±0.2, 8.12±0.2, 10.53±0.2, 11.39±0.2, 12.00±0.2, 13.54±0.2, 15.15±0.2, 16.35±0.2, 16.88±0.2, 17.37±0.2, 18.51±0.2, 18.98±0.2, 19.77±0.2, 21.06±0.2, 22.70±0.2, 23.47±0.2, 24.66±0.2 and 28.73±0.2 [Form D]. More preferably, the crystalline form is characterized by having three or more, four or more, five or more, or six or more of the aforementioned diffraction peaks. More preferably, the crystalline form is characterized by having 7, 8, 9, 10, 11, 12, 13, 14, 15, 16, 17 or 18 or more of the aforementioned diffraction peaks.

Preferably, the crystalline form is characterized by an x-ray powder diffraction pattern comprising two or more diffraction peaks at 2[theta] values selected from 3.82±0.2, 7.57±0.2, 15.15±0.2, 16.88±0.2, 19.77±0.2, 22.70±0.2, 23.47±0.2, 24.66±0.2 and 28.73±0.2 [Form D]. More preferably, the crystalline form is characterized by having three, four or five of the aforementioned diffraction peaks. More preferably, the crystalline form is characterized by having 6, 7, 8 or 9 of the aforementioned diffraction peaks.

In one highly preferred embodiment, the crystalline form is characterized by an x-ray powder diffraction pattern in which the peak positions are substantially in accordance with the peak positions of the pattern shown in FIG. 3 or listed in Table 2.

In one preferred embodiment, the crystalline form is characterized by a differential scanning calorimetry trace recorded at a heating rate of 20° C. per minute which shows a maximum endothermic peak at a temperature between about 145° C. and about 154° C., more preferably between about 148° C. and about 153° C., even more preferably, between about 150° C. and about 152° C.

In one highly preferred embodiment, the crystalline form is characterized by a differential scanning calorimetry trace substantially in accordance with that shown in FIG. 4.

In one preferred embodiment, the crystalline form of the tartrate salt of compound (I) is obtained by precipitation.

In one preferred embodiment, the invention relates to a process for preparing the L-tartrate salt of compound (I) in crystalline form, said process comprising crystallizing the L-tartrate salt from a solution of ethyl acetate.

More preferably, the invention relates to a process for preparing a crystalline form of the L-tartrate salt of compound (I), said process the steps of:
(i) preparing a reaction mixture comprising compound (I) in free base form, L-tartaric acid and ethyl acetate; and
(ii) isolating the crystalline L-tartrate salt (Form D) from the reaction mixture.

Preferably, the process comprises stirring a mixture of L-tartaric acid, compound (I) and ethyl acetate under ambient conditions for at least 1 hour, more preferably, at least 2 hours, and isolating the precipitate so formed, washing with ethyl acetate and drying in a vacuum oven. Preferably, the precipitate is isolated by vacuum filtration. Preferably, the precipitate is dried at a temperature of at least 40° C. for at least 12, more preferably 24 hours.

Another aspect of the invention relates to a product obtainable by, or obtained by, the above process.

L-Tartrate Salt (Form E)

In one preferred embodiment of the invention, the crystalline form is characterized by an x-ray powder diffraction pattern having two or more diffraction peaks at 2[theta] values selected from 6.67±0.2, 8.237±0.2, 9.777±0.2, 11.96±0.2, 12.38±0.2, 13.06±0.2, 13.38±0.2, 13.94±0.2, 14.90±0.2, 15.40±0.2, 15.95±0.2, 16.27±0.2, 16.54±0.2, 17.36±0.2, 17.57±0.2, 17.86±0.2, 19.64±0.2, 19.86±0.2, 20.12±0.2, 20.73±0.2, 21.14±0.2, 21.58±0.2, 22.57±0.2, 22.95±0.2, 23.29±0.2, 23.57±0.2, 24.07±0.2, 24.63±0.2, 25.30±0.2, 26.38±0.2, 27.09±0.2, 27.67±0.2, 27.97±0.2, 28.91±0.2, 29.28±0.2, 30.08±0.2, 30.41±0.2, 31.90±0.2 and 34.49±0.2 (Form E). More preferably, the crystalline form is characterized by having three or more, four or more, five or more, or six or more of the aforementioned diffraction peaks. More preferably, the crystalline form is characterized by having 7, 8, 9, 10 . . . 38 or more of the aforementioned diffraction peaks.

Preferably, the crystalline form is characterized by an x-ray powder diffraction pattern comprising two or more diffraction peaks at 2[theta] values selected from 6.67±0.2, 13.06±0.2, 13.38±0.2, 14.90±0.2, 17.36±0.2, 17.57±0.2, 19.64±0.2, 20.73±0.2, 23.57±0.2 and 25.30±0.2 (Form E). More preferably, the crystalline form is characterized by having three, four or five of the aforementioned diffraction peaks. More preferably, the crystalline form is characterized by having 6, 7, 8, 9 or 10 of the aforementioned diffraction peaks.

In one highly preferred embodiment, the crystalline form is characterized by an x-ray powder diffraction pattern in which the peak positions are substantially in accordance with the peak positions of the pattern shown in FIG. 1 or listed in Table 7.

In one highly preferred embodiment, the crystalline form is characterized by a differential scanning calorimetry trace recorded at a heating rate of 20° C. per minute which shows a maximum endothermic peak at a temperature between about 176° C. and about 185° C., more preferably, between about 178° C. and about 184° C., even more preferably, between about 180° C. and about 183° C.

In one highly preferred embodiment, the crystalline form is characterized by a differential scanning calorimetry trace substantially in accordance with that shown in FIG. 2.

In one preferred embodiment, the Form E L-tartrate salt is obtained by recrystallising the Form D L-tartrate salt of compound (I) from a mixture of ethanol and acetonitrile In one preferred embodiment, the invention relates to a process for preparing the L-tartrate salt (Form E) of compound (I) in crystalline form, said process comprising crystallizing the L-tartrate salt (Form D) from a mixture of ethanol and acetonitrile. Preferably, the L-tartrate salt (Form E) is recrystallized from a mixture of ethanol and acetonitrile.

Thus, one aspect of the invention relates to a process for preparing Form E L-tartrate salt of compound (I) in crystalline form, said process comprising the steps of:
(i) preparing a reaction mixture comprising compound (I) in free base form, L-tartaric acid and ethyl acetate;
(ii) isolating the crystalline L-tartrate salt (Form D) from the reaction mixture;
(iii) recrystallizing the crystalline L-tartrate salt (Form D) obtained in step (ii) from a mixture of ethanol and acetonitrile; and
(iv) isolating the crystalline L-tartrate salt (Form E) from the reaction mixture.

Preferably, step (iii) comprises forming a suspension of the crystalline L-tartrate salt (Form D) obtained in step (ii) in ethanol and heating to at least 60° C., adding acetonitrile to the mixture and heating the mixture at reflux to form a solution. Preferably, the solution is then hot filtered and allowed to cool to room temperature, more preferably at a rate of about 5-10° C./hour. Preferably, the resulting suspension is then stirred for at least 12 hours at room temperature before filtering off the solid, washing with ethanol and drying. Preferably, the solid is dried in a vacuum oven at a temperature of at least 50° C. for at least 12, more preferably 24 hours. This process is referred to hereinafter as the "unseeded" process.

Preferably, the ratio of ethanol to acetonitrile is from about 3:1 to about 10:1. More preferably, the ratio of ethanol to acetonitrile is 4:1 or 6:1. Even more preferably, the ratio of ethanol to acetonitrile is 4:1, 5:1 or 6:1.

In another embodiment, the Form E L-tartrate salt is prepared from a slurry conversion of a mixture of Form D L-tartrate salt of compound (I) and Form E L-tartrate salt of compound (I).

Thus, another aspect of the invention relates to a process for preparing Form E L-tartrate salt of compound (I) in crystalline form, said process comprising the steps of:
(i) preparing crystalline L-tartrate salt (Form D) by the process described above;
(ii) preparing crystalline L-tartrate salt (Form E) by the process described above;
(iii) forming a slurry of L-tartrate salt (Form D) and L-tartrate salt (Form E) in a solvent selected from ethyl acetate, propan-2-ol, IMS and acetonitrile; and
(iv) isolating the crystalline L-tartrate salt (Form E) from the slurry.

In one preferred embodiment, the slurry in step (iii) is a mixture of 50-99% by weight of L-tartrate salt (Form D) and 1-50 by weight of % L-tartrate salt (Form E). More preferably, the slurry in step (iii) is a 50:50 mixture of L-tartrate salt (Form D) and L-tartrate salt (Form E).

Preferably, the slurry is heated to a temperature of at least 40° C., more preferably at least 45° C. for at least 24 hours, more preferably at least 48 hours, before isolating the solid by filtration, washing and drying under vacuum.

In one preferred embodiment, the Form E L-tartrate salt is obtained by recrystallising Form D L-tartrate salt from a mixture of ethanol and acetonitrile by seeding with one or more crystals of the Form E L-tartrate salt.

Thus, one aspect relates to a process for preparing Form E L-tartrate salt which comprises recrystallizing Form D L-tartrate salt from a mixture of ethanol and acetonitrile, preferably with seeding using one or more crystals of the Form E L-tartrate salt.

Thus, more preferably the invention relates to a process for preparing Form E L-tartrate salt of compound (I) in crystalline form, said process comprising the steps of:
(i) preparing crystalline L-tartrate salt (Form D) by the process described above;
(ii) preparing crystalline L-tartrate salt (Form E) by the process described above;
(iii) dissolving the crystalline L-tartrate salt (Form D) obtained in step (i) in a mixture of ethanol and acetonitrile and seeding with crystalline L-tartrate salt (Form E); and
(iv) isolating the crystalline L-tartrate salt (Form E) from the reaction mixture.

This process is referred to hereinafter as the "seeded" process. Preferred embodiments of this aspect identical to those set forth above for the "unseeded" process.

Yet another aspect of the invention relates to a process for preparing Form E L-tartrate salt of compound (I) in crystalline form, said process comprising the steps of:
(i) preparing crystalline L-tartrate salt (Form E) by the process described above;
(ii) preparing a reaction mixture comprising compound (I) in free base form, L-tartaric acid and ethyl acetate;
(iii) seeding the mixture obtained in step (ii) with crystalline L-tartrate salt (Form E); and
(iv) isolating crystalline L-tartrate salt (Form E) from the reaction mixture.

Thus, one aspect relates to a process for preparing Form E L-tartrate salt which comprises crystallizing Form E L-tartrate salt from a solution of ethyl acetate, preferably seeding with one or more crystals of the Form E L-tartrate salt.

In one preferred embodiment, the Form E L-tartrate salt is prepared from compound (I) in free base form. Preferably, the Form E L-tartrate salt is obtained by treating compound (I) in free base form with a solution of tartaric acid in water/ethanol, and seeding the resulting mixture with a crystal of Form E L-tartrate salt obtained by any one of the methods described herein.

Thus, one particularly preferred embodiment of the invention relates to a process for preparing Form E L-tartrate salt of compound (I) in crystalline form, said process comprising the steps of:
(i) preparing a reaction mixture comprising free base compound (I) in ethanol;
(ii) adding solution of tartaric acid in water/ethanol to the reaction mixture obtained in step (i);
(ii) filtering the reaction mixture formed in step (ii);
(iii) seeding the filtrate with crystalline L-tartrate salt (Form E) prepared in accordance with one of the above-described methods; and
(iv) isolating crystalline L-tartrate salt (Form E) from the reaction mixture.

Preferably, for this embodiment, the reaction mixture formed in step (i) is heated at reflux. Preferably, the solution of tartaric acid in water/ethanol is added whilst maintaining the temperature at reflux. Preferably, step (ii) comprises polish filtering the reaction mixture before cooling to about 70° C. Preferably, after addition of the seed crystal, the mixture is stirred at a temperature of at least 70° C. for at least 1 hour before cooling to room temperature. Preferably, the mixture is then stirred for at least 1 hour, more preferably at least 2 hours, before filtering. Preferably, the product obtained in the filtration step is washed with ethanol and dried.

Another aspect of the invention relates to a product obtainable by, or obtained by, the above processes.

Crystalline Benzenesulfonic Acid Salt (Form G)

In one preferred embodiment of the invention, the crystalline form is a benzenesulfonate salt.

Preferably, the crystalline form is characterized by an x-ray powder diffraction pattern having two or more diffraction peaks at 2[theta] values selected from 5.72±0.2, 11.45±0.2, 11.79±0.2, 15.56±0.2, 16.57±0.2, 18.04±0.2, 19.14±0.2, 20.02±0.2, 21.05±0.2, 22.80±0.2, 23.16±0.2, 24.44±0.2, 25.40±0.2 and 28.74±0.2 [Form G]. More preferably, the crystalline form is characterized by having three or more, four or more, five or more, or six or more of the aforementioned diffraction peaks. More preferably, the crystalline form is characterized by having 7, 8, 9, 10, 11, 12 or 13 or more of the aforementioned diffraction peaks.

More preferably, the crystalline form is characterized by an x-ray powder diffraction pattern comprising two or more diffraction peaks at 2[theta] values selected from 15.56±0.2, 16.57±0.2, 18.04±0.2, 20.02±0.2, 21.05±0.2, 22.80±0.2, 23.16±0.2 and 24.44±0.2 [Form G]. More preferably, the crystalline form is characterized by having three, four or five of the aforementioned diffraction peaks. More preferably, the crystalline form is characterized by having 6, 7, 8, 9, 10, 11, 12, 13 or 14 of the aforementioned diffraction peaks.

In one highly preferred embodiment, the crystalline form is characterized by an x-ray powder diffraction pattern in which the peak positions are substantially in accordance with the peak positions of the pattern shown in FIG. 9 or listed in Table 4.

In one preferred embodiment, the crystalline form is characterized by a differential scanning calorimetry trace recorded at a heating rate of 20° C. per minute which shows a maximum endothermic peak at a temperature between about 145° C. and about 155° C., more preferably, between about 146° C. and about 154° C., even more preferably, between about 147° C. and about 154° C.

In one highly preferred embodiment, the crystalline form is characterized by a differential scanning calorimetry trace substantially in accordance with that shown in FIG. 10.

In one preferred embodiment, the crystalline form of the benzenesulfonic acid salt of compound (I) is obtained from a supersaturated solution.

In one preferred embodiment, the invention relates to a process for preparing the benzenesulfonic acid salt of compound (I) in crystalline form, said process comprising crystallizing the benzenesulfonic acid salt from a solution of methyl t-butyl ether (MTBE).

More preferably, the invention relates to a process for preparing the benzenesulfonic acid salt of compound (I) in crystalline form, said process comprising the steps of:
(i) preparing a reaction mixture comprising compound (I) in free base form, benzenesulfonic acid and methyl t-butyl ether (MTBE); and
(ii) isolating the crystalline benzenesulfonic acid salt from the reaction mixture.

Preferably, the process comprises stirring a mixture of compound (I) and benzenesulfonic acid in MTBE at ambient temperature for at least 24 hours. Preferably, the mixture is then subjected to a heat/cool cycle (60° C./RT, 4 hours) for at least 24 hours, more preferably, 48 hours, even more preferably 72 hours, filtering the solid so formed, washing the solid with MTBE and drying under vacuum. More preferably, the mixture is stored in a shaker during the heat/cool cycle.

Another aspect of the invention relates to a product obtainable by, or obtained by, the above process.

Crystalline Hydrochloride Salt (Form H)

In one preferred embodiment of the invention, the crystalline form of compound (I) is a hydrochloride salt.

Preferably, the crystalline form is characterized by an x-ray powder diffraction pattern having two or more diffraction peaks at 2[theta] values selected from 5.6 t 0.2, 8.6±0.2, 9.5±0.2, 10.9±0.2, 11.2±0.2, 12.7±0.2, 13.0±0.2, 14.3±0.2, 16.0±0.2, 17.3±0.2, 17.7±0.2, 18.8±0.2, 19.1±0.2, 20.3±0.2, 20.7±0.2, 22.9±0.2, 23.6±0.2, 24.5±0.2, 25.0±0.2, 25.5±0.2, 25.8±0.2, 26.4±0.2 and 29.1±0.2 [Form H]. More preferably, the crystalline form is characterized by having 1, 2, 3, 4 . . . 22 or 23 of the aforementioned diffraction peaks.

Preferably, the crystalline form is characterized by an x-ray powder diffraction pattern in which the peak positions are substantially in accordance with the peak positions of the pattern shown in FIG. 19 or listed in Table 8.

Preferably, the crystalline form is characterized by a differential scanning calorimetry trace recorded at a heating rate of 20° C. per minute which shows endothermic peaks at temperatures with onset at about 51° C., about 84° C., about 97° C. and about 144° C.

In one preferred embodiment, the invention relates to a process for preparing the hydrochloride salt (Form H) of compound (I) in crystalline form, said process comprising crystallizing the hydrochloride salt (Form H) from methyl t-butyl ether (MTBE).

A further aspect of the invention relates to a process for preparing the hydrochloric acid salt of compound (I) in crystalline form, said process comprising the steps of:
(i) preparing a reaction mixture comprising compound (I) in free base form, hydrochloric acid and methyl t-butyl ether (MTBE); and
(ii) isolating the crystalline hydrochloric acid salt from the reaction mixture.

Preferably, the process comprises agitating a mixture of compound (I) and hydrochloric acid in MTBE at ambient temperature. Preferably, the mixture is then subjected to a heat/cool cycle (40° C./RT, 4 hours) for at least 24 hours, more preferably, 48 hours, even more preferably 72 hours, filtering the solid so formed, washing the solid with MTBE and drying under vacuum. More preferably, the mixture is stored in a shaker during the heat/cool cycle.

Another aspect of the invention relates to a product obtainable by, or obtained by, the above process.

Crystalline Hydrochloride Salt (Form I)

In another preferred embodiment, the crystalline form of the hydrochloride salt is characterized by an x-ray powder diffraction pattern having two or more diffraction peaks at 2[theta] values selected from 4.9±0.2, 6.4±0.2, 7.5±0.2, 12.1±0.2, 14.4±0.2, 19.8±0.2, 21.5±0.2, 23.4±0.2 and 25.7±0.2 [Form I]. More preferably, the crystalline form is characterized by having 1, 2, 3, 4, 5, 6, 7, 8 or 9 of the aforementioned diffraction peaks.

Preferably, the crystalline form is characterized by an x-ray powder diffraction pattern in which the peak positions are substantially in accordance with the peak positions of the pattern shown in FIG. 20 or listed in Table 9.

Preferably, the crystalline form is characterized by a differential scanning calorimetry trace recorded at a heating rate of 20° C. per minute which shows endothermic peaks with onset temperatures at about 98° C. and about 130° C.

In one preferred embodiment, the invention relates to a process for preparing the hydrochloride salt (Form I) of compound (I) in crystalline form, said process comprising crystallizing the hydrochloride salt (Form I) from ethyl acetate.

A further aspect of the invention relates to a process for preparing the hydrochloric acid salt of compound (I) in crystalline form, said process comprising the steps of:
(i) preparing a reaction mixture comprising compound (I) in free base form, hydrochloric acid and ethyl acetate; and
(ii) isolating the crystalline hydrochloric acid salt from the reaction mixture.

Preferably, the process comprises agitating a mixture of compound (I) and hydrochloric acid in ethyl acetate at ambient temperature. Preferably, the mixture is then subjected to a heat/cool cycle (40° C./RT, 4 hours) for at least 24 hours, more preferably, 48 hours, even more preferably 72 hours. Preferably, the solid so formed is filtered, washed with ethyl acetate and dried under vacuum. More preferably, the mixture is stored in a shaker during the heat/cool cycle.

Another aspect of the invention relates to a product obtainable by, or obtained by, the above process.

Crystalline Hydrobromide Salt (Form J)

In one preferred embodiment of the invention, the crystalline form of compound (I) is a hydrobromide salt.

Preferably, the crystalline form is characterized by an x-ray powder diffraction pattern having two or more diffraction peaks at 2[theta] values selected from 6.4±0.2, 7.2±0.2, 12.0±0.2, 14.4±0.2, 17.1±0.2, 19.6±0.2, 21.4±0.2 and 25.5±0.2 [Form J]. More preferably, the crystalline form is characterized by having 1, 2, 3, 4, 5, 6, 7 or 8 of the aforementioned diffraction peaks.

Preferably, the crystalline form is characterized by an x-ray powder diffraction pattern in which the peak positions are substantially in accordance with the peak positions of the pattern shown in FIG. 21 or listed in Table 10.

In one preferred embodiment, the crystalline form is characterized by a differential scanning calorimetry trace recorded at a heating rate of 20° C. per minute which shows a maximum endothermic peak with an onset at a temperature of about 138° C.

In one preferred embodiment, the invention relates to a process for preparing the hydrobromic acid salt (Form J) of compound (I) in crystalline form, said process comprising crystallizing the hydrobromic acid (Form J) salt from ethyl acetate.

A further aspect of the invention relates to a process for preparing the hydrobromic acid salt of compound (I) in crystalline form, said process comprising the steps of:
(i) preparing a reaction mixture comprising compound (I) in free base form, hydrobromic acid and ethyl acetate; and
(ii) isolating the crystalline hydrobromic acid salt from the reaction mixture.

Preferably, the process comprises agitating a mixture of compound (I) and hydrobromic acid in ethyl acetate at ambient temperature. Preferably, the mixture is then subjected to a heat/cool cycle (40° C./RT, 4 hours) for at least 24 hours, more preferably, 48 hours, even more preferably 72 hours. Preferably, the solid so formed is filtered, washed with ethyl acetate and dried under vacuum. More preferably, the mixture is stored in a shaker during the heat/cool cycle.

Another aspect of the invention relates to a product obtainable by, or obtained by, the above process.

Crystalline Hydrobromide Salt (Form K)

In one preferred embodiment, the crystalline form of compound (I) is characterized by a differential scanning calorimetry trace recorded at a heating rate of 20° C. per minute which shows maximum endothermic peak at temperatures of about 51° C. and 90° C.

Preferably, the crystalline form is characterized by an x-ray powder diffraction pattern having two or more diffraction peaks at 2[theta] values selected from 5.7±0.2, 16.4±0.2, 17.7±0.2, 18.4±0.2, 19.6±0.2, 20.5±0.2, 24.1±0.2, 25.3±0.2, 26.0±0.2 and 28.1±0.2 [Form K]. More preferably, the crystalline form is characterized by having 1, 2, 3, 4, 5, 6, 7, 8, 9 or 10 of the aforementioned diffraction peaks.

Preferably, the crystalline form is characterized by an x-ray powder diffraction pattern in which the peak positions are substantially in accordance with the peak positions of the pattern shown in FIG. 28 or listed in Table 17.

In one preferred embodiment, the crystalline form is characterized by a DSC/TGA trace substantially in accordance with FIG. 29.

A further aspect of the invention relates to a process for preparing the hydrobromic acid salt of compound (I) (Form K) in crystalline form which comprises subjecting the Form J hydrobromic acid salt to a temperature of at least 40° C. at a relative humidity of at least 75% for 7 days.

More preferably, the invention relates to a process for preparing the hydrobromic acid salt of compound (I) (form K) in crystalline form, said process comprising the steps of:
(i) preparing a reaction mixture comprising compound (I) in free base form, hydrobromic acid and ethyl acetate;
(ii) isolating the crystalline hydrobromic acid salt (form J) from the reaction mixture;
(iii) storing the crystalline hydrobromic acid salt (form J) from step (ii) at 40° C./75% RH to form crystalline hydrobromic acid salt (form K).

Preferably, step (iii) comprises storing the crystalline hydrobromic acid salt (form J) for an extended period, more preferably, for at least 24 hours, more preferably, 48 hours, even more preferably 72 hours, even more preferably for at least 7 days. The crystalline product is then filtered, washed and dried under vacuum.

Another aspect of the invention relates to a product obtainable by, or obtained by, the above processes.

Crystalline Mesylate Salt (Form L)

In one preferred embodiment, the crystalline form of compound (I) is a mesylate salt.

Preferably, the crystalline form is characterized by an x-ray powder diffraction pattern having two or more diffraction peaks at 2[theta] values selected from 6.3±0.2, 7.9±0.2, 12.5±0.2, 13.4±0.2, 14.6±0.2, 15.9±0.2, 16.5±0.2, 17.5±0.2, 18.1±0.2, 18.7±0.2, 19.3±0.2, 20.0±0.2, 20.6±0.2, 20.9±0.2, 21.7±0.2, 22.6±0.2, 23.8±0.2, 24.5±0.2, 25.1±0.2, 25.5±0.2, 26.1±0.2, 27.5±0.2, 29.1±0.2, 29.7±0.2 and 30.3±0.2 [Form L]. More preferably, the crystalline form is characterized by having 1, 2, 3, 4, 5 . . . 25 of the aforementioned diffraction peaks.

Preferably, the crystalline form is characterized by an x-ray powder diffraction pattern in which the peak positions are substantially in accordance with the peak positions of the pattern shown in FIG. 22 or listed in Table 11.

Preferably, the crystalline form is characterized by a differential scanning calorimetry trace recorded at a heating rate of 20° C. per minute which shows a maximum endothermic peak with an onset temperature of about 126° C.

In one preferred embodiment, the crystalline form is characterized by a DSC/TGA trace substantially in accordance with FIG. 30.

In one preferred embodiment, the invention relates to a process for preparing the mesylate salt of compound (I) in crystalline form, said process comprising crystallizing the mesylate salt from TBME.

More preferably, the invention relates to a process for preparing the mesylate salt of compound (I) in crystalline form, said process comprising the steps of:
(i) preparing a reaction mixture comprising compound (I) in free base form, methanesulfonic acid and TBME; and
(ii) isolating the crystalline mesylate salt from the reaction mixture.

Preferably, the process comprises agitating a mixture of compound (I) and methanesulfonic acid in TBME at ambient temperature for at least 12 hours, more preferably at least 16 hours, or at least 24 hours. Preferably, the mixture is then heated to at least 40° C. and stirred for at least 1 hour, before cooling to room temperature and stirring for at least 12 hours. Preferably, THF is added to the mixture and stirring continued for at least a further 2 hours. Preferably, the mixture is then subjected to a heat/cool cycle (40° C./RT, 4 hours) for at least 24 hours, more preferably, 48 hours, even more preferably 72 hours. Preferably, TBME is added to the mixture and the resulting solid filtered, washed with TBME and dried under vacuum. More preferably, the mixture is stored in a shaker during the heat/cool cycle.

Another aspect of the invention relates to a product obtainable by, or obtained by, the above process.

Crystalline Maleate Salt (Form M)

In one preferred embodiment, the crystalline form of compound (I) is a maleate salt.

Preferably, the crystalline form is characterized by an x-ray powder diffraction pattern having two or more diffraction peaks at 2[theta] values selected from 3.8±0.2, 7.6±0.2, 8.5±0.2, 10.8±0.2, 11.4±0.2, 12.2±0.2, 15.2±0.2, 15.8±0.2, 17.0±0.2, 18.0±0.2, 18.8±0.2, 19.4±0.2, 20.3±0.2, 21.6±0.2, 22.6±0.2, 23.6±0.2, 24.3±0.2, 24.8±0.2, 26.0±0.2, 27.2±0.2, 27.9±0.2, 28.2±0.2, 28.8±0.2, 29.9±0.2, 30.2±0.2, 31.7±0.2, 32.7±0.2 and 33.2±0.2 [Form M]. More preferably, the crystalline form is characterized by having 1, 2, 3, 4, 5, 6 . . . or 28 of the aforementioned diffraction peaks.

Preferably, the crystalline form is characterized by an x-ray powder diffraction pattern in which the peak positions are substantially in accordance with the peak positions of the pattern shown in FIG. 23 or listed in Table 12.

Preferably, the crystalline form is characterized by a differential scanning calorimetry trace recorded at a heating rate of 20° C. per minute which shows maximum endothermic peak at an onset temperature of about 116° C.

In one preferred embodiment, the crystalline form is characterized by a DSC/TGA trace substantially in accordance with FIG. 31.

In one preferred embodiment, the invention relates to a process for preparing the maleate salt of compound (I) in crystalline form, said process comprising crystallizing the maleate salt from TBME.

More preferably, the invention relates to a process for preparing the maleate salt of compound (I) in crystalline form, said process comprising the steps of:
(i) preparing a reaction mixture comprising compound (I) in free base form, maleic acid and TBME; and
(ii) isolating the crystalline maleate salt from the reaction mixture.

Preferably, the process comprises agitating a mixture of compound (I) and maleic acid in TBME at ambient temperature for at least 12 hours, more preferably, at least 16 hours. Preferably, the solid so formed is filtered, washed with TBME and dried under vacuum. More preferably, the mixture is stored in a shaker during the heat/cool cycle.

Another aspect of the invention relates to a product obtainable by, or obtained by, the above process.

Crystalline Gentisate Salt (Form O)

In one preferred embodiment, the crystalline form of compound (I) is a gentisate salt.

Preferably, the crystalline form is characterized by an x-ray powder diffraction pattern having two or more diffraction peaks at 2[theta] values selected from 6.32±0.2, 12.16±0.2, 12.45±0.2, 13.13±0.2, 14.41±0.2, 14.83±0.2, 16.37±0.2, 17.12±0.2, 18.79±0.2, 19.49±0.2, 20.42±0.2, 23.37±0.2 and 2337±0.2 [Form O]. More preferably, the crystalline form is characterized by having 1, 2, 3, 4, 5, 6, 7, 8, 9, 10, 11, 12 or 13 of the aforementioned diffraction peaks.

Preferably, the crystalline form is characterized by an x-ray powder diffraction pattern in which the peak positions are substantially in accordance with the peak positions of the pattern shown in FIG. 24 or listed in Table 13.

Preferably, the crystalline form is characterized by a differential scanning calorimetry trace recorded at a heating rate of 20° C. per minute which shows a maximum endothermic peak with an onset at a temperature of about 92° C.

In one preferred embodiment, the crystalline form is characterized by a DSC/TGA trace substantially in accordance with FIG. 32.

In one preferred embodiment, the invention relates to a process for preparing the gentisate salt of compound (I) in crystalline form, said process comprising crystallizing the gentisate salt from acetonitrile.

More preferably, the invention relates to a process for preparing the gentisate salt of compound (I) in crystalline form (form O), said process comprising the steps of:
(i) preparing a reaction mixture comprising compound (I) in free base form, gentisic acid and ethyl acetate; and
(ii) isolating the gentisate salt of compound (I) from the reaction mixture;
(iii) crystallising the gentisate salt formed in step (ii) from acetonitrile.

Preferably, the process comprises agitating a mixture of compound (I) and gentisic acid in ethyl acetate at ambient temperature. Preferably, the mixture is then subjected to a heat/cool cycle (40° C./RT, 4 hours) for at least 24 hours, more preferably, 48 hours, even more preferably 72 hours. More preferably, the mixture is stored in a shaker during the heat/cool cycle. Preferably, the mixture is then cooled to about 5° C. for at least 24 hours, and then to about −18° C. for at least 24 hours. Preferably, the gentisate salt formed in step (ii) is dried under vacuum and then crystallised from acetonitrile. More preferably, acetonitrile is added to the gentisate salt formed in step (ii) and the mixture stored in a shaker at about 26° C. for at least 6 hours. Preferably, the mixture is then cooled to 5° C. for at least 12 or 16 hours, and then cooled to −18° C. for at least 24 hours. Preferably, the crystalline gentisate salt of formula (I) is obtained by slow evaporation of the acetonitrile.

Another aspect of the invention relates to a product obtainable by, or obtained by, the above process.

Crystalline Fumarate Salt (Form P)

In one preferred embodiment, the crystalline form of compound (I) is a fumarate salt.

Preferably, the crystalline form is characterized by an x-ray powder diffraction pattern having two or more diffraction peaks at 2[theta] values selected from 3.8±0.2, 7.7±0.2, 8.1±0.2, 8.8±0.2, 10.2±0.2, 11.3±0.2, 13.1±0.2, 15.2±0.2, 15.5±0.2, 16.5±0.2, 17.7±0.2, 19.1±0.2, 19.6±0.2, 20.0±0.2, 20.9±0.2, 21.5±0.2, 21.9±0.2, 22.7±0.2, 23.2±0.2, 23.8±0.2, 24.1±0.2, 25.0±0.2, 25.3±0.2, 26.7±0.2, 27.9±0.2 and 28.9±0.2 [Form P]. More preferably, the crystalline form is characterized by having 1, 2, 3, 4, 5, 6, 7 . . . or 26 of the aforementioned diffraction peaks.

Preferably, the crystalline form is characterized by an x-ray powder diffraction pattern in which the peak positions are substantially in accordance with the peak positions of the pattern shown in FIG. 25 or listed in Table 14.

Preferably, the crystalline form is characterized by a differential scanning calorimetry trace recorded at a heating rate of 20° C. per minute which shows a maximum endothermic peak with an onset at a temperature of about 140° C.

In one preferred embodiment, the crystalline form is characterized by a DSC/TGA trace substantially in accordance with FIG. 33.

In one preferred embodiment, the invention relates to a process for preparing the fumarate salt of compound (I) in crystalline form, said process comprising crystallizing the fumarate salt from ethyl acetate.

A further aspect of the invention relates to a process for preparing the fumarate salt of compound (I) in crystalline form, said process comprising the steps of:
(i) preparing a reaction mixture comprising compound (I) in free base form, fumaric acid and ethyl acetate; and
(ii) isolating the crystalline fumarate salt from the reaction mixture.

Preferably, the process comprises agitating a mixture of compound (I) and fumaric acid in ethyl acetate at ambient temperature and agitating for at least 12 hours, more preferably a least 16 hours. Preferably, the solid so formed is filtered, washed with ethyl acetate and dried under vacuum.

Another aspect of the invention relates to a product obtainable by, or obtained by, the above process.

Crystalline L-Malate Salt (Form Q)

In one preferred embodiment, the crystalline form of compound (I) is a L-malate salt.

Preferably, the crystalline form is characterized by an x-ray powder diffraction pattern having two or more diffraction peaks at 2[theta] values selected from 6.7±0.2, 8.6±0.2, 9.3±10.2, 11.0±10.2, 12.7±10.2, 13.6±10.2, 14.1±10.2, 15.1±10.2, 15.8±10.2, 16.5±10.2, 17.8±0.2, 18.7±0.2, 19.5±0.2, 19.8±0.2, 21.2±0.2, 22.5±0.2, 23.5±0.2, 24.9±0.2 and 25.7±0.2 [Form Q]. More preferably, the crystalline form is characterized by having 1, 2, 3, 4, 5, 6, 7 . . . or 19 of the aforementioned diffraction peaks.

Preferably, the crystalline form is characterized by an x-ray powder diffraction pattern in which the peak positions are substantially in accordance with the peak positions of the pattern shown in FIG. 26 or listed in Table 15.

Preferably, the crystalline form is characterized by a differential scanning calorimetry trace recorded at a heating rate of 20° C. per minute which shows a maximum endothermic peak with an onset at a temperature of about 81° C.

In one preferred embodiment, the crystalline form is characterized by a DSC/TGA trace substantially in accordance with FIG. 34.

In one preferred embodiment, the invention relates to a process for preparing the L-malate salt of compound (I) in crystalline form, said process comprising crystallizing the L-malate salt from ethyl acetate.

A further aspect of the invention relates to a process for preparing the L-malate salt of compound (I) in crystalline form, said process comprising the steps of:
(i) preparing a reaction mixture comprising compound (I) in free base form, L-malic acid and ethyl acetate; and
(ii) isolating the crystalline L-malate salt from the reaction mixture.

Preferably, the process comprises agitating a mixture of compound (I) and L-malic acid in ethyl acetate at ambient temperature for at least 24 hours. Preferably, the mixture is then heated to a temperature of about 40° C. and stirred for at least 1 hour, before cooling to room temperature and stirring for at least 12 hours. Preferably, the mixture is then cooled to about 5° C. for at least 72 hours, before cooling to about −18° C. for at least 30 hours. Preferably, the mixture is stirred at room temperature for 1 hour before filtering the solid so formed, washing with ethyl acetate and drying under vacuum.

Another aspect of the invention relates to a product obtainable by, or obtained by, the above process.

Crystalline L-Malate Salt (Form R)

In another preferred embodiment, the crystalline form is characterized by an x-ray powder diffraction pattern having two or more diffraction peaks at 2[theta] values selected from 6.77±0.2, 9.85±0.2, 12.19±0.2, 13.36±0.2, 13.59±0.2, 14.15±0.2, 15.88±0.2, 16.44±0.2, 17.33±0.2, 17.75±0.2, 19.73±0.2, 20.11±0.2, 20.50±0.2, 20.84±0.2, 21.30±0.2, 22.23±0.2, 23.27±0.2, 23.83±0.2, 24.19±0.2, 24.61±0.2, 25.18±0.2, 25.67±0.2, 26.03±0.2, 26.31±0.2, 26.91±0.2, 27.78±0.2, 28.76±0.2, 31.11±0.2, 32.35±0.2 and 33.24±0.2 [Form R]. More preferably, the crystalline form is characterized by having 1, 2, 3, 4, 5, 6, 7 . . . or 30 of the aforementioned diffraction peaks.

Preferably, the crystalline form is characterized by an x-ray powder diffraction pattern in which the peak positions are substantially in accordance with the peak positions of the pattern shown in FIG. 27 or listed in Table 16.

Preferably, the crystalline form is characterized by a differential scanning calorimetry trace recorded at a heating rate of 20° C. per minute which shows a maximum endothermic peak with an onset at a temperature of about 104° C.

In one preferred embodiment, the crystalline form is characterized by a DSC/TGA trace substantially in accordance with FIG. 35.

In one preferred embodiment, the invention relates to a process for preparing the L-malate salt (Form R) of compound (I) in crystalline form, said process comprising subjecting L-malate salt (Form Q) to a temperature of at least 40° C. and a relative humidity of at least 75% for 7 days.

More preferably, the invention relates to a process for preparing the L-malate salt of compound (I) (form R) in crystalline form, said process comprising the steps of:
(i) preparing a reaction mixture comprising compound (I) in free base form, L-malic acid and ethyl acetate;
(ii) isolating the crystalline L-malate salt (form Q) from the reaction mixture;
(iii) storing the crystalline L-malate salt (form Q) from step (ii) at 40° C./75% RH to form crystalline L-malate salt (form R).

Preferably, step (iii) comprises storing the crystalline hydrobromic acid salt (form J) for an extended period, more preferably, for at least 24 hours, more preferably, 48 hours, even more preferably 72 hours, more preferably for at least 7 days. The crystalline product is then filtered, washed and dried under vacuum.

Another aspect of the invention relates to a product obtainable by, or obtained by, the above process.

Therapeutic Use

Compound (I) has shown to exhibit potent inhibitory activity on cyclin dependent kinases, regulating proliferation, transcription and cytoskeletal organization and is therefore believed to be of use in the treatment of proliferative disorders (such as cancer and alopecia), immune-mediated and inflammatory disorders (such as graft-versus-host disease (GvHD), transplant rejection and psoriasis), autoimmune and autoimmune-mediated disorders (such as Hashimoto's thyroiditis, pernicious anemia, Addison's disease, type I diabetes, rheumatoid arthritis, systemic lupus erythematosus, dermatomyositis, Sjogren's syndrome, drug-induced lupus erythematosus, multiple sclerosis, myasthenia gravis, Reiter's syndrome and Grave's disease, pemphigus vulgaris), kidney disorders (such as glomerulonephritis and polycystic kidney disease), cardiovascular disorders (such as restenosis and cardiomyopathy), ophthalmic disorders (such as glaucoma, exudative age-related macular degeneration and proliferative diabetic retinopathy), neurodegenerative disorders (such as Alzheimer's disease and stroke), psychiatric disorders (such as bipolar disease), viral disorders (such as human cytomegalovirus (HCMV), herpes simplex virus type 1 (HSV-1), human immunodeficiency virus type 1 (HIV-1) and varicella zoster virus (VZV), metabolic disorders (type II diabetes, diabetic neuropathy), and respiratory disorders (idiopathic pulmonary fibrosis, cystic fibrosis and chronic obstructive pulmonary disorder).

Thus, one aspect of the invention relates to a crystalline form as described above for use in medicine.

Yet another aspect of the invention relates to a crystalline form as described above for use in the prevention or treatment of a proliferative disorder.

Another aspect of the invention relates to the use of a crystalline form as described above in the preparation of a medicament for the prevention or treatment of a proliferative disorder.

Another aspect of the invention relates to a method for the prevention or treatment of a proliferative disorder, said method comprising administering a pharmacologically effective amount of a crystalline form as described above to a subject in need thereof. Preferably, the subject is a warm blooded animal, more preferably still, a human.

As used herein the phrase "preparation of a medicament" includes the use of one or more of the above described forms directly as the medicament in addition to their use in a screening programme for further antiproliferative agents or in any stage of the manufacture of such a medicament.

As defined herein, an anti-proliferative effect within the scope of the present invention may be demonstrated by the ability to inhibit cell proliferation in an in vitro whole cell assay. Using such assays it may be determined whether a compound is anti-proliferative in the context of the present invention.

One preferred embodiment relates to the use of one or more compounds of the invention in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, genetic proliferative diseases such as polycystic kidney disease, In one preferred embodiment, the proliferative disorder is a solid tumour.

In another preferred embodiment, the proliferative disorder is a haematological cancer. Preferably, the haematological cancer is leukaemia, more preferably, advanced leukaemias or myelodysplastic syndromes (MDS). Other examples include acute myelogenous leukaemia (AML), acute lymphocytic leukaemia (ALL) or chronic lymphocytic leukaemia (CLL).

In another preferred embodiment, the proliferative disorder is selected from glomerulonephritis, rheumatoid arthritis, psoriasis and chronic obstructive pulmonary disorder.

The compounds of the invention are also useful in the preparation of medicaments for the treatment of various ophthalmic disorders. Preferably, the ophthalmic disorder is glaucoma, exudative age-related macular degeneration (AMD) or proliferative diabetic retinopathy (PDR).

Pharmaceutical Composition

When crystalline forms of the invention are used as a medicament, preferably as an agent for treatment or prevention of proliferative disorders, the crystalline form can be administered alone, or as a mixture of the crystalline form with an appropriate pharmacologically acceptable excipient(s), and/or diluent(s) and/or carrier(s).

Another aspect of the invention therefore relates to a pharmaceutical composition comprising a crystalline form according as described above and a pharmaceutically acceptable diluent, excipient or carrier.

Compositions according to the present invention can be in unit dosage form such as tablets, capsules, granules, powders, syrups, injections, ointments, solutions, suspensions, aerosols, troches or the like for oral, topical (e.g. for psoriasis) or parenteral administration.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). The pharmaceutical compositions may be for human or animal usage in human and veterinary medicine.

The pharmaceutical compositions can be prepared in a known manner by using additives such as excipients, binding agents, disintegrating agents, lubricating agents, stabilizing agents, corrigents, suspending agents, diluents and solvents.

Examples of such suitable excipients for the various different forms of pharmaceutical compositions described herein may be found in the "Handbook of Pharmaceutical Excipients, $2^{nd}$ Edition, (1994), Edited by A Wade and P J Weller. An example of an excipient includes a sugar derivative such as lactose, sucrose, glucose, mannitol, or sorbitol; a starch derivative such as corn starch, potato starch, alpha-starch, dextrin, carboxy methylstarch; a cellulose derivative such as crystalline cellulose, low-substituted hydroxypropylcellulose, hydroxypropylmethylcellulose, carboxymethylcellulose, calcium carboxymethylcellulose, internal-cross-linked sodium carboxymethylcellulose; acacia; dextran; pullulan; a silicate derivative such as light silicic acid anhydride, synthetic aluminum silicate, magnesium aluminate metasilicate; a phosphate derivative such as calcium phosphate; a carbonate derivative such as calcium carbonate; a sulfate derivative such as calcium sulfate; or the like.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

An example of a disintegrating agent includes an excipient described hereinbefore, a chemically modified starch or cellulose derivative such as sodium cross-carmellose, sodium carboxymethylstarch, cross-linked polyvinylpyrrolidone or the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

An example of a stabilizing agent includes a para-hydroxybenzoic acid ester derivative such as methylparabene, propylparabene; an alcohol derivative such as chlorobutanol, benzyl alcohol, phenetyl alcohol; benzalkonium chloride; a phenol derivative such as phenol, cresol; thimerosal; acetic anhydride; sorbic acid; or the like. An example of a corrigent includes a sweetening, souring, and flavoring agents or the like all of which are ordinarily used.

An example of a solvent includes water, ethanol, glycerin or the like.

Examples of suitable binders include an excipient described hereinbefore; gelatin; polyvinylpyrrolidone; macrogol; or the like, starch, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

An example of a lubricating agent includes talc; stearic acid; a metal stearate derivative such as calcium stearate, magnesium stearate, sodium stearate; colloidal silica; veegum; a wax such as beeswax or spermaceti; boric acid; a glycol; a carboxy acid derivative such as fumaric acid, adipic acid; a sodium carboxylate such as sodium benzoate; a sulfate such as sodium sulfate; leucine; a lauryl sulfate such as sodium lauryl sulfate, or magnesium lauryl sulfate; a silicic acid derivative such as silicic acid anhydride, silicic acid hydrate; a starch derivative described above as an excipient; sodium oleate, sodium acetate, sodium chloride, or the like.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

The dose of the crystalline form of compound (I) will depend on such factors as symptom, body weight and age of the patient. A suitable dosage level is 0.1 mg (preferably 1 mg) per day to 100 mg (preferably 50 mg) per day. The crystalline form of the compound of formula (I) can be administered as either a single unit dosage, or if desired, the dosage may be divided into convenient subunits administered at one to several times throughout the day depending on the symptoms of the patient.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The present invention is further described with reference to the following figures, wherein.

Figures 5, 6:
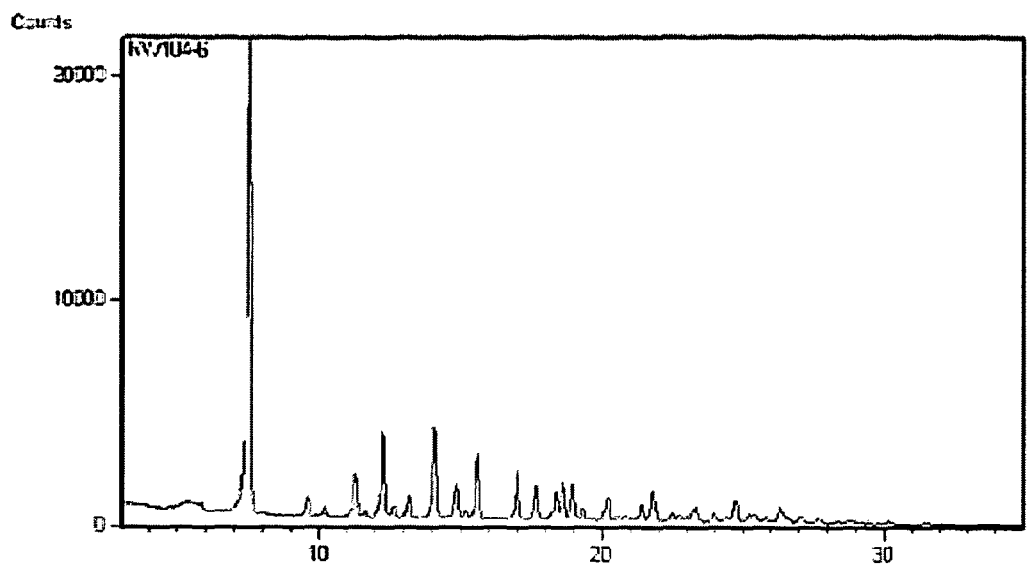
FIG. 5 shows the X-ray powder diffraction pattern of crystalline free base (Form A) of compound (I) as obtained by Example 1. The diffraction pattern was obtained by irradiation of the crystalline product using a PANalytical diffractometer.

FIG. 6 shows a DSC thermogram (lower trace) of crystalline free base (Form A) of compound (I) as obtained by Example 1, using a PerkinElmer Pyris 6 at a heating rate of 20° C. min$^{-1}$ (peak max is observed at 137.63° C.). The upper trace shows TGA for the same salt measured using a Pyris 1 TGA at a heating rate of 20° C. min$^{-1}$. No significant mass loss was observed up to 250° C., onset observed at 369.39° C.

Figure 7:
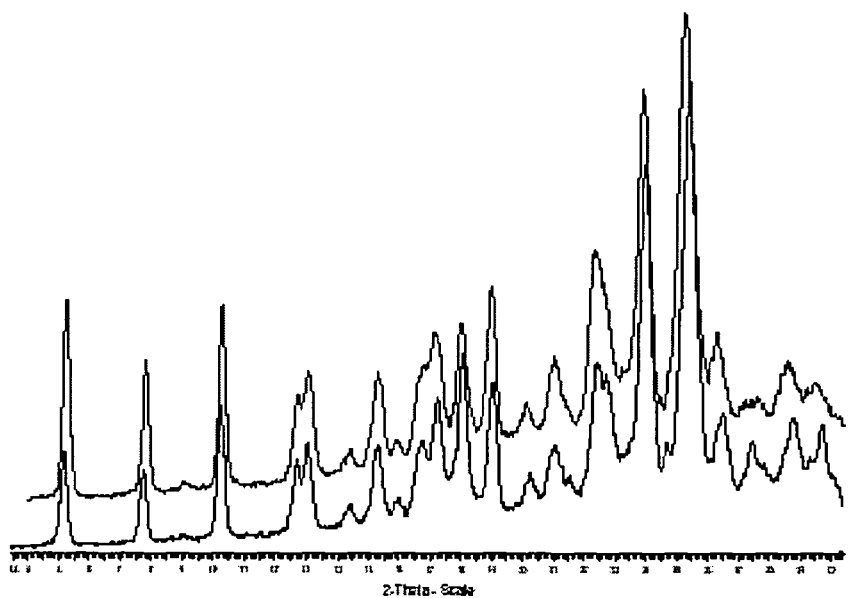

FIG. 7 shows the X-ray powder diffraction pattern of the citrate salt (Form F) of compound (I) as obtained by Example 2. The diffraction pattern was obtained by irradiation of the crystalline product using Bruker AXS C2 GADDS.

Figure 8:
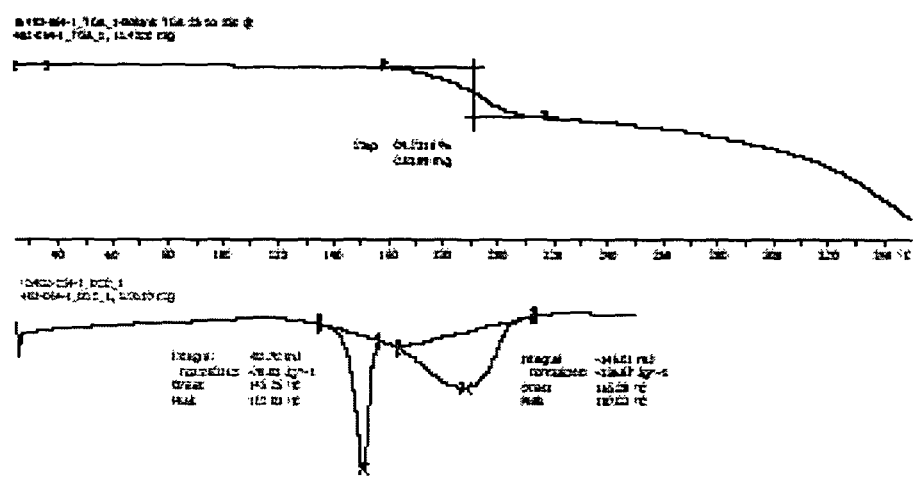

FIG. 8 shows a DSC thermogram (lower trace) of the citrate salt (Form F) of compound (I) as obtained by Example 2, using Mettler DSC823e at a heating rate of 10° C. min$^{-1}$ (peak max observed at 150.83° C. and 187.83). The upper trace shows TGA analysis for the same salt using a Mettler TGA/SDTA 851e at a heating rate of 10° C. min$^{-1}$.

Figure 9:
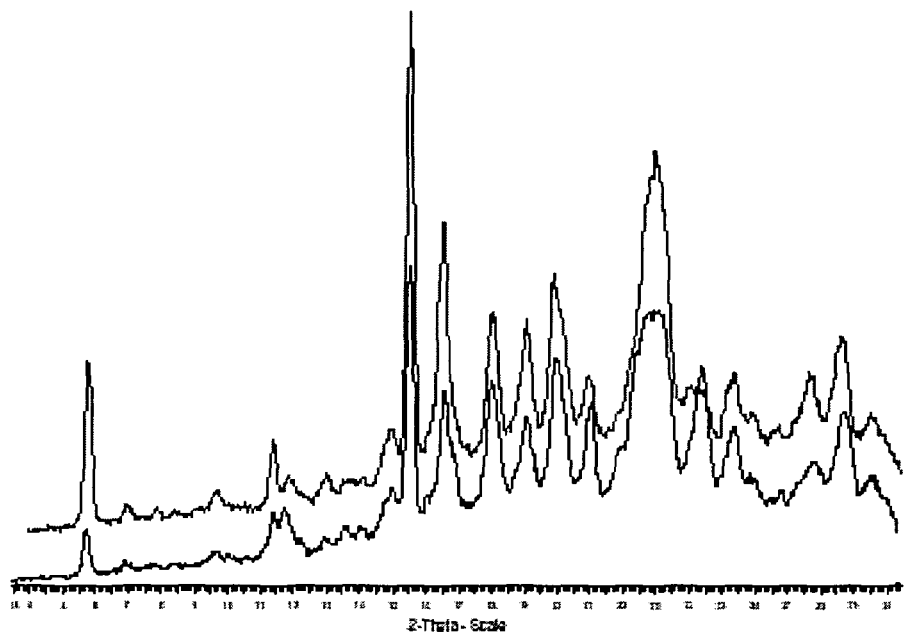

FIG. 9 shows the X-ray powder diffraction pattern of the benzenesulfonic acid salt (Form G) of compound (I) as obtained by Example 3. The diffraction pattern was obtained by irradiation of the crystalline product using Bruker AXS C2 GADDS.

Figure 10:
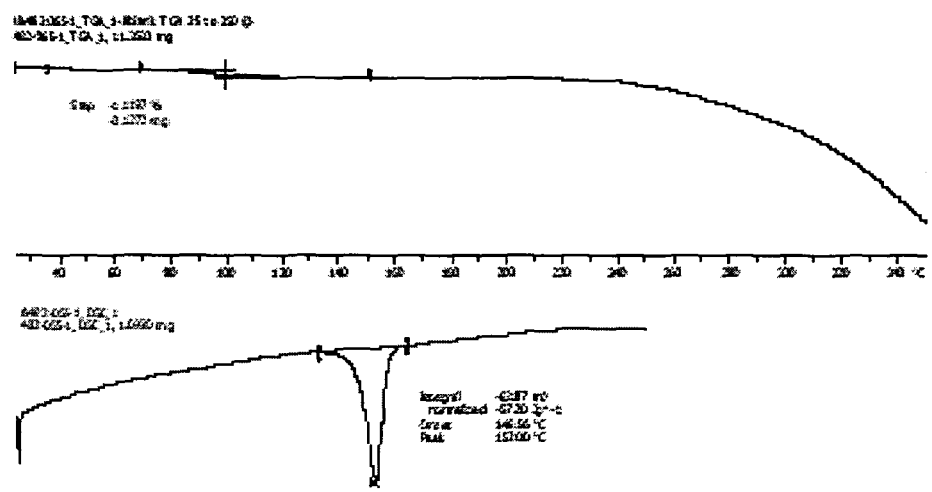

FIG. 10 shows a DSC thermogram (lower trace) of the benzenesulfonic acid salt (Form G) of compound (I) as obtained by Example 3, using Mettler DSC823e at a heating rate of 10° C. min$^{-1}$ (peak max observed at 153.00). The upper trace shows TGA analysis for the same salt using a Mettler TGA/SDTA 851e at a heating rate of 10° C. min$^{-1}$.

Figure 11:
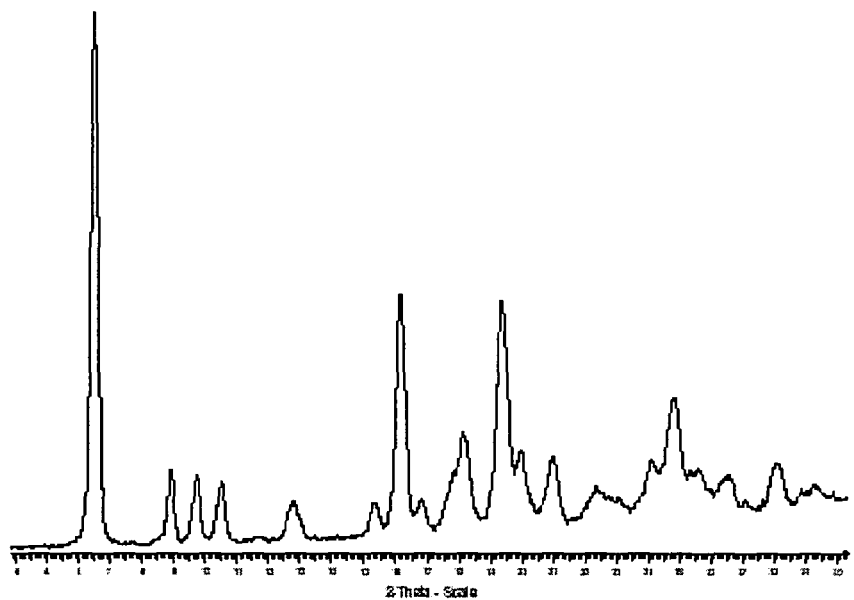

FIG. 11 shows the X-ray powder diffraction pattern of the phosphate salt (Form B) of compound (I) as obtained by Example 7. The diffraction pattern was obtained by irradiation of the crystalline product Bruker AXS C2 GADDS.

Figure 12:
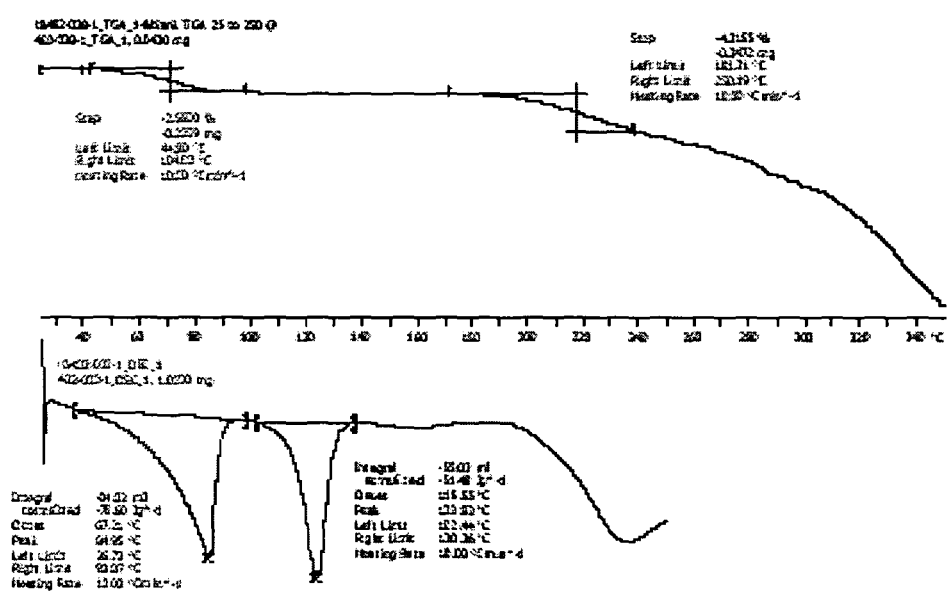

FIG. 12 is a DSC thermogram (lower trace) of Form 1 the phosphate salt (Form B) of compound (I) as obtained by Example 7, using Mettler DSC823e at a heating rate of 10° C. min$^{-1}$ (peak max observed at 84.95 and 123.93). The upper trace shows TGA analysis for the same salt using a Mettler TGA/SDTA 851e with a heating rate of 10° C. min$^{-1}$.

Figure 13:
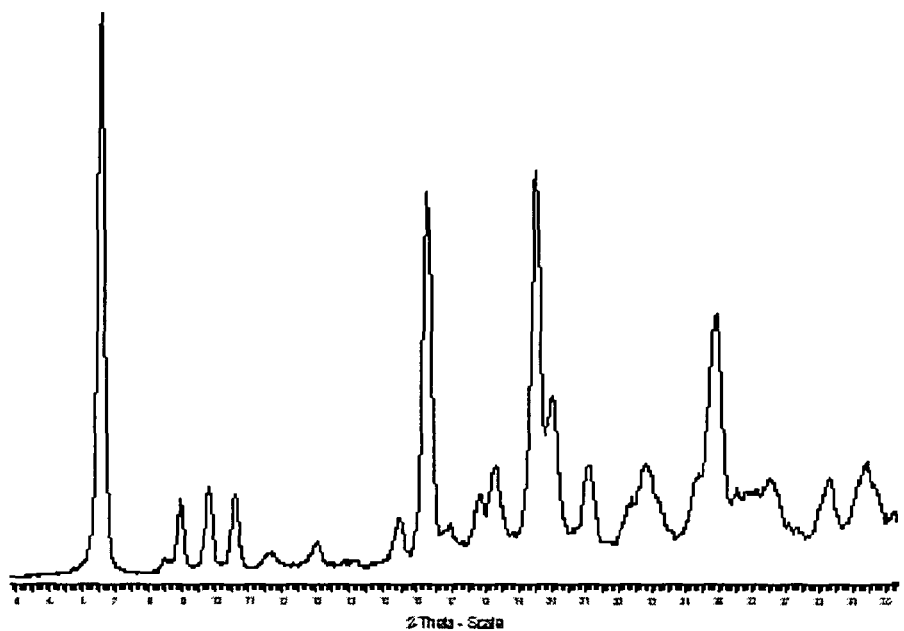

FIG. 13 shows the X-ray powder diffraction pattern of the phosphate salt (Form C) of compound (I) as obtained by Example 6. The diffraction pattern was obtained by irradiation of the crystalline product using Bruker AXS C2 GADDS.

Figure 14:
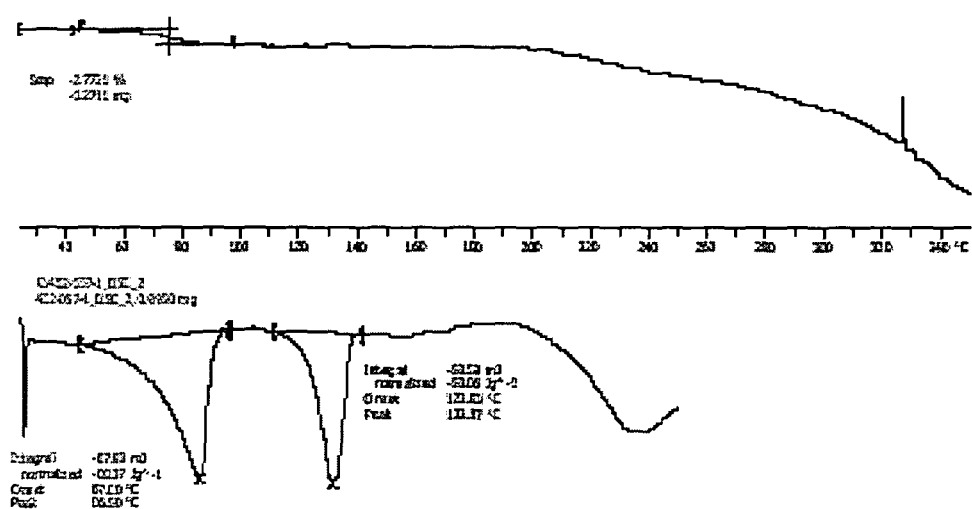

FIG. 14 is a DSC thermogram of Form 2 of the phosphate salt (Form C) of compound (I) as obtained by Example 6, using Mettler DSC823e at a heating rate of 10° C. min$^{1}$ (peak max observed at 86.50 and 132.17). The upper trace shows TGA analysis for the same salt using a Mettler TGA/SDTA 851e with a heating rate of 10° C. min$^{-1}$.

Figure 15:
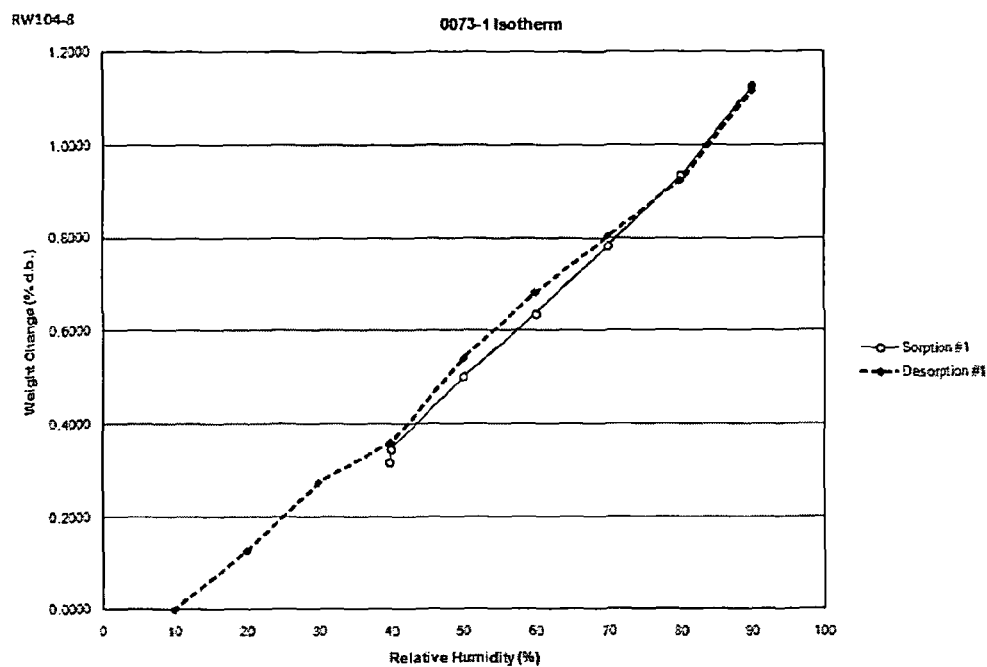

FIG. 15 shows an isotherm plot for Form A (weight change % vs RH %) as measured using a Hiden Isochema moisture sorption analyser.

Figure 16:
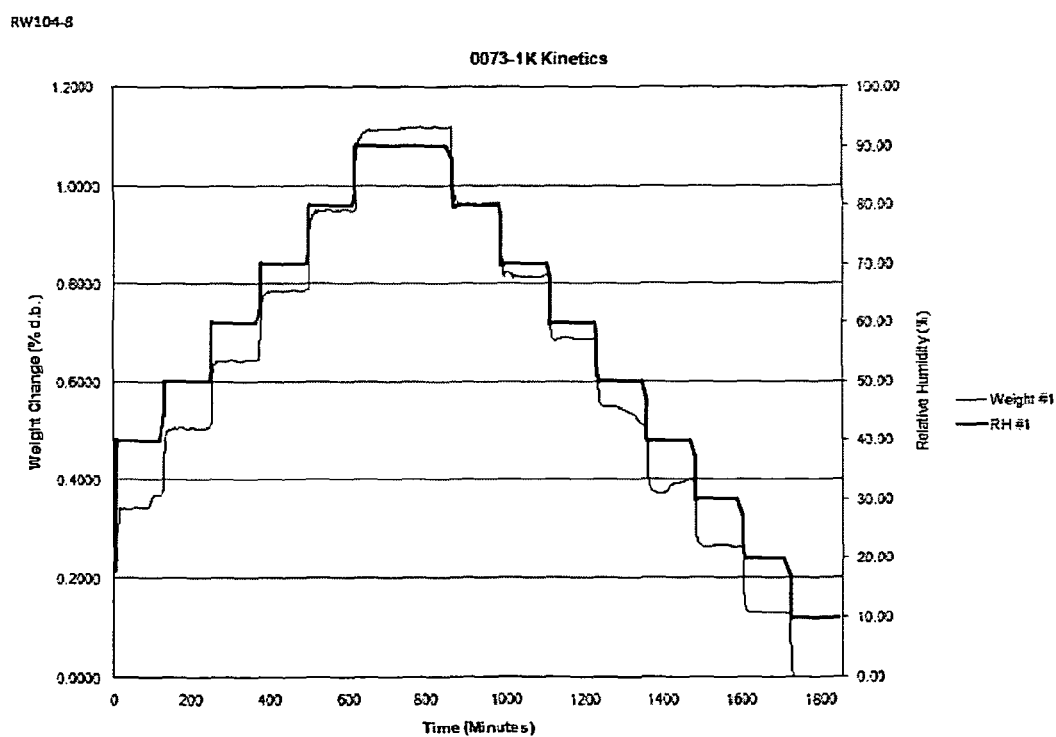

FIG. 16 shows a kinetic plot of weight change (%) of Form A vs time and relative humidity %.

Figure 17:
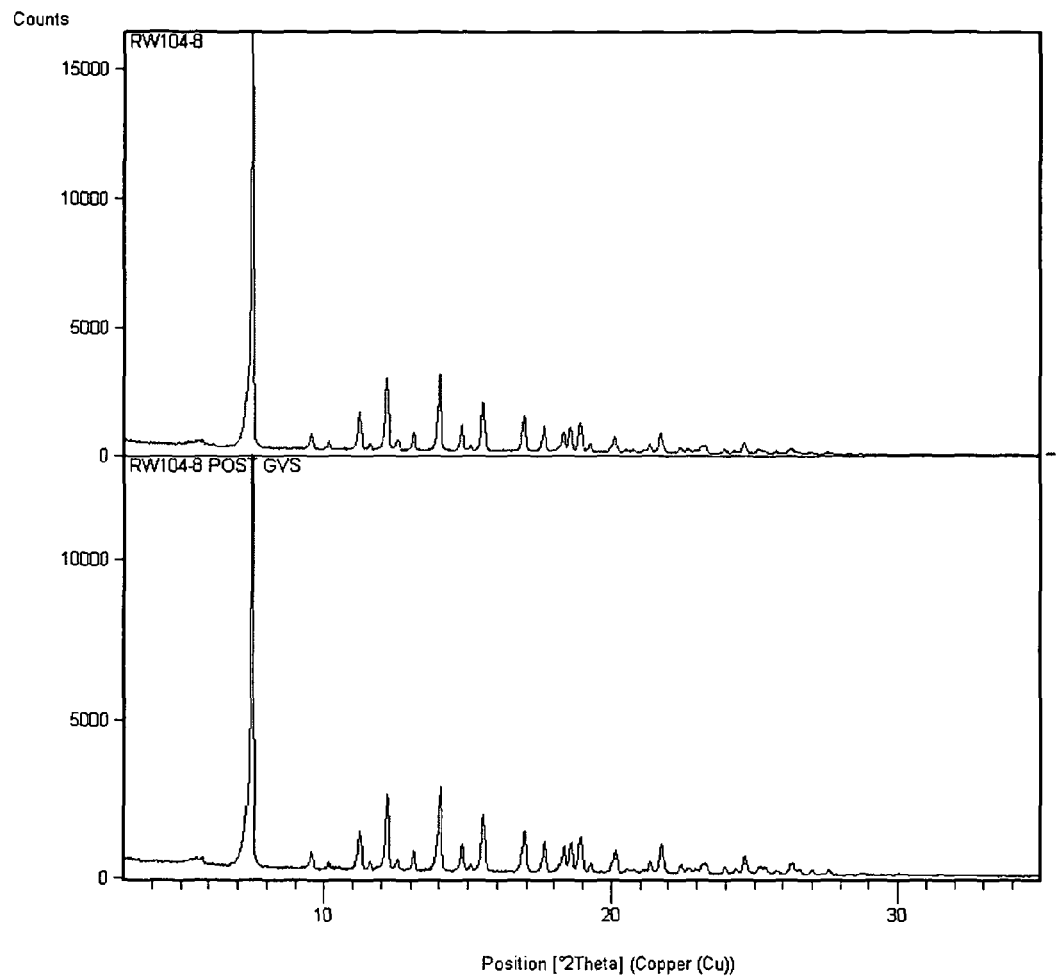

FIG. 17 shows XRPD analysis of Form A post GVS.

Figure 18:
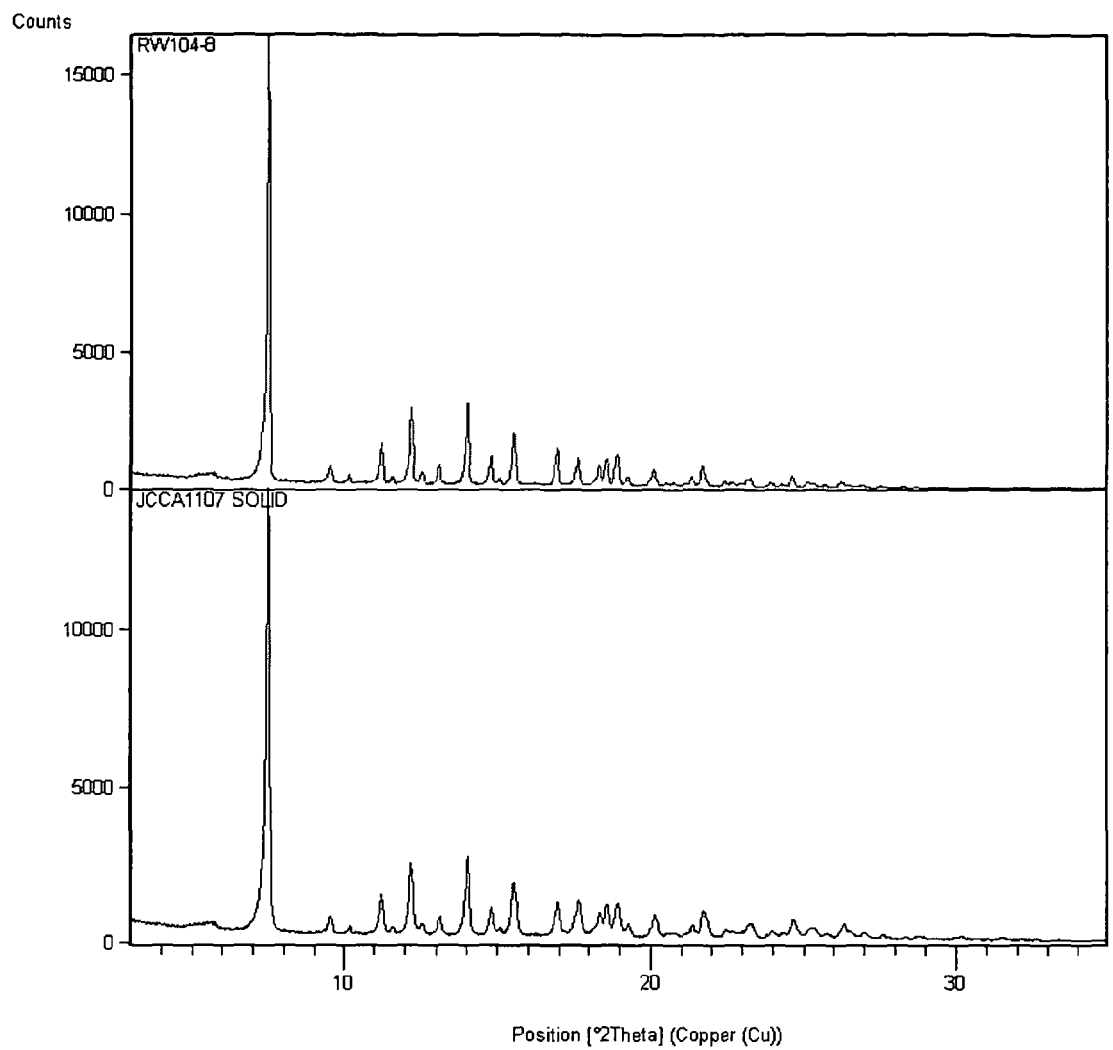

FIG. 18 shows XRPD analysis of Form A pre and post solubility study.

Figure 19:
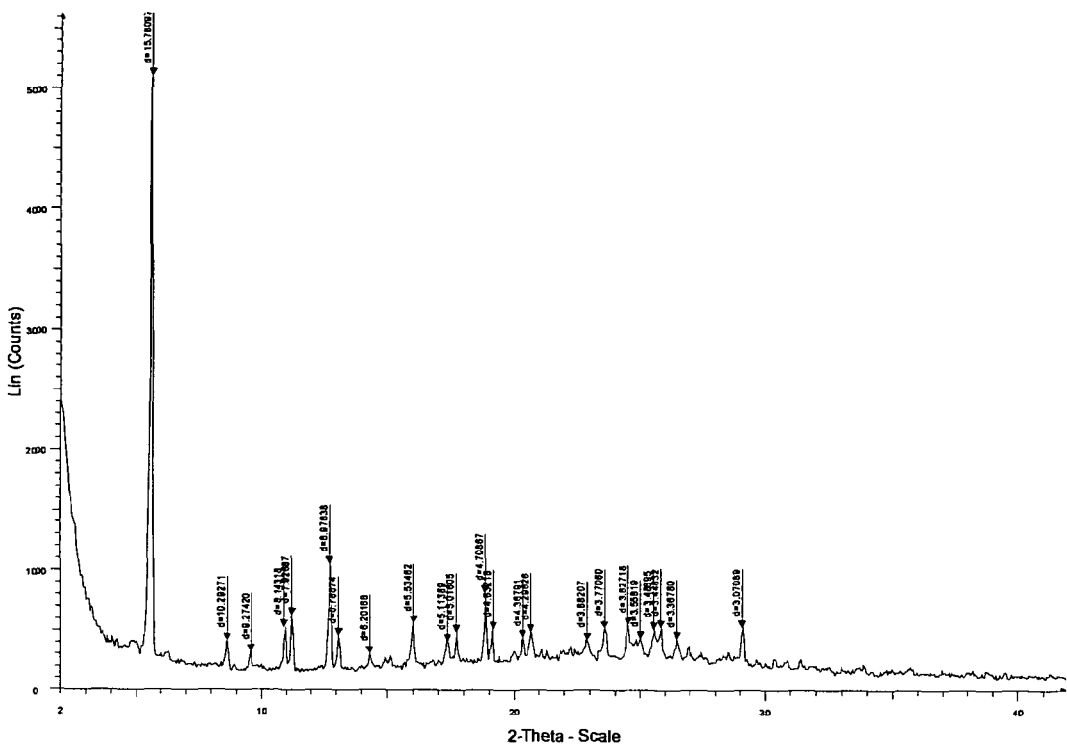

FIG. 19 shows the X-ray powder diffraction pattern of the hydrochloride salt (Form H) of compound (I) as obtained by Example 8. The diffraction pattern was obtained by irradiation of the crystalline product using Bruker AXS D8 Advance.

Figure 20:
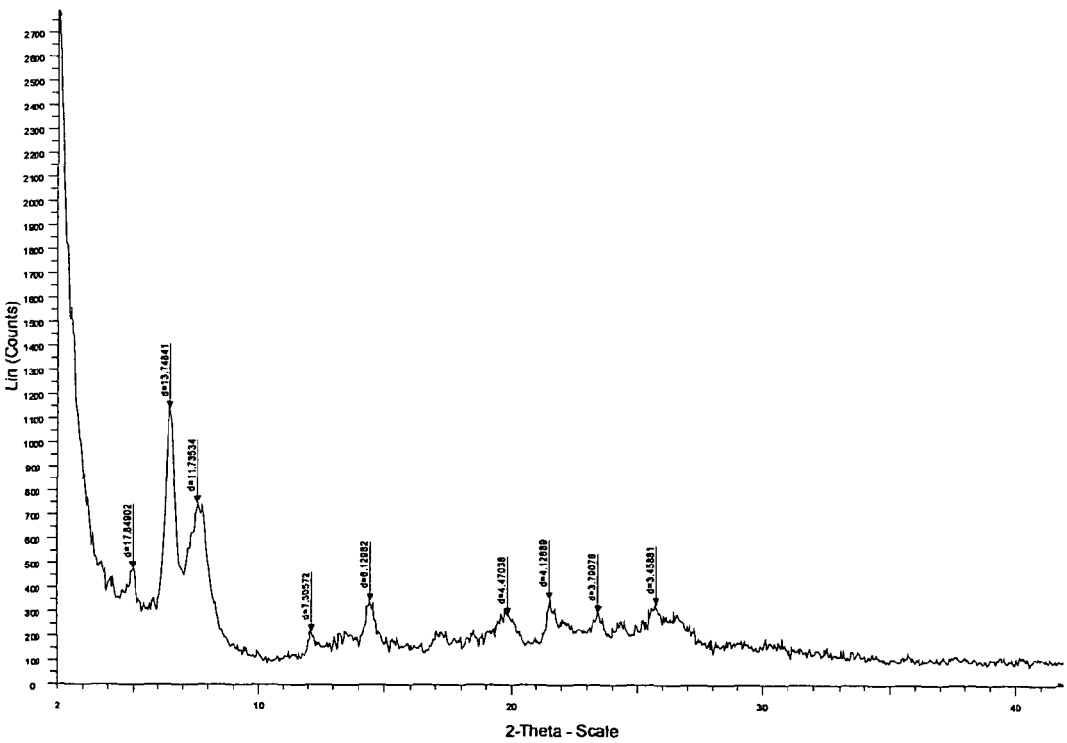

FIG. 20 shows the X-ray powder diffraction pattern of the hydrochloride salt (Form I) of compound (I) as obtained by Example 9. The diffraction pattern was obtained by irradiation of the crystalline product using Bruker AXS D8 Advance.

Figure 21:
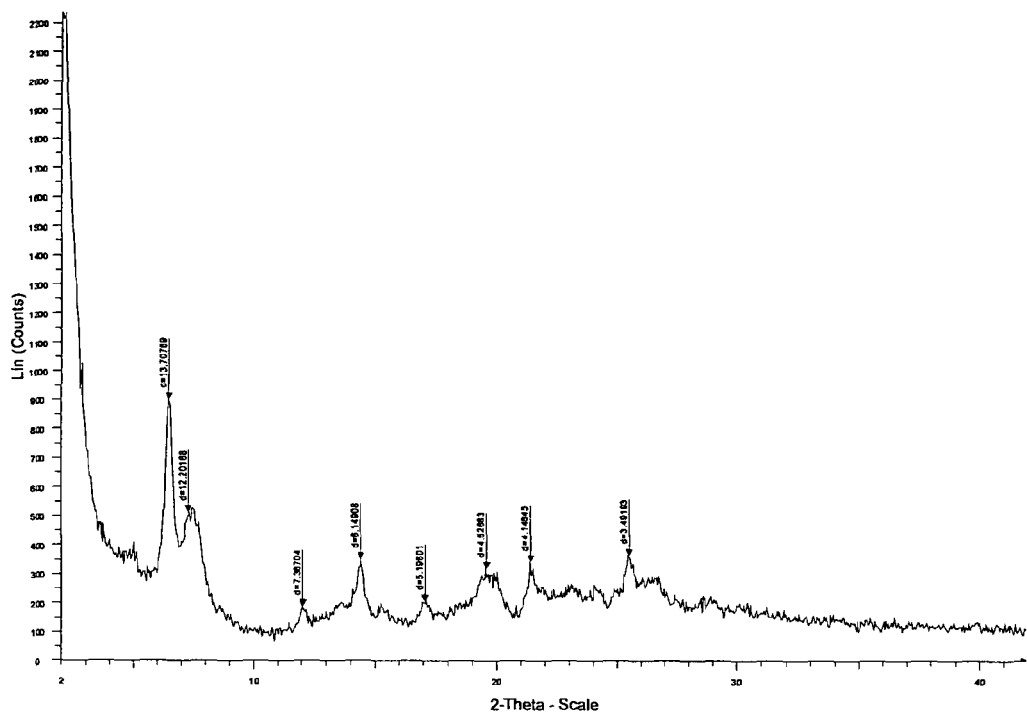

FIG. 21 shows the X-ray powder diffraction pattern of the hydrobromide salt (Form J) of compound (I) as obtained by Example 10. The diffraction pattern was obtained by irradiation of the crystalline product using Bruker AXS D8 Advance.

Figure 22:
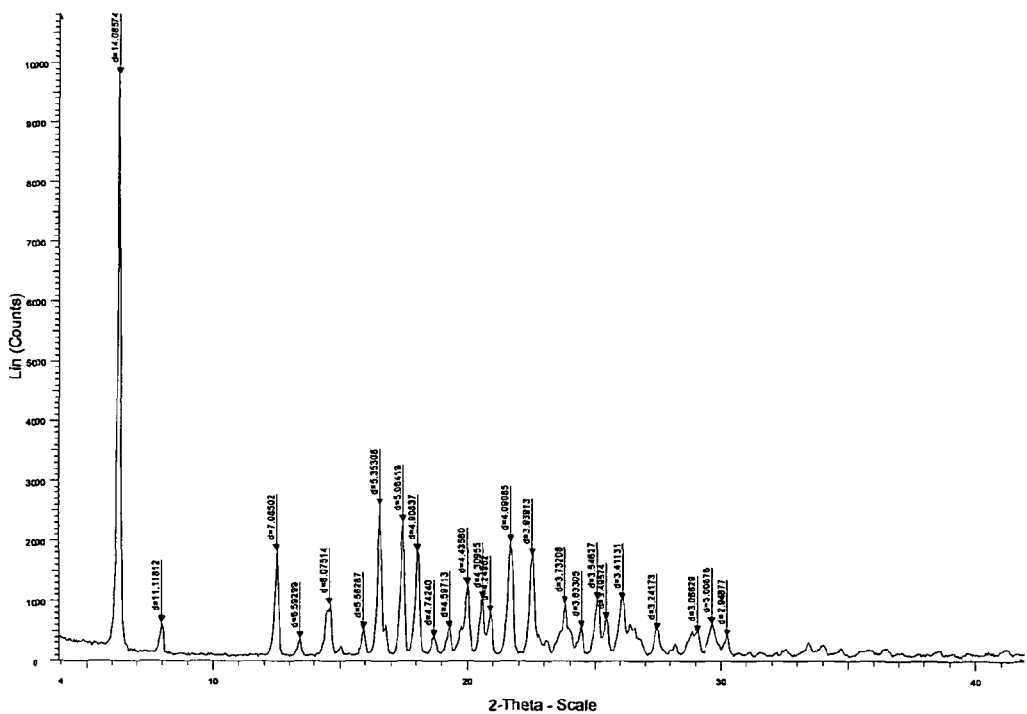

FIG. 22 shows the X-ray powder diffraction pattern of the mesylate salt (Form L) of compound (I) as obtained by Example 12. The diffraction pattern was obtained by irradiation of the crystalline product using Bruker AXS D8 Advance.

Figure 23:
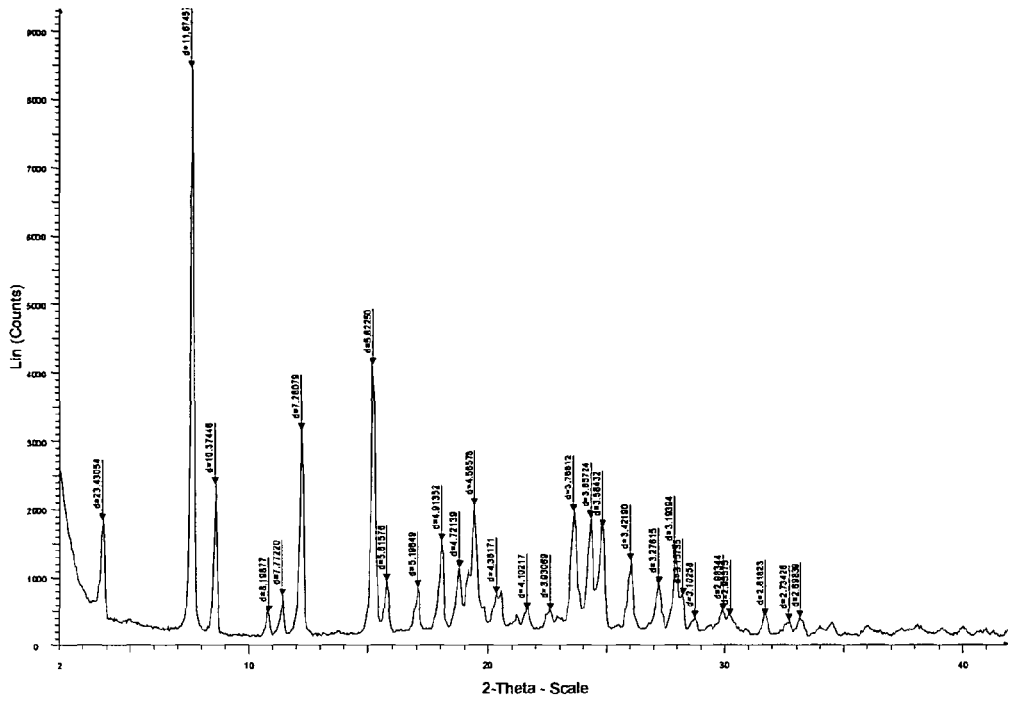

FIG. 23 shows the X-ray powder diffraction pattern of the maleate salt (Form M) of compound (I) as obtained by Example 13. The diffraction pattern was obtained by irradiation of the crystalline product using Bruker AXS D8 Advance.

Figure 24:
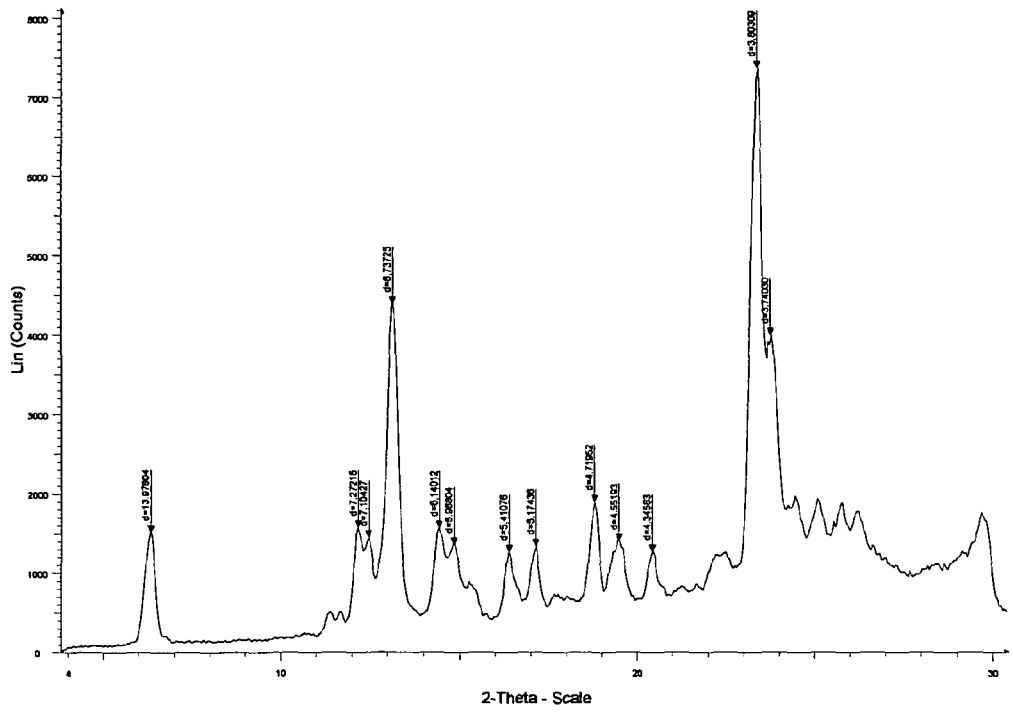

FIG. 24 shows the X-ray powder diffraction pattern of the gentisate salt (Form O) of compound (I) as obtained by Example 15. The diffraction pattern was obtained by irradiation of the crystalline product using Bruker AXS D8 Advance.

Figure 25:
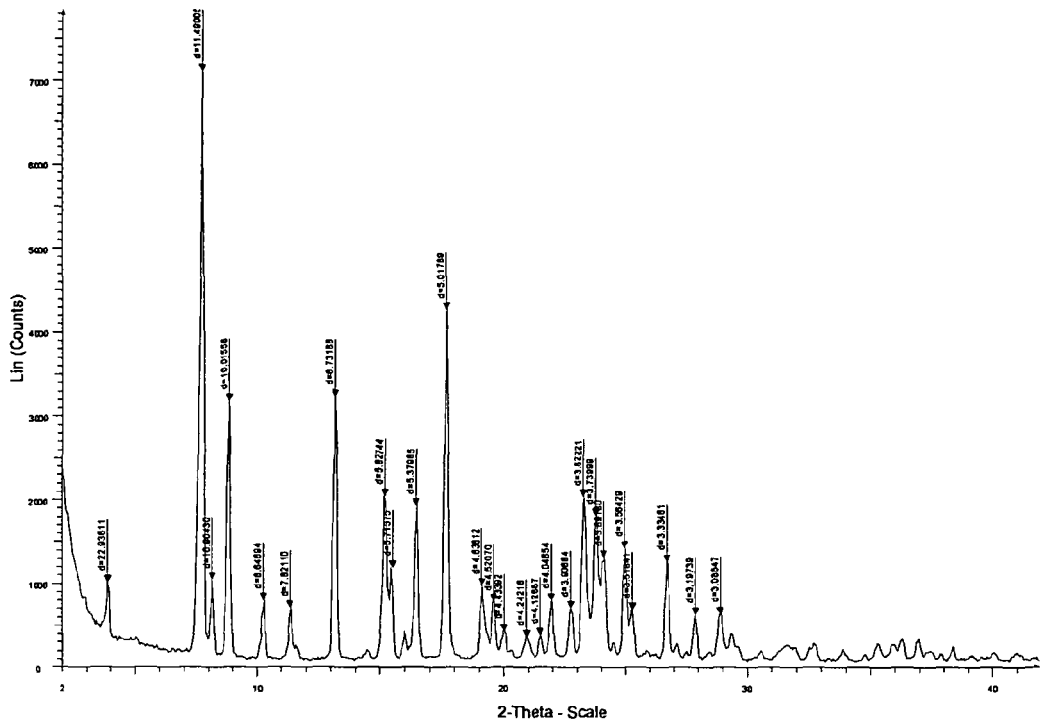

FIG. 25 shows the X-ray powder diffraction pattern of the fumarate salt (Form P) of compound (I) as obtained by Example 16. The diffraction pattern was obtained by irradiation of the crystalline product using Bruker AXS D8 Advance.

Figure 26:
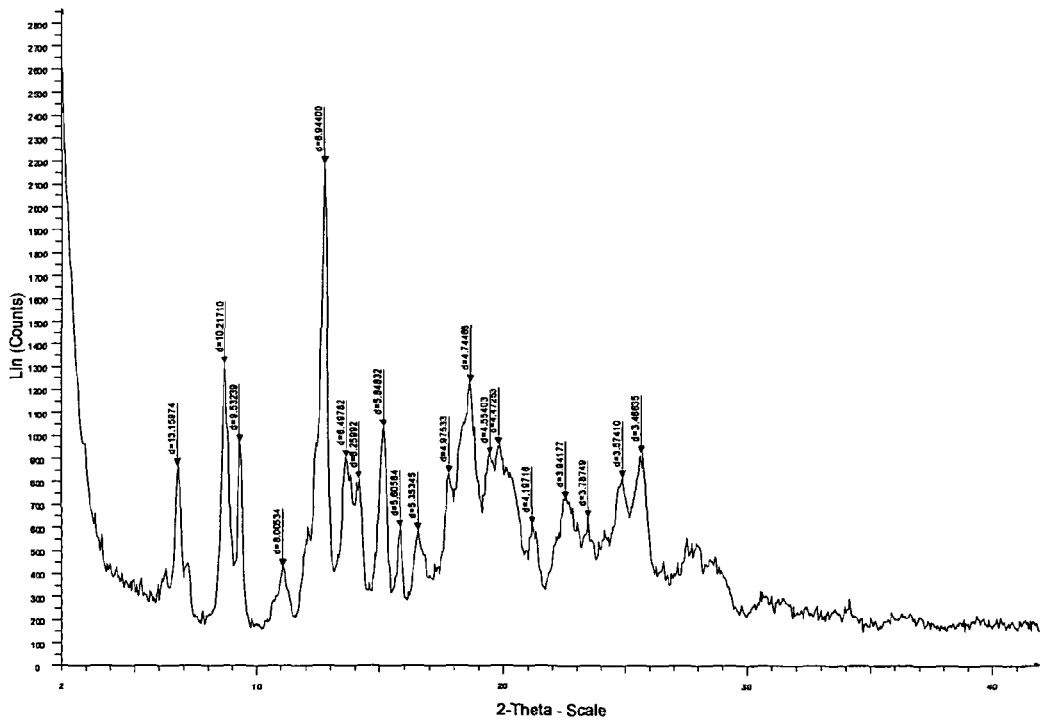

FIG. 26 shows the X-ray powder diffraction pattern of the L-malate salt (Form Q) of compound (I) as obtained by Example 17. The diffraction pattern was obtained by irradiation of the crystalline product using Bruker AXS D8 Advance.

Figure 27:
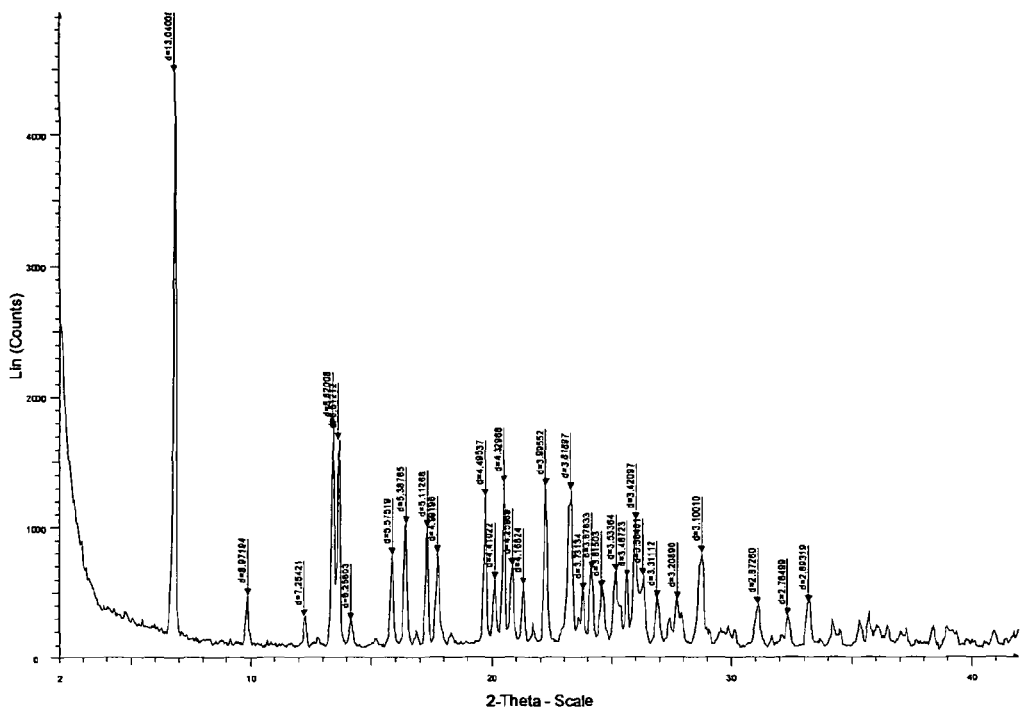

FIG. 27 shows the X-ray powder diffraction pattern of the L-malate salt (Form R) of compound (I) as obtained by Example 18. The diffraction pattern was obtained by irradiation of the crystalline product using Bruker AXS D8 Advance.

Figure 28:
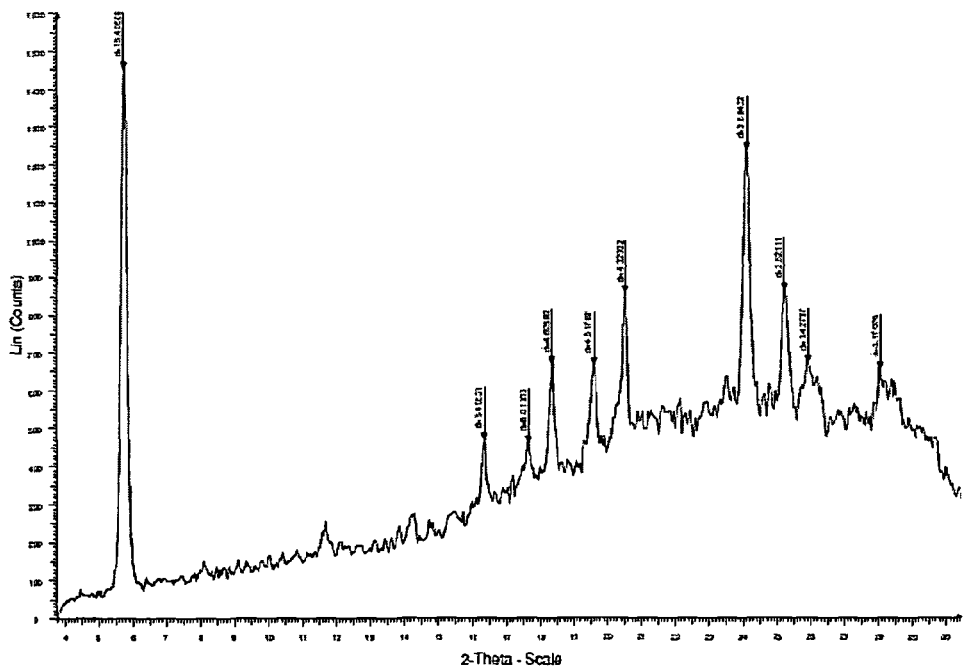

FIG. 28 shows the X-ray powder diffraction pattern of the bromide salt (Form K) of compound (I) as obtained by Example 11. The diffraction pattern was obtained by irradiation of the crystalline product using Bruker AXS D8 Advance.

Figure 29:
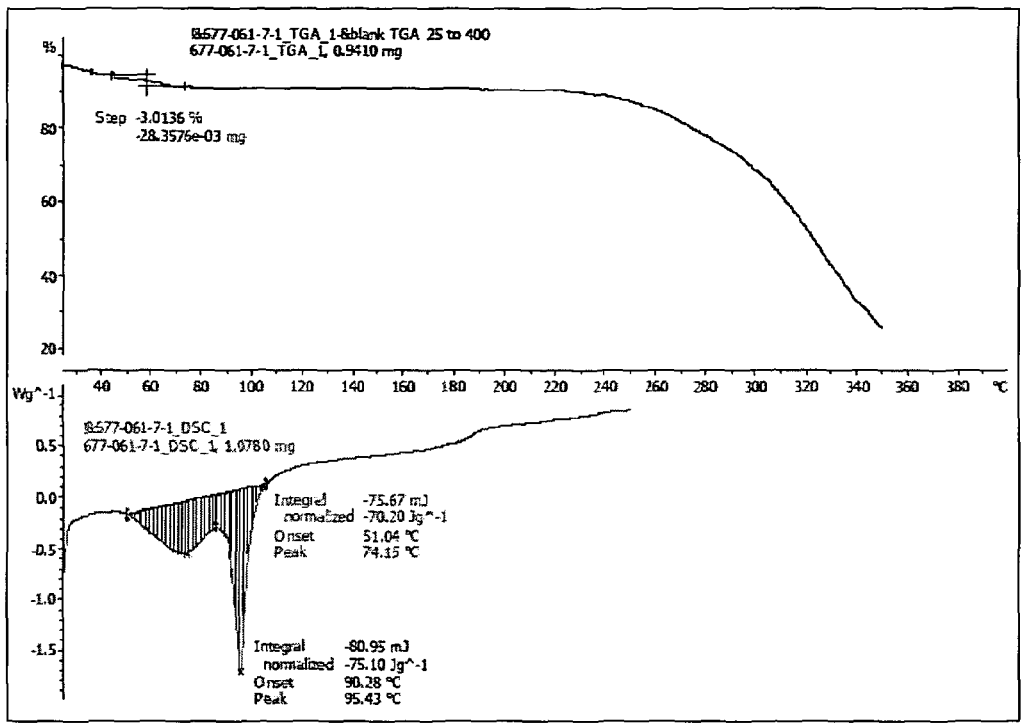

FIG. 29 shows a DSC thermogram (lower trace) of the HBr salt Form K of compound (I) as obtained by Example 11, using Mettler DSC823e at a heating rate of 10° C. min$^{-1}$ (peak max observed at 74 and 95° C.). The upper trace shows TGA analysis for the same salt using a Mettler TGA/SDTA 851e at a heating rate of 10° C. min$^{-1}$.

Figure 30:
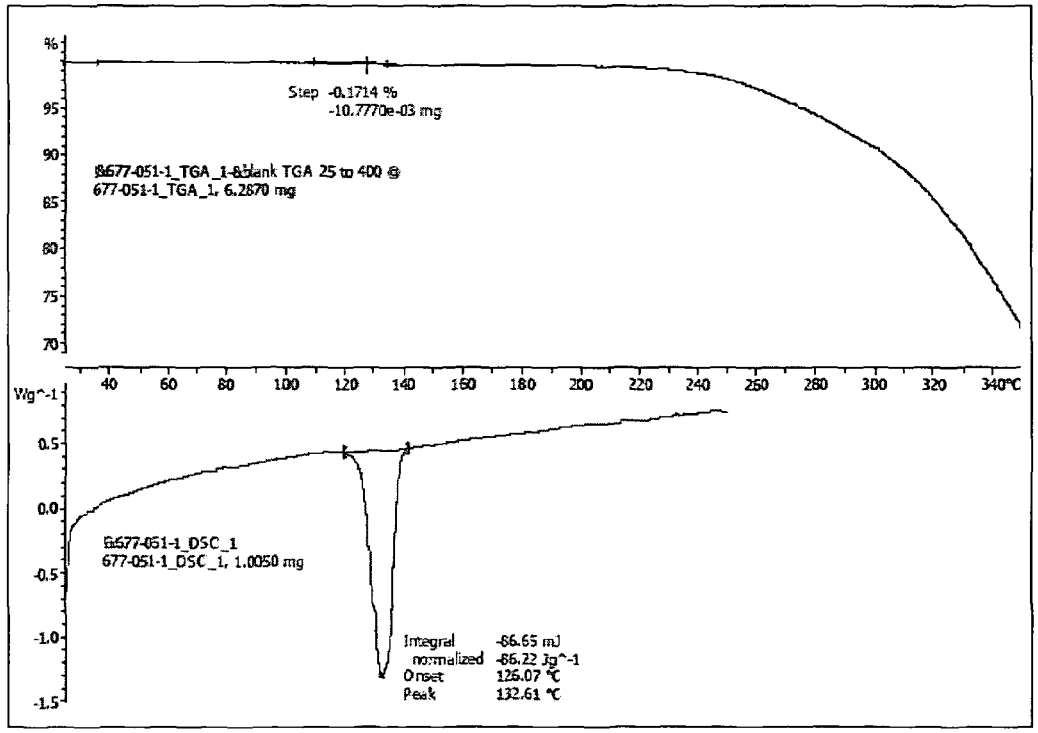

FIG. 30 shows a DSC thermogram (lower trace) of the mesylate salt Form L of compound (I) as obtained by Example 12, using Mettler DSC823e at a heating rate of 10° C. min$^{-1}$ (peak max observed at 132° C.). The upper trace shows TGA analysis for the same salt using a Mettler TGA/SDTA 851e at a heating rate of 10° C. min$^{-1}$.

Figure 31:
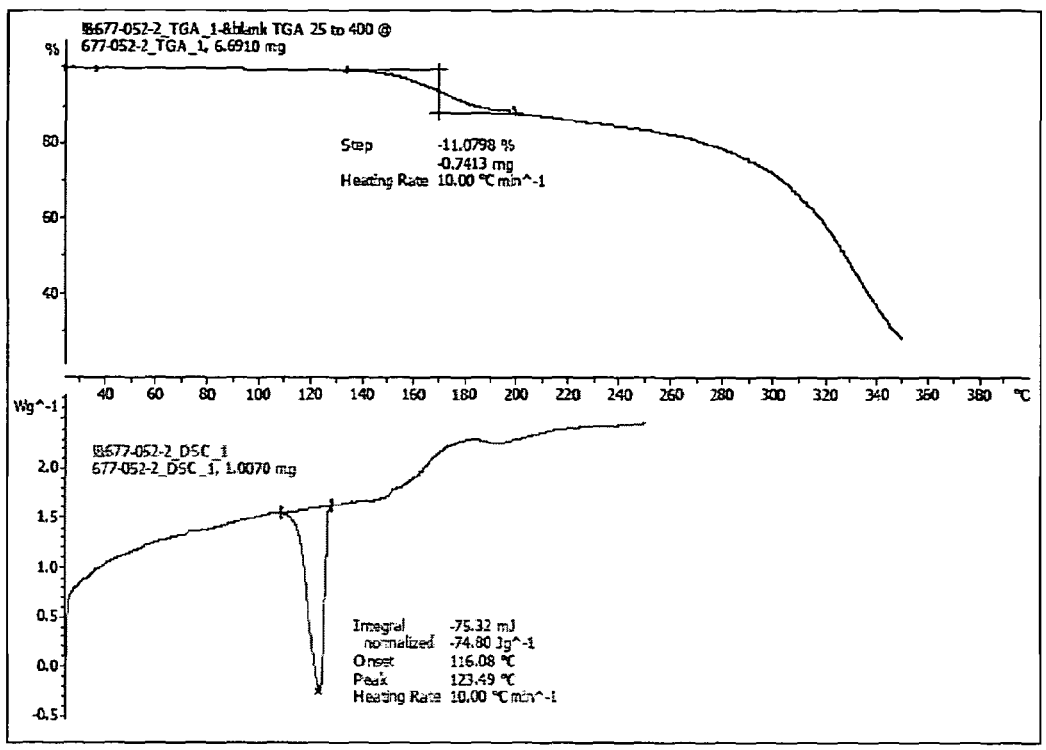

FIG. 31 shows a DSC thermogram (lower trace) of the maleate salt Form M of compound (I) as obtained by Example 13, using Mettler DSC823e at a heating rate of 10° C. min$^{-1}$ (peak max observed at 123° C.). The upper trace shows TGA analysis for the same salt using a Mettler TGA/SDTA 851e at a heating rate of 10° C. min$^{-1}$.

Figure 32:
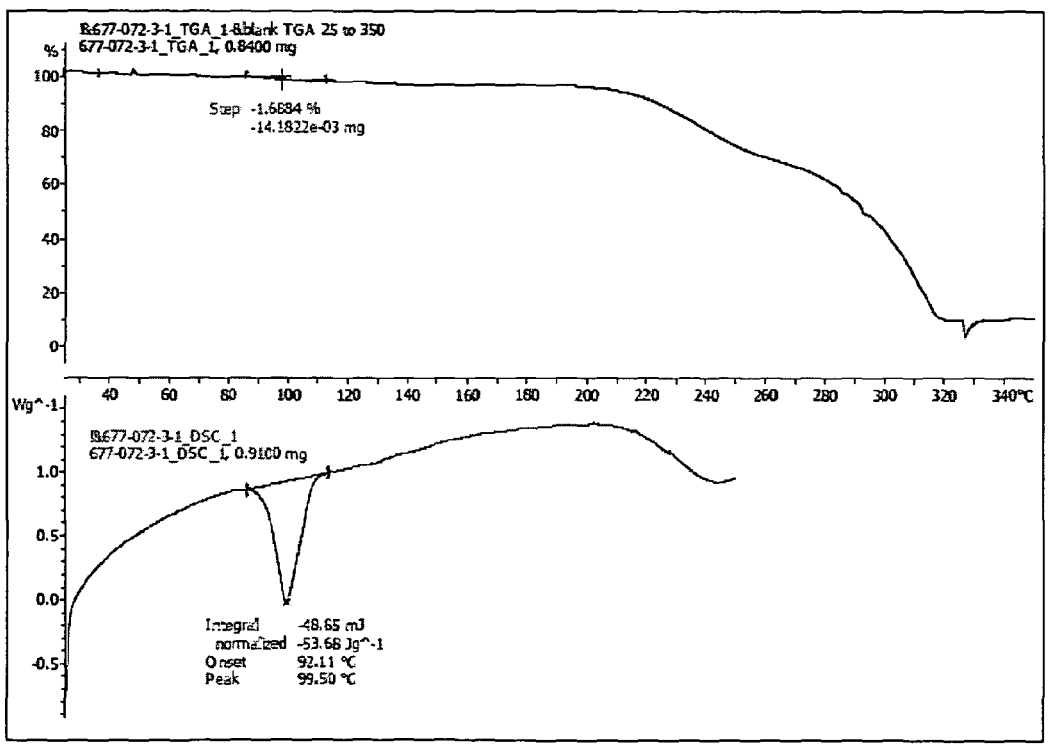

FIG. 32 shows a DSC thermogram (lower trace) of the gentisate salt Form 0 of compound (I) as obtained by Example 15, using Mettler DSC823e at a heating rate of 10° C. min$^{-1}$ (peak max observed at 99° C.). The upper trace shows TGA analysis for the same salt using a Mettler TGA/SDTA 851e at a heating rate of 10° C. min$^{-1}$.

Figure 33:
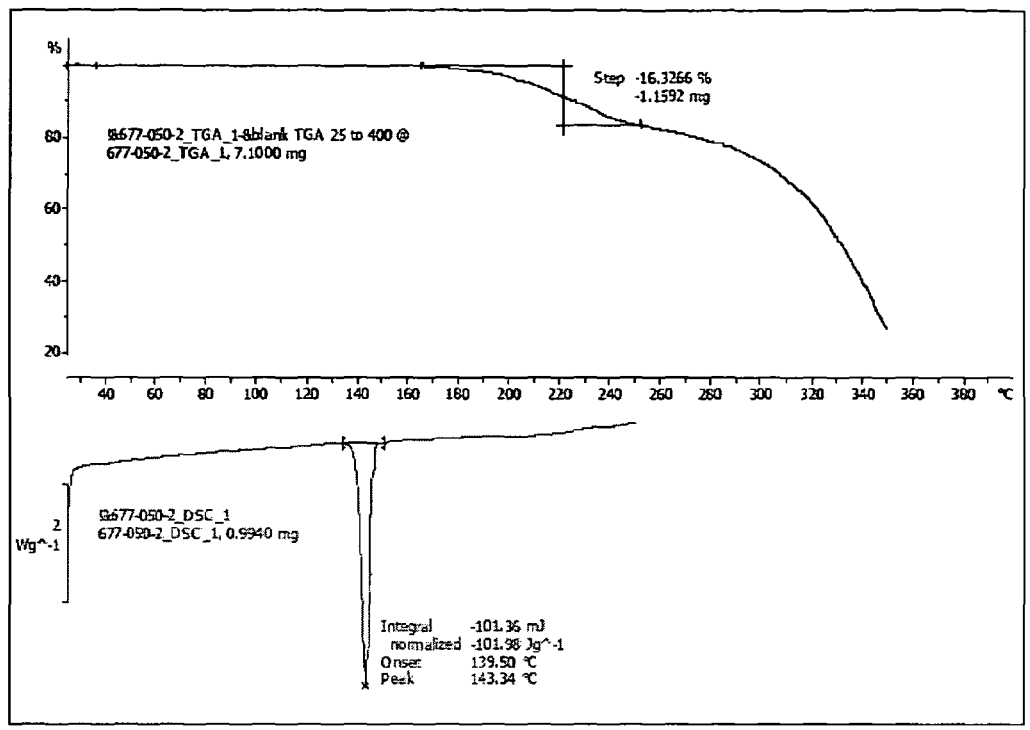

FIG. 33 shows a DSC thermogram (lower trace) of the fumarate salt Form P of compound (I) as obtained by Example 16, using Mettler DSC823e at a heating rate of 10° C. min$^{-1}$ (peak max observed at 143° C.). The upper trace shows TGA analysis for the same salt using a Mettler TGA/SDTA 851e at a heating rate of 10° C. min$^{-1}$.

Figure 34:
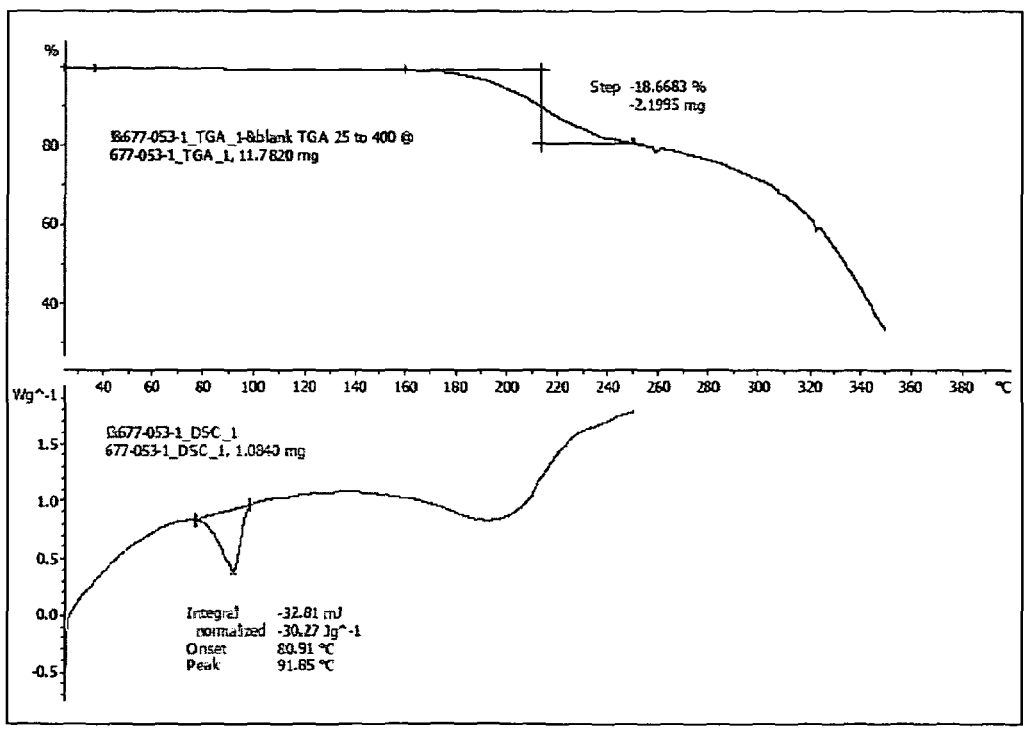

FIG. 34 shows a DSC thermogram (lower trace) of the L-malate salt Form Q of compound (I) as obtained by Example 17, using Mettler DSC823e at a heating rate of 10° C. min$^{-1}$ (peak max observed at 92° C.). The upper trace shows TGA analysis for the same salt using a Mettler TGA/SDTA 851e at a heating rate of 10° C. min-1.

Figure 35:
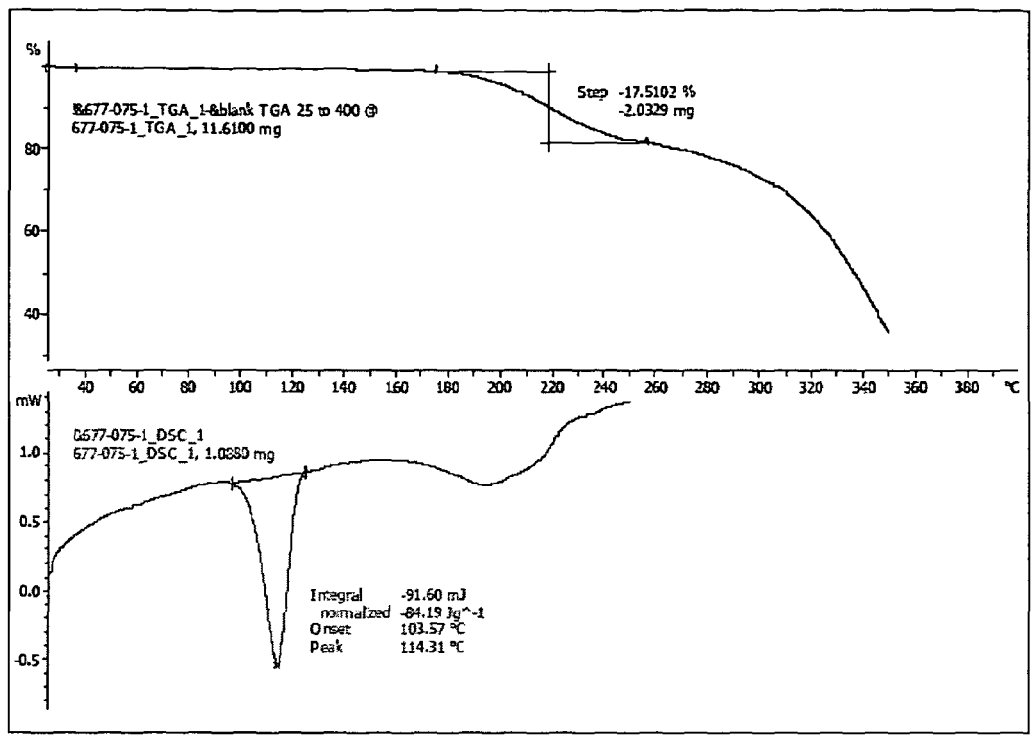

FIG. 35 shows a DSC thermogram (lower trace) of the L-malate salt Form R of compound (I) as obtained by Example 18, using Mettler DSC823e at a heating rate of 10° C. min$^{-1}$ (peak max observed at 114° C.). The upper trace shows TGA analysis for the same salt using a Mettler TGA/SDTA 851e at a heating rate of 10° C. min$^{1}$.

Figure 36:
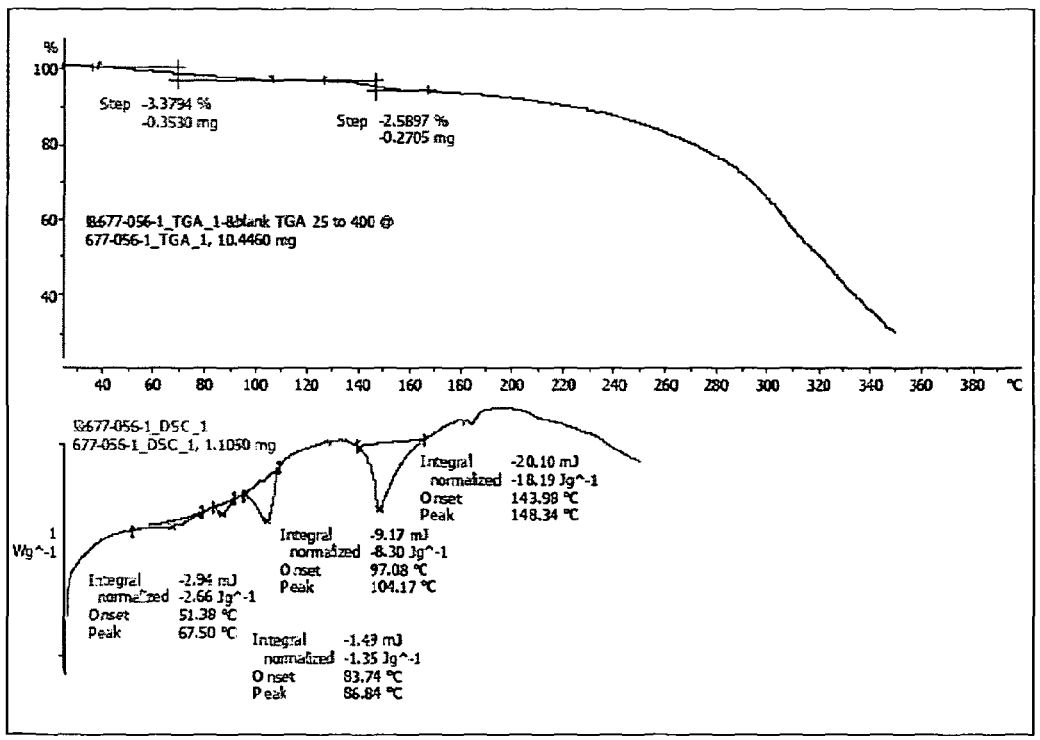

FIG. 36 shows a DSC thermogram (lower trace) of the HCl salt Form H of compound (I) as obtained by Example 8, using Mettler DSC823e at a heating rate of 10° C. min$^{-1}$ (peak max observed at 68, 87, 104 and 148° C.). The upper trace shows TGA analysis for the same salt using a Mettler TGA/SDTA 851e at a heating rate of 10° C. min$^{-1}$.

Figure 37:
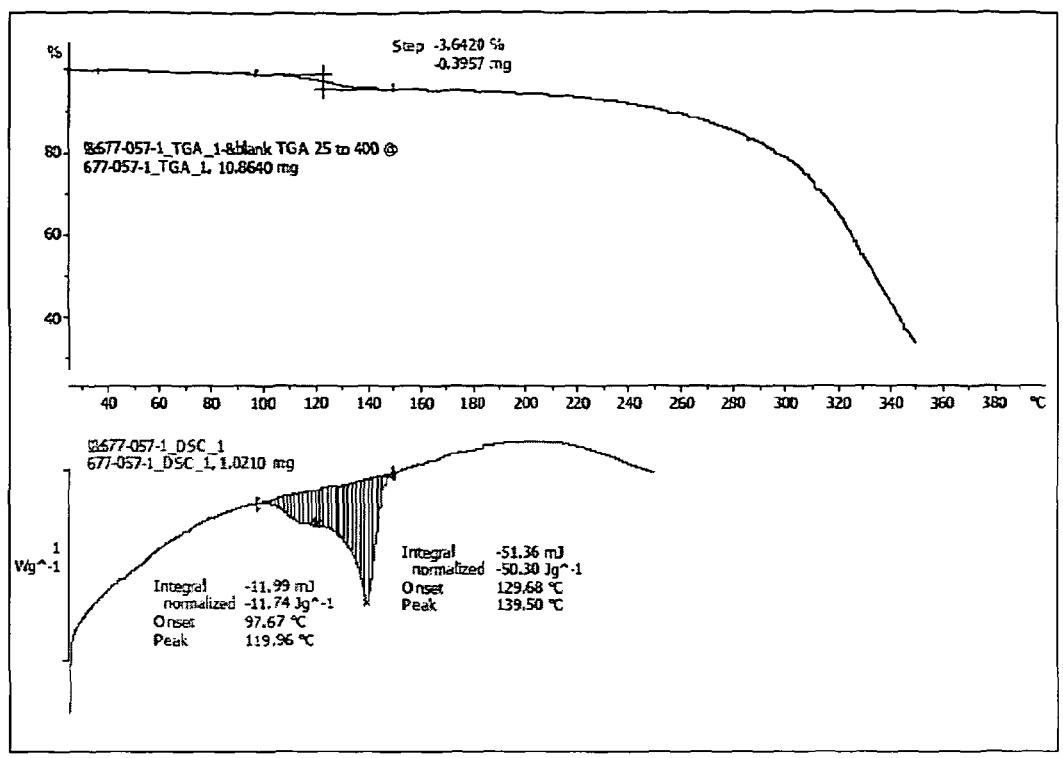

FIG. 37 shows a DSC thermogram (lower trace) of the HCl salt Form I of compound (I) as obtained by Example 9, using Mettler DSC823e at a heating rate of 10° C. min$^{-1}$ (peak max observed at 120 and 139° C.). The upper trace shows TGA analysis for the same salt using a Mettler TGA/SDTA 851e at a heating rate of 10° C. min$^{-1}$.

Figure 38:
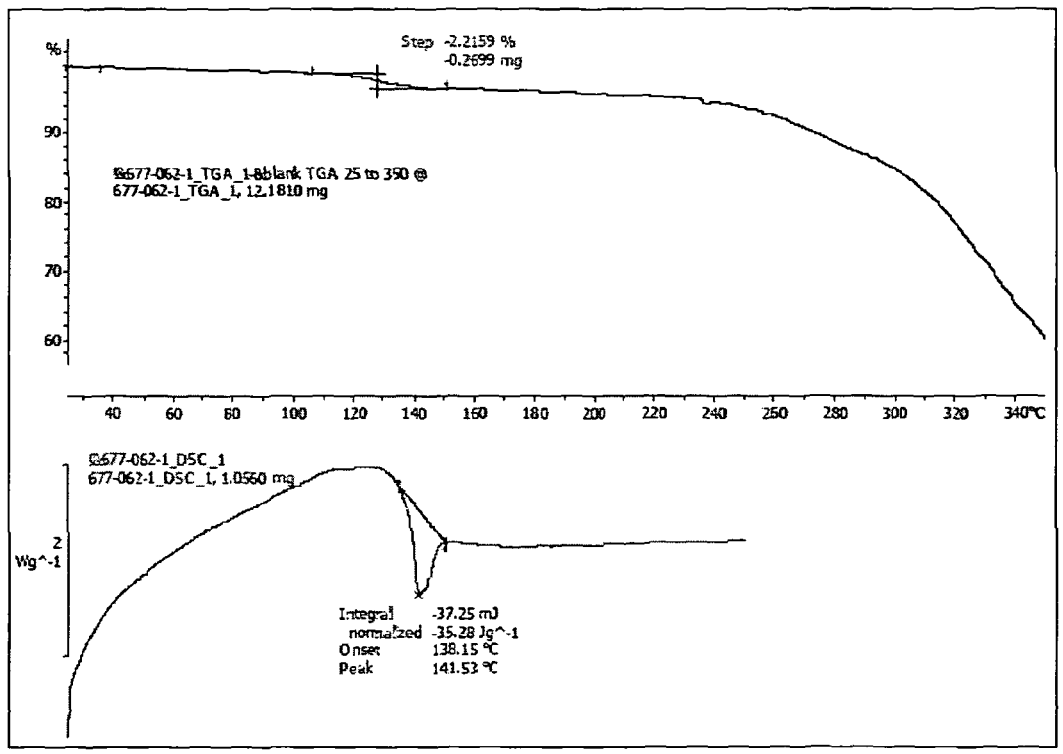

FIG. 38 shows a DSC thermogram (lower trace) of the HBr salt Form J of compound (I) as obtained by Example 10, using Mettler DSC823e at a heating rate of 10° C. min$^{-1}$ (peak max observed at 142° C.). The upper trace shows TGA analysis for the same salt using a Mettler TGA/SDTA 851e at a heating rate of 10° C. min$^{1}$.

The present invention is further described with reference to the following non-limiting Examples.

EXAMPLES

Instrument and Methodology Details

X-Ray Powder Diffraction (XRPD)

All XRPD patterns referred to herein are obtained using copper K-alpha radiation. As used herein, XRPD values as described in the accompanying specification, figures or tables refer to approximate values. Where the reference is to XRPD values listed in the tables, this refers to the 2-theta values, independent of any other parameters listed in the tables, such as peak intensity or the like.

XRPD on the phosphate (Forms B, C), citrate (Form F), benzenesulfonic acid (Form G) and L-tartrate (Form D) salts were carried out using a Bruker AXS C2 GADDS diffractometer as described below.

XRPD on the hydrochloride (Forms H, I), hydrobromide (Forms J, K), mesylate (Form L), maleate (Form M), gentisate (Form O), fumarate (Form P), and L-malate (Forms, Q, R) salts were carried out using a Bruker AXS D8 Advance diffractometer as described below. XRPD on free base (Form A) compound (I) and the L-tartrate salt (Form E) was carried out using PANalytical diffractometer as described below.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2.

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2. Unless otherwise stated, XRPD patterns collected on this instrument were used to produce the XRPD peak lists.

Samples were run under ambient conditions as flat plate specimens using powder as received. Approximately 10 mg of the sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s. step-1

Ambient Conditions

Samples run under ambient conditions were prepared as flat plate specimens using powder as received without grinding. Approximately 1-2 mg of the sample was lightly pressed on a glass slide to obtain a flat surface.

Non-ambient Conditions

Samples run under non-ambient conditions were mounted on a silicon wafer with heat conducting compound. The sample was then heated to the appropriate temperature at ca. 10° C. $min^{-1}$ and subsequently held isothermally for ca 1 minute before data collection was initiated.

PANalytical X'Pert PRO

X-Ray Powder Diffraction patterns were collected on a PANalytical diffractometer using Cu Kα radiation (45 kV, 40 mA), goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

Samples were run under ambient conditions and analysed by transmission foil XRPD, using the powder sample as received. Approximately 2-5 mg of the sample was mounted on a 96 position sample plate supported on a polyimide (Kapton, 12.7 μm thickness) film. Data was collected in the range 3-40° 2 with a continuous scan (speed of 0.146°/s). Samples were oscillated ±2 mm in the x plane at a speed of 2 mm.$s^{-1}$ throughout data collection to maximise particle sampling and minimise preferred orientation effects.

Nuclear Magnetic Resonance (NMR)

$^1$H NMR spectra were collected on a Bruker 400 MHz instrument equipped with an auto-sampler and controlled by a DRX400 console. Automated experiments were acquired using ICONNMR v4.0.4 (build 1) running with Topspin v 1.3 (patch level 8) using the standard Bruker loaded experiments. For non-routine spectroscopy, data were acquired through the use of Topspin alone. Samples were prepared in d6-DMSO, unless otherwise stated. Off-line analysis was carried out using ACD SpecManager v 9.09 (build 7703).

Differential Scanning Calorimetry (DSC)

DSC studies on the phosphate (Forms B, C), citrate (Form F), benzenesulfonate (Form G), L-tartrate (Form D), hydrochloride (Forms H and I), hydrobromide (Form J and K), mesylate (Form L), maleate (Form M), gentisate (Form O), fumarate (Form P), L-malate (Form Q and R) salts were carried out using a Mettler DSC 823e as described below.

DSC studies on free base (Form A) compound (I) were carried out using PerkinElmer Pyris 6 DSC described below.

DSC studies on the L-tartrate salt (Form E) were carried out using PerkinElmer DSC 4000 DSC described below.

Mettler DSC 823e

DSC data were collected on a Mettler DSC 823e equipped with a 50 position auto-sampler. The instrument was calibrated for energy and temperature using certified indium. Typically 0.5-3 mg of each sample, in a pin-holed aluminium pan, was heated at 10° C. $min^{-1}$ from 25° C. to 350° C. A nitrogen purge at 50 ml. $min^{-1}$ was maintained over the sample. The instrument control and data analysis software was STARe v9.10.

PerkinElmer Pyris 6 DSC/DSC 4000

DSC data was collected on a PerkinElmer Pyris 6 DSC or DSC 4000. The instrument was verified for energy and temperature calibration using certified indium. A predefined amount of sample (in mg) was placed in a pin holed aluminium pan and heated at 20° C. $min^{-1}$ from 30° C. to 320° C. The instrument control and data analysis was Pyris Software v9.0.1.0174.

Thermo-Gravimetric Analysis (TGA)

Mettler TGA/SDTA 851e

TGA data were collected on a Mettler TGA/SDTA 851e equipped with a 34 position autosampler. The instrument was temperature calibrated using certified indium. Typically 5-30 mg of each sample was loaded onto a pre-weighed aluminium crucible and was heated at 10° C. $min^{-1}$ from ambient temperature to 350° C. A nitrogen purge at 50 ml. $min^{-1}$ was maintained over the sample. The instrument control and data analysis software was STARe v9.10.

Pyris 1 TGA

TGA data was collected on a Pyris 1 TGA equipped with a 20 position autosampler. The instrument was calibrated using certified indium. 6.329 mg of the sample was loaded onto a pre-weighed aluminium crucible and was heated at 20° C. $min^{-1}$ (or 40° C. $min^{-1}$) from ambient temperature to 500° C.

A nitrogen purge at 20 ml. min$^{-1}$ was maintained over the sample. The instrument control and data analysis was Pyris Software v9.0.1.0174.

Polarised Light Microscopy (PLM)

Samples were studied on a Leica LM/DM polarised light microscope with a digital videocamera for image capture. A small amount of each sample was placed on a glass slide, mounted in immersion oil and covered with a glass slip, the individual particles being separated as well as possible. The sample was viewed with appropriate magnification and partially polarised light, coupled to a λ false-colour filter.

Microscopy

Samples were studied on a Leica DME polarised light microscope with a digital video camera for image capture. A small amount of the sample was placed on a glass slide and covered with a glass slip, individual particles being separated as well as possible. The sample was viewed with appropriate magnification (10x/0.22) and fully polarised light to assess crystallinity.

Hot Stage Microscopy (HSM)

Hot Stage Microscopy was carried out using a Leica LM/DM polarised light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarised light, coupled to a λ false-colour filter, whilst being heated from ambient temperature typically at 10-20° C. min$^{-1}$.

Gravimetric Vapour Sorption (GVS)

SMS DVS Intrinsic

Sorption isotherms were obtained using a SMS DVS Intrinsic moisture sorption analyser, controlled by SMS Analysis Suite software. The sample temperature was maintained at 25° C. by the instrument controls. The humidity was controlled by mixing streams of dry and wet nitrogen, with a total flow rate of 200 ml. min$^{-1}$. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

Method Parameters for SMS DVS Intrinsic Experiments:

| Parameters | Values |
| --- | --- |
| Adsorption-Scan 1 | 40-90 |
| Desorption/Adsorption-Scan 2 | 85-Dry, Dry-40 |
| Intervals (% RH) | 10 |
| Number of Scans | 2 |
| Flow rate (ml. min$^{-1}$) | 200 |
| Temperature (° C.) | 25 |
| Stability (C. min$^{-1}$) | 0.2 |
| Sorption Time (hours) | 6 hour time out |

The sample was recovered after completion of the isotherm and re-analysed by XRPD.

Hiden Isochema Moisture Sorption Analyser (IGAsorp)

Sorption isotherms were obtained using a Hiden Isochema Moisture Sorption Analyser (IGAsorp) controlled by IGAsorp Systems Software V6.50.48. The sample temperature was maintained at 25° C. by the instrument controls. The humidity was controlled by mixing streams of dry and wet nitrogen, with a total flow rate of 250 ml. min$^{-1}$. The instrument was verified for relative humidity content by measuring three calibrated Rotronic salt solutions (10-50-88%). The weight change of the sample as a function of % RH was monitored by microbalance (accuracy ±0.005 mg). A defined amount of sample was placed in a tared mesh stainless steel basket under ambient conditions. A full experimental cycle consisted of two scans (sorption and desorption) at a constant temperature (25° C.) and 10% RH intervals over a 10-90% RH range (90 minutes for each humidity level).

Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

Thermodynamic Aqueous Solubility

Aqueous solubility was determined by suspending sufficient compound in HPLC grage water to give a maximum final concentration of ≥10 mg. ml$^{-1}$ of the parent free-form of the compound. The suspension was equilibrated at 25° C. for 24 hours then the pH was measured. The suspension was then filtered through a glass fibre C filter into a 96 well plate. The filtrate was then diluted by a factor of 101. Quantitation was by HPLC with reference to a standard solution of approximately 0.1 mg. ml$^{-1}$ in DMSO. Different volumes of the standard, diluted and undiluted sample solutions were injected. The solubility was calculated using the peak areas determined by integration of the peak found at the same retention time as the principal peak in the standard injection.

HPLC Method Parameters for Solubility Measurements

| | |
| --- | --- |
| Type of method: | Reverse phase with gradient elution |
| Column: | Phenomenex Luna, C18 (2) 5 μm 50 × 4.6 mm |
| Column Temperature (° C.): | 25 |
| Standard Injections (μl): | 1, 2, 3, 5, 7, 10 |
| Test Injections (μl): | 1, 2, 3, 10, 20, 50 |
| Detection: Wavelength, Bandwidth (nm): | 260, 80 |
| Flow Rate (ml. min$^{-1}$): | 2 |
| Phase A: | 0.1% TFA in water |
| Phase B: | 0.085% TFA in acetonitrile |

| Timetable: | Time (min) | % Phase A | % Phase B |
| --- | --- | --- | --- |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

Chemical Purity Determination by HPLC

Purity analysis was performed on an Agilent HP1100 series system equipped with a diode array detector and using ChemStation software vB.02.01-SR1.

HPLC Method Parameters for Chemical Purity Determinations

| Sample Preparation: | 0.5 mg .ml⁻¹ in acetonitrile: water 1:1 v/v |
|---|---|
| Column: | Phenomenex Luna C18 (2), 150 × 4.6 mm. 5 μm |
| Column Temperature (° C.): | 25 |
| Injection (μl): | 5 |
| Detection: Wavelength, Bandwidth (nm): | 255, 90 |
| Flow Rate (ml. min⁻¹): | 1 |
| Phase A: | 0.1% TFA in water |
| Phase B: | 0.085% TFA in acetonitrile |

| Timetable: | Time (min) | % Phase A | % Phase B |
|---|---|---|---|
| | 0 | 95 | 5 |
| | 25 | 5 | 95 |
| | 25.2 | 95 | 5 |
| | 30 | 95 | 5 |

Ion Chromatography (IC)

Data were collected on a Metrohm 761 Compaction chromatography (for cations) and a Metrohm 861 Advanced Compaction chromatography (for anions) using ion Chromatography Net software v2.3. Accurately weighed samples were prepared as stocksolutions in DMSO and diluted 1:9 with either DMSO or water prior to testing. Quantification was achieved by comparison with standard solutions of known concentration of the ion being analysed.

HPLC Method Parameters for Anion Chromatography

| Type of method | Anion exchange |
|---|---|
| Column: | Metrosep A Supp 5-250 (4.0 × 250 mm) |
| Column Temperature (° C.): | Ambient |
| Injection (μl): | 20 |
| Detection: | Conductivity detector |
| Flow Rate (ml. min⁻¹): | 0.7 |
| Eluent: | 3.2 mM sodium carbonate, 1.0 mM sodium hydrogen carbonate in 5% aqueous acetone. | pKa Determination and Prediction
Determination.

Data were collected on a Sirius GlpKa instrument with a D-PAS attachment. Measurements were made at 25° C. in aqueous solution by UV and in methanol water mixtures by potentiometry. The titration media was ionic-strength adjusted (USA) with 0.15 M KCl (aq). The values found in the methanol water mixtures were corrected to 0% co-solvent via a Yasuda-Shedlovsky extrapolation. The data were refined using Refinement Pro software v2.2.

Prediction

Prediction of pKa values was made using ACD pKa prediction software v11.

Log P Determination

Data were collected by potentiometric titration on a Sirius GlpKa instrument using three ratios of octanol:ionic-strength adjusted (ISA) water to generate Log P, Log Pion, and Log D values. The data were refined using Refinement Pro software v2.2. Prediction of Log P values was made using ACD v11 software.

Compound Preparation

Compound (I) may be prepared in accordance with the methodology described in WO 2008/122767 (Cyclacel Limited).

Alternatively Compound (I) may be prepared via the following procedure:

A solution of (4,6-dimethylpyridin-3-ylmethyl)-(2-fluoro-9-isopropyl 9H-purin-6-yl)-amine (30 g), (2R,3S)-3-amino-pentan-2-ol (29.5 g) and DIEA (33.0 mL) in ethylene glycol (270 mL) was heated at 125° C. under nitrogen overnight. A further 0.5 equivalents of (2R,3S)-3-amino-pentan-2-ol (4.9 g) was added and the reaction stirred for an additional 6 hours. Analysis by HPLC indicated 1.9% (4,6-dimethylpyridin-3-ylmethyl)-(2-fluoro-9-isopropyl 9H-purin-6-yl)-amine remained. The reaction was therefore left to stir at 125° C. overnight. Analysis by HPLC now indicated only 0.35% (4,6-dimethylpyridin-3-ylmethyl)-(2-fluoro-9-isopropyl 9H-purin-6-yl)-amine remained. The reaction was therefore cooled to room temperature and added to ethyl acetate (2460 mL). Water (1320 mL) was added and the phases separated. The aqueous phase was extracted with ethyl acetate (2×2460 mL) and the combined organics were washed with water (2×2460 mL), dried over MgSO₄, filtered and stripped. Purification by flash column chromatography (1500 g silica, 3% MeOH in DCM as eluent) gave the desired product as a white solid. Drying in a vacuum oven overnight gave compound (I) in 59% yield (22.3 g, JCCA824). ¹H NMR confirmed the identity of the product and HPLC gave a purity of 99.16%.

Example 1

Crystallisation of Free Base Compound (I) to give Form A

Compound (I) was crystallised from MTBE by the following method. MTBE (2 vol) was added to compound (I) and heated to reflux. The mixture was held at reflux for 30-60 minutes before the temperature was reduced to 50° C. (held for 2 hours). The suspension was allowed to cool slowly to room temperature before being filtered and rinsed with MTBE (3×1 vol). The solids were dried in vacuum oven at 40° C. for 8 hours to afford the desired crystalline free base (mass recovery 84.5%, LC purity 97.4%).

XRPD information on Form A is found in Table 1.

Gravimetric Vapour Sorption on Form A 11.254 mg of sample was placed in a tarred mesh stainless steel basket under ambient conditions. A full experimental cycle consisted of two scans (sorption and desorption) at a constant temperature (25° C.) and 10% RH intervals over a 40-90% range (180 minutes for each humidity level). The mass increase of approximately 0.09 mg (~0.8%) and the facile uptake and loss relative to humidity level indicates a non-hygroscopic sample that dampens with surface moisture only. FIG. 15 shows an isotherm plot for Form A (weight change % vs RH %), whereas FIG. 16 shows a kinetic plot of weight change % vs time and relative humidity %. Analysis of the sample post GVS run showed no change by XRPD (FIG. 17).

Thermodynamic Aqueous Solubility of Form A

Aqueous solubility was determined by suspending sufficient compound in HPLC grade water to give a maximum final concentration of 10 mg. ml⁻¹ of the parent free-form of the compound. The suspension was equilibrated at 25° C. for 24 hours. The suspension was then filtered through a filter into an HPLC vial. The filtrate was then diluted by an appropriate factor. Quantification was executed by HPLC with reference to a standard solution of 0.5 mg in 1 mL acetonitrile/water (1:1). Different volumes of the standard, diluted and undiluted sample solutions were injected. The solubility was calculated using the peak areas determined by integration of the peak found at the same retention time as the principal peak in the standard injection. The aqueous solubility was determined to be 0.329 mg/mL. Analysis of Form A post solubility study showed no change by XRPD (FIG. 18).

Example 2

Preparation of Citrate Salt (Form F) of Compound (I)

Compound (I) (100 mg, 0.25 mmol, 1 equiv), citric acid (49 mg, 0.26 mmol, 1.02 equiv) and ethyl acetate (1 ml, 10 vol) were charged to a vial and stirred under ambient conditions for 24 hours—a small lump of sticky solid remained undissolved. The mixture was stored in a shaker on a heat/cool cycle (60° C./RT, 4 h) for 68 h. The resultant white precipitate was isolated by vacuum filtration, washed with EtOAc (2×500 μl, 2×5 vol) and dried in a vacuum oven at 30° C. for 16 hours to yield the citrate salt as a white solid (53 mg, 40% yield).

The $^1$H NMR spectrum of the citrate salt was consistent with structure and a set of diastereotopic peaks was present corresponding to the citrate anion. $^1$H NMR analysis also confirmed the presence of residual ethyl acetate. XRPD analysis confirmed the material to be crystalline. DSC analysis showed two endothermic events: a sharp peak, corresponding to the melt, with an onset of 145° C. and a broad event with an onset of 165° C. TGA analysis showed no weight loss before or during the melt, followed by decomposition above 180° C., confirming the second endothermic event in the DSC is likely to be decomposition. TGA analysis also proved the material is not a solvate.

A sample of the product was stored in a humidity chamber at 25° C. and 94% RH for 3 days, after which time the material was slightly tacky, though it had not deliquesced. XRPD analysis of this material showed the same pattern as obtained for the initial product, but with a significant amorphous halo. A second sample was stored in a humidity chamber at 25° C. and 75% RH for 70 hours, after which time the sample appeared unchanged and the XRPD pattern obtained for this material was consistent with that of the original product. GVS analysis conformed that no hydrate is formed at high RH, though the material proved to be hygroscopic above 70% RH.

XRPD information on the citrate salt is found in Table 3.
Summary of Results for Citrate Salt:

| Onset of melt | HPLC purity | Aqueous solubility |
|---|---|---|
| 145° C. | 99.9% | >15 mg. ml$^{-1}$ |

Example 3

Preparation of Benzenesulfonic Acid Salt (Form G) of Compound (I)

Compound (I) (100 mg, 0.25 mmol, 1 equiv), benzenesulfonic acid (41 mg, 0.26 mmol, 1.02 equiv) and tert-butylmethylether (1 ml, 10 vol) were charged to a vial and under ambient conditions and stirring was initiated, the mixture never went into solution. The mixture was stirred for 30 minutes, after which time the sample contained a significant quantity of sticky solid. The mixture was stirred for a further 23.5 hours and showed no change. The mixture was stored in a shaker on a heat/cool cycle (60° C./RT, 4 h) for 68 h. The resultant white precipitate was isolated by vacuum filtration, washed with TBME (3×500 μl, 3×5 vol) and dried in a vacuum oven at 30° C. for 16 hours to yield the benzenesulfonic acid salt as a white solid (65 mg, 47% yield).

The 1H NMR spectrum of the benzenesulfonate salt clearly showed aromatic peaks corresponding to the benzenesulfonate. However, a large proportion of the peaks corresponding to compound (I) appear as broadened multiplets, probably due to the presence of the sulfonic acid group, making successful assignment non-trivial. A significant quantity of residual TBME was also visible, though this is believed to be unbound solvent rather than a solvate. XRPD analysis confirmed the material to be crystalline. DSC analysis showed only one endothermic event with an onset of 147° C., and hot stage microscopy confirmed this event to be a melt. TGA analysis exhibited a weight loss of 1.1% between 75 and 120° C. that was not accompanied by an endotherm in the DSC and is attributed to the loss of unbound solvent, proving the material to be non-solvated. Deliquescence of a sample of the product was observed after storage in a humidity chamber at 25° C. and 94% RH for 2 hours. A second sample was stored in a humidity chamber at 25° C. and 75% RH for 70 hours, after which time the sample was slightly tacky. The XRPD pattern obtained for this material was consistent with that of the original product, but with a slightly larger amorphous halo.

XRPD information on the benzenesulfonic acid salt is found in Table 4.
Summary of Results for Benzenesulfonic Acid Salt:

| Onset of melt | HPLC purity | Aqueous solubility |
|---|---|---|
| 147° C. | 98.9% | >20 mg. ml$^{-1}$ |

Example 4

Preparation of L-Tartrate Salt (Form D) of Compound (I)

Compound (I) (500 mg, 1.26 mmol, 1 equiv.), L-tartaric acid (193 mg, 1.28 mmol, 1.02 equiv) and ethyl acetate (5 ml, 10 vol) were charged to a flask and stirred under ambient conditions for 2 hours, precipitation occurred inside 1 hour. The white precipitate was isolated by vacuum filtration, washed with EtOAc (3×0.5 ml, 2×1 ml) and dried in a vacuum oven at 40° C. for 16 hours to yield the L-tartrate salt as a white solid (565 mg, 82% yield).

The $^1$H NMR spectrum of the tartrate salt was consistent with structure and exhibited a singlet at 4.31 ppm corresponding to the tartrate anion. XRPD analysis confirmed the material to be crystalline. DSC analysis showed a single endothermic event with an onset of 147° C. that was confirmed, by hot stage microscopy, to be a melt. TGA analysis showed no weight loss before or during the melt, followed by decomposition above 200° C., showing that this material is not a solvate.

A sample of product was stored in a humidity chamber at 25° C. and 94% RH for 70 hours, after which time the material was slightly tacky, though it had not deliquesced. XRPD analysis of this material showed the presence of some peaks corresponding to those in the pattern acquired for the original product, though a significant amorphous halo was also visible, due to the uptake of water. A second sample was stored in a humidity chamber at 25° C. and 75% RH for 4 days, after which time the sample was unchanged. The XRPD pattern obtained for this material was consistent with that of the original product. GVS analysis confirmed that no hydrate is formed at high RH, though the material proved to be hygroscopic above 70% RH.

XRPD information on the L-tartrate salt (Form D) is found in Table 2.

Summary of Results for L-Tartrate Salt (Form D):

| Onset of melt | HPLC purity | Aqueous solubility |
| --- | --- | --- |
| 147° C. | 99.4% | >20 mg. ml$^{-1}$ |

Example 5

Preparation of L-Tartrate Salt (Form E) of Compound (I)

Example 5.1

(a) A suspension of Form D L-tartrate salt of compound (I) (1.0 g) in ethanol (12 ml) was heated at reflux. Acetonitrile (3 ml) was added portion wise over 30 minutes. After this addition, a solution was not obtained. Further portions of ethanol (4.5 ml) and acetonitrile (1 ml) were added until a solution was obtained. The solution was polish filtered (hot) then cooled to room temperature at a rate of 10° C./hour (crystallisation initiated at ~65° C.). After stirring at room temperature overnight, the resulting solid was filtered, washed with cold ethanol (5 ml) and pulled dry. Further drying in a vacuum oven at 50° C. yielded the desired product as a white crystalline solid (0.725 g, 73%). $^1$H NMR analysis confirmed a 1:1 salt and XRPD confirmed Form E.

A solubility study at 25° C. indicated a solubility for Form E of 43.905 mg/ml) 24 hour incubation in water with constant agitation). The remaining solid was dried and XRPD analysis showed no differences in powder pattern after the aqueous slurry. The pH of the solution post solubility was pH 5.

A TGA study for Form E was also carried out (held at 100° C. for 24 hours). The results indicated the material was stable at this temperature and XRPD analysis of the material post TGA stability study showed no differences in powder pattern.

XRPD information on the L-tartrate salt (Form E) is found in Table 7.

Example 5.2

A suspension of Form D L-tartrate salt of compound (I) (10.2 g) in ethanol (120 ml) was heated to 65° C. Acetonitrile (20 ml) was added and the suspension heated at reflux for 10 minutes after which time a solution was obtained. The solution was cooled to room temperature over 2-3 hours with crystallisation initiating at ~50° C. The resulting suspension was stirred at room temperature overnight. The resulting solid was filtered, washed with ethanol (10 ml) and pulled dry. Further drying in a vacuum oven at 50° C. yielded the desired product as a white crystalline solid (8.76 g, 88%). $^1$H NMR analysis confirmed a 1:1 salt and XRPD confirmed Form E.

Example 5.3

Slurry Conversion

Form E of the L-Tartrate salt of compound (I) was also prepared by slurry conversion from four different solvents (ethyl acetate, IPA, IMS or acetonitrile). A 1:1 mixture of Form by weight of D: Form E L-Tartrate salt (200 mg total) was heated at 45° C. over 48 hours in 2 ml of solvent prior to filtration and analysis. Form E was produced in each slurry (purity≥98%).

Example 5.4

Seeding

A suspension of Form D L-tartrate salt compound (I) (10.2 g) in ethanol (120 ml) was heated to 65° C. Acetonitrile (20 ml) was added and the suspension heated at reflux for 10 minutes. The mixture was polish filtered through HPLC filter frits. No precipitation was observed in process. The material was then cooled from reflux and seeded at 70° C. with Form E L-tartrate salt (as prepared above), cooling at a rate of 10° C. every 1.5 hours. The first seed dissolved completely and seeding was repeated at 60° C. The seed remained and the solution changed to show a very faint opaque phase. Crystallisation began at approximately 50° C. An isolated yield of 80% was obtained.

Example 5.5

Formation from Free Base of Compound (I)

CYC065 free base Form A (0.2 g) was dissolved in ethanol (9 vol, 1.8 mL) and heated at reflux. A solution of tartaric acid (1 eq, 0.076 g) in water (1.7 vol, 0.34 mL)/ethanol (1 vol, 0.2 mL) was added dropwise maintaining the temperature at reflux. The resulting solution was then polish filtered before cooling to 70° C. A seed of Form E was added giving a cloudy solution. The batch was stirred at 70° C. for 1 hour before cooling to room temperature. After stirring at room temperature for 2 hours, the solid was filtered, washed with ethanol (2×0.5 mL) and pulled dry. Further drying in a vacuum oven at 50° C. yielded CYC065-L-tartrate salt Form E as a white solid (0.2 g, 72%). $^1$H NMR confirmed a 1:1 salt and HPLC indicated a purity of 97.97%. XRPD and DSC confirmed Form E.

Example 6

Preparation of the Phosphate Salt (Form C) of Compound (I) from Ethanol

A solution of phosphoric acid in water (85% w/w) (1920, 1.67 mmol, 1.02 equiv) was added to a stirring solution of compound (I) (650 mg, 1.64 mmol, 1 equiv) in ethanol (6.5 ml, 10 vol) at RT in a cool water bath over a period of 2 minutes, the mixture remained a light yellow solution throughout the addition. The water bath was removed and the mixture was stirred at RT for 2 hours and the resultant white precipitate was isolated by vacuum filtration, washed with ethanol (2×1.3 ml, 2×2 vol) and dried in a vacuum oven at 40° C. for 16 hours to yield the phosphate salt as a white solid (641 mg, 66% yield).

The XRPD pattern obtained for the product was similar, though not identical to, the corresponding material crystallised from IPA (see Example 7). These results suggest that crystallisation from ethanol yields a different polymorph of the resultant phosphate salt than crystallisation from IPA. DSC analysis showed two broad endothermic events with onsets of 67 and 125° C. The first endotherm was comparable with the first event observed in the DSC traces of the material formed in IPA (see Example 7). Interestingly, the second endotherm had a significantly higher onset (123° C.) than the comparable material obtained from IPA (116° C.), again suggesting the presence of a different solid form.

The ¹H NMR spectrum obtained was consistent with the structure and showed a minor amount of residual ethanol.

TGA analysis showed a weight loss of 2.9%, between 45 and 98° C., corresponding to the first endotherm in the DSC, thus confirming that the first endotherm observed in the DSC was due to the loss of bound solvent. At this stage, it was not confirmed whether this solvent loss was due to the loss of IPA or water, or a mixture of both. TGA analysis showed no weight loss associated with the second event observed in the DSC, followed by decomposition above 220° C. Hot stage microscopy confirmed the second endotherm observed in the DSC to be a melt.

GVS analysis was undertaken at 25° C. and showed the material is not hygroscopic as a gradual uptake of 0.5% by weight of water between 60 and 90% RH was observed. A weight loss of 0.5% was observed between 10 and 0% RH, which is lower than the weight loss observed in the TGA.

Variable temperature XRPD analysis was undertaken on a sample of Form C in order to elucidate if the loss of solvent observed in the DSC resulted in a change of form. The sample was heated to each temperature, held for 3 minutes to allow equilibration and an XRPD pattern was collected. The material was taken to 100° C., in 10 degree increments, a pattern was collected, the sample was held at 100° C. for 15 minutes and a second pattern was collected. The sample was cooled back to RT and a final reference pattern was obtained.

Subtle changes were observed between the XRPD patterns acquired at RT, both before and after cooling, and the pattern obtained at 100° C. This suggests that loss of solvent does bring about a change in form and that this process is reversible in the presence of air. DSC analysis of the sample after it had undergone VT XRPD analysis exhibited two broad endotherms, with onsets of 67 and 124° C., and was analogous to the DSC trace obtained for the sample prior to undergoing the VT XRPD experiment. This result confirms that the loss of solvent is reversible in air, therefore implying that the product exists as a hydrated form under ambient conditions and not as an alcoholic solvate.

In order to add further weight to this hypothesis a heat/cool/heat DSC analysis was undertaken. In this experiment, a sample of product was heated to 100° C., held for 10 minutes, cooled to 30° C., held for 5 minutes and then re-heated to 250° C. As anticipated the first heat showed the desired endotherm corresponding to the loss of water. The second heat only exhibited a single endotherm, corresponding to the melt of the anhydrous form, therefore confirming that the loss of water is irreversible under an inert atmosphere of nitrogen.

XRPD information on the phosphate salt prepared from ethanol (Form C) is found in Table 5.

Summary of Results for Phosphate Salt Prepared from Ethanol:

| Onset of dehydration | Onset of melt | Wt loss TGA | HPLC purity | Aqueous solubility | % H₂O Karl Fischer |
|---|---|---|---|---|---|
| 68° C. | 123° C. | 2.8 | 99.6% | >20 mg. ml⁻¹ | 3.5 |

Removal of all residual ethanol was achieved by drying in a vacuum oven either at 60° C. for 24 hours (76 mg scale, Sample A) or at 50° C. for 68 hours (346 mg scale, Sample B). ¹H NMR, HPLC purity, XRPD and DSC analyses all confirmed that the dry materials were analogous to the starting product and had not degraded during the drying process. TGA and Karl Fischer analyses were used to calculate the equivalents of water.

| | Onset of dehydration | Onset of melt | Wt loss TGA | HPLC purity | Equiv H₂O | % H₂O Karl Fischer |
|---|---|---|---|---|---|---|
| Sample A | 67° C. | 122° C. | 2.5 | 99.6% | 0.83 | N/A |
| Sample B | 70° C. | 123° C. | 2.4 | N/A | 0.82 | 3.0 |

Example 7

Preparation of the Phosphate Salt (Form B) of Compound (I) from Propan-2-ol

A solution of phosphoric acid in water (85% w/w) (147 μl, 1.28 mmol, 1.02 equiv) was added to a stirring solution of compound (I) (500 mg, 1.26 mmol, 1 equiv) in isopropanol (5 ml, 10 vol) at RT in a cool water bath over a period of 2-3 minutes. A sticky white material formed into a disk during the addition. The mixture was stirred vigorously for 30 minutes, after which time the mixture had become a thick yellow sludge and stirring was poor. A further 750 μl of IPA was added and the mixture was stirred for a further 1 h. The resultant white precipitate was isolated by vacuum filtration and washed with IPA (2×1.5 ml, 2×3 vol) and dried under suction. Two distinct types of material were clearly visible in the cake—a dry white powdery solid round the outside and a sticky off white solid in the centre. The dry solid was isolated to yield the phosphate salt as a white solid (110 mg, 15% yield).

The ¹H NMR spectrum of the product was consistent with structure, a minor amount of residual IPA was also noted. The XRPD confirmed that the product was in crystalline form. The DSC trace exhibited two events with onsets of 67 and 116° C. and the TGA exhibited a weight loss of 2.6%, between 45 and 98° C., corresponding to the loss of bound solvent during the first endothermic event in the DSC. At this stage it was not confirmed whether this solvent loss was due to loss of IPA or water, or a mixture of both. The TGA showed no weight loss associated with the second event in the DSC, followed by decomposition above 220° C. Hot stage microscopy confirmed the second endotherm observed in the DSC to be a melt.

XRPD information on the phosphate salt prepared from propan-2-ol (Form B) is found in Table 6.

Summary of Results for Phosphate Salt Prepared from propan-2-ol:

| Onset of dehydration | Onset of melt | Wt loss TGA | HPLC purity |
|---|---|---|---|
| 67° C. | 116° C. | 2.6% | 99.5% |

Variable temperature XRPD analysis was undertaken on the product in order to elucidate if the loss of solvent observed in the DSC resulted in a change of form. The sample was heated to each temperature, held for 3 minutes to allow for equilibration and an XRPD pattern was collected. The material was taken to 100° C., in 10 degree increments, a pattern was collected then the sample was held at 100° C. for 15 minutes and a second pattern was collected. The sample was cooled back to RT and a final reference pattern was obtained.

There are only very subtle changes in the XRPD patterns obtained at RT and at 100° C., although they do appear to be reversible as the differences disappear again upon cooling to RT.

Given the suggestion, from the VT XRPD analysis, that the product might be a hydrate that can reversibly lose then reacquire water with heating, a heat/cool/heat DSC experiment was undertaken under an inert atmosphere of nitrogen. A sample of product was heated to 100° C., held for 10 minutes, cooled to 30° C., held for 5 minutes and then re-heated to 250° C. The first heat showed, as anticipated, the loss of solvent. However, the second heat showed no endothermic event corresponding to the loss of solvent therefore showing that this process is irreversible under an inert atmosphere of nitrogen. To investigate whether the phosphate salt exists as a hydrate under ambient conditions that can be reversibly dehydrated at temperature in the presence of air, a series of TGA experiments were undertaken to clarify how quickly the material rehydrates under ambient conditions. A series of samples were taken to 100° C. then cooled to 25° C. under nitrogen using the TGA equipment. The samples were stored under ambient conditions (RT in air) for varying times and then the TGA experiment was re-run. As a comparison a heat/cool/heat experiment was undertaken under an inert atmosphere of nitrogen using the TGA; a sample was heated to 100° C., cooled to 25° C. and heated to 100° C. for a second time.

These results showed that the phosphate salt readily rehydrates under ambient conditions (assumed to be approximately 25° C. and 40% RH). Within 30 minutes an 8 mg sample of product in an open TGA pan had fully rehydrated. This result is promising for any potential scale up as it shows that even if, during the drying process, some, or all, of the water is lost from the sample, it will rehydrate upon storage under ambient conditions.

A sample of product was stored in a humidity chamber at 25° C. and 94% RH for 88 hours, after which time no deliquescence was observed. The XRPD pattern obtained for this material matched those acquired for the phosphate salt crystallised from ethanol (see Example 6), rather than that of the parent compound. The DSC analysis exhibited two discreet melts, corresponding to the crystalline form produced by crystallisation from IPA and that produced from ethanol, with the melt of the ethanol form appearing to be the dominant event. GVS analysis was undertaken at 25° C. and showed the material not to be hygroscopic as a gradual uptake of only ~1.5 weight % of water was observed above 80% RH. Interestingly upon taking to 0% RH only 0.5 weight % of water was lost, compared to >2% observed in the TGA. The XRPD pattern obtained for this material matched those acquired from product crystallised from ethanol, rather than that of the parent compound. The DSC analysis exhibited broadening of the endotherm corresponding to the melt, though it still appeared as a single event.

It was postulated that complete loss of water may only occur at elevated temperature, thus a second GVS experiment was run at 40° C. At 40° C. the product exhibited a gradual uptake of ~2 weight % of water above 80% RH, again proving the material is not hygroscopic. On this occasion upon taking to 0% RH the material lost ~2.6 weight % of water, which is in close agreement with the mass loss observed in the TGA. The XRPD pattern obtained for this material matched those acquired from product crystallised from ethanol, rather than that of the parent compound. The DSC analysis exhibited two discreet melts corresponding to the crystalline form produced by crystallisation from IPA and that produced from ethanol, with the melt of the ethanol form appearing to be the dominant.

Example 8

Preparation of Hydrochloride Salt (Pattern 1; Designated Form H) of Compound (I)

HCl (37 wt % solution in water) (88 µl, 0.88 mmol, 1 equiv) was added dropwise to a solution of free base compound (I) (350.22 mg, 0.88 mmol, 1 equiv) in TBME (17.5 ml, 50 relative volumes) at RT with swirling—a sticky white solid formed instantaneously. The sample was stored in a shaker on a heat/cool cycle (40° C./RT, 4 h at each) for 63 h. The mixture had concentrated to approximately ⅓ original volume during the maturation. The resultant solid was isolated by vacuum filtration and washed with TBME (2×5 ml). The solid was dried under suction and in a vacuum oven at 30° C./3 mbar for 20 h to yield the hydrochloride salt as a white solid (158.69 mg, 42% based on mono-chloride salt formation).

Summary of Data for Hydrochloride Salt (Form H) of Compound (I)

| Analysis | Result |
| --- | --- |
| $^1$H NMR | Changes consistent with salt formation, different to HCl Pattern 2 (Form I) |
| | 2.7% residual TBME (0.1 equiv) |
| XRPD | Consistent with HCl Pattern 1 (Form H) |
| VT-XRPD | Conversion to a new pattern >80° C., sample became amorphous >100° C. |
| IC | 2.2 equiv of chloride |
| DSC | Four broad endotherms with onset temperatures at 51.4, 83.7, 97.1 and 144.0° C. |
| | (ΔH 3, 1, 8 and 18 respectively) |
| TGA | 3.4% wt loss from 45 to 105° C. equates to 0.8 equiv water 2.6% wt loss from 130 to 170° C. - loss of TBME? |
| HSM | Loss of birefringence at 60° C., melt/formation of a gum accompanied by loss of solvent from 85° C. |
| Karl Fischer | 8.6% water equates to 2.3 equiv water |
| HPLC | 98.8% (largest % imp 0.46 @ 1.11 RRT) |
| AQ Solubility | 75 mg · ml$^{-1}$, pH 2.2 |
| 40° C./75% RH | 30 min - Deliquescence |

XRPD information on the hydrochloride salt (Form H) of compound (I) is found in Table 8 and FIG. 19.

XRPD analysis of the product appeared to suggest formation of HCl Pattern 1 (Form H), however, the ion chromatography results were inconsistent with those obtained previously for HCl Pattern 1 (Form H) that suggested it to be a mono-chloride. These results were unexpected, and do not match the observation that HCl Pattern 2 (Form I, mono chloride salt) shows conversion to HCl Pattern 1 (Form H) upon storage at 40° C./75% RH.

In an attempt to confirm the formation of a bis-HCl salt, a sample of the hydrochloride salt (Form H) (25.99 mg) was slurried in 3% water in EtOAc (1.3 ml, 50 relative volumes) and the mixture was stored in a shaker on a heat/cool cycle (40° C./RT, 4 h) for 72 h. A colourless gum was obtained. In two further attempts to verify the stoichiometry of the isolated material, samples of the hydrochloride salt (Form H) were washed with 3% water in EtOAc or TBME (3×750 µl) and dried under suction. Unfortunately, in each case a sticky solid was isolated instead of the desired solid.

VT-XRPD analysis of the product suggested conversion of HCl Pattern 1 (Form H) to a new pattern (HCl Pattern 4) above 80° C. followed by complete loss of crystallinity above 100° C. Visual analysis of the sample used for VT-XRPD showed the formation of a foam at elevated temperatures, once crystallinity had been lost, indicative of a loss of volatile material (possibly TBME or excess HCl). TGA shows a weight loss of 3.4% from 45 to 105° C., equivalent to 0.8 equiv $H_2O$ and greater than the observed levels of TBME. The weight loss could indicate the presence of a solvate that desolvates to the different form observed by VT-XRPD. Indeed, HSM showed a loss of birefringence around 60° C. that could indicate desolvation followed by a melt, or the formation of a gum due to the presence of silicone oil, accompanied by the loss of solvent from 85° C. These results suggest HCl Pattern 1 (Form H) material to be a solvate, however due to the presence of TBME by NMR and two weight losses by TGA it cannot be verified whether the material is a TBME solvate or hydrate.

Example 9

Preparation of Hydrochloride Salt (Pattern 2; Designated Form I) of Compound (I)

HCl (37 wt % solution in water) (95 µl, 0.95 mmol, 0.9 equiv) was added dropwise to a solution of free base compound (I) (399.72 mg, 1.01 mmol, 1 equiv) in EtOAc (12 ml, 30 relative volumes) at RT with swirling—a sticky white solid formed instantaneously. The sample was stored in a shaker on a heat/cool cycle (40° C./RT, 4 h at each) for 63 h. The resultant solid was isolated by vacuum filtration and washed with EtOAc (2×3 ml). The solid was dried under suction and in a vacuum oven at 30° C./3 mbar for 20 h to yield the hydrochloride (Form I) as a yellow solid (151.71 mg, 35% based on mono-chloride salt formation).

Summary of Data for Hydrochloride Salt (Form I) of Compound (I)

| Analysis | Result |
| --- | --- |
| $^1$H NMR | Changes consistent with salt formation, different to HCl 1 (Form H) 5.0% residual EtOAc (~0.2 equiv) |
| XRPD | Partially crystalline, consistent with HCl Pattern 2 (Form I) Matched HBr Pattern 1 (Form K) |
| VT-XRPD | No change up to 120° C., melt by 140° C. |
| IC | 1.0 equiv of chloride |
| DSC | Two overlapping endotherms 97.7 and 129.7° C. ($\Delta$H 12 and 50 J · g$^{-1}$) |
| TGA | 3.6% wt loss from 100 to 140° C., loss of EtOAc? |
| HSM | Extended melt with an onset of 109° C. some degradation above 125° C. |
| HPLC | 99.1% (largest % imp 0.33 @ 1.07 RRT) |
| AQ Solubility | >79 mg · ml$^{-1}$, pH 4.4 |
| 40° C./75% RH | 7 d - Sticky solid, XRPD showed conversion to HCl Pattern 1 (Form H) |

XRPD information on the hydrochloride salt (Form I) of compound (I) is found in Table 9 and FIG. 20.

Analysis of the product confirmed HCl Pattern 2 (Form I) material to be a mono-chloride salt that appears to be isostructural with HBr Pattern 1. HSM shows a melt corresponding to the broad endotherms observed in the DSC, whilst VT-XRPD shows no change in form before the melt. These results suggest the material to be non-solvated, thus the residual solvent observed in the NMR is likely to be trapped within the crystal lattice and is lost upon melting, as observed in the TGA. Storage of HCl Pattern 2 (Form I) material at 40° C./75% RH showed it to be unstable under elevated levels of relative humidity.

Analysis of HCl Pattern 1 (Form H)

HCl Pattern 2 (Form I) showed conversion to HCl Pattern 1 (Form H) upon storage at 40° C./75%. This result may indicate that HCl Pattern 1 (Form H) is likely to be a mono-chloride salt. Proton NMR and TGA analyses were undertaken on this sample in an attempt to clarify the properties of HCl Pattern 1 (Form H) material, as the analysis sample from Example 8 was complicated by the presence of residual TBME and possibly excess HCl. Proton NMR confirmed the absence of residual TBME, whilst TGA showed a stepped weight loss of 4.6%, equivalent to 1.2 equiv of water. These results suggest HCl Pattern 1 (Form H) material to be a mono-hydrated mono-chloride salt of compound (I).

Example 10

Preparation of Hydrobromide Salt (Pattern 1; Designated Form J) of Compound (I)

HBr (48 wt % solution in water) (77 µl, 0.45 mmol, 0.9 equiv) was added dropwise to a solution of free base of compound (I) (200.46 mg, 0.50 mmol, 1 equiv) in EtOAc (10 ml, 50 relative volumes) at RT with swirling—a sticky white solid formed instantaneously. The sample was stored in a shaker on a heat/cool cycle (40° C./RT, 4 h at each) for 18 h. The resultant sticky solid was isolated by vacuum filtration and washed with EtOAc (2×2 ml). The solid was dried under suction and in a vacuum oven at 30° C./3 mbar for 14 h to yield the hydrobromide salt as a yellow solid (86.54 mg, 40% based on mono-bromide salt formation).

Summary of Data for Hydrobromide Salt (Form J) of Compound (I)

| Analysis | Result |
| --- | --- |
| $^1$H NMR | Changes consistent with salt formation 5% residual EtOAc (~0.2 equiv) |
| XRPD | Partially crystalline, consistent with HBr Pattern 1 (Form J) Matched HCl Pattern 2 (Form I) |
| IC | 1.1 equiv of bromide |
| DSC | Broad endotherm 138.2° C. ($\Delta$H 35 J · g$^{-1}$) |
| HSM | Melt observed with an onset of 119° C. |
| TGA | 2.2% wt loss from 105 to 150° C., loss of EtOAc? |
| HPLC | 99.0% (largest % imp 0.34 @ 1.07 RRT) |
| AQ Solubility | >30 mg · ml$^{-1}$, pH 4.7 |
| 40° C./75% RH | 15 h - Deliquescence 7 d - Sticky solid, XRPD showed conversion to a new Pattern; HBr 2 (Form K) |

XRPD information on the hydrobromide salt (Form J) of compound (I) is found in Table 10 and FIG. 21.

Analysis confirmed HBr Pattern 1 (Form J) to be a partially crystalline mono-bromide salt that appears to be isostructural with HCl Pattern 2 (Form I). HSM and DSC analyses suggest a melt with an onset of approximately 138° C. As with HCl Pattern 2 (Form I), it is proposed that the material is non-solvated and that the weight loss observed in the TGA is due to the loss of solvent trapped within the crystal lattice upon melting. Storage at 40° C./75% RH showed conversion to a new Pattern—HBr Pattern 2 (Form K).

Example 11

Preparation of Hydrobromide salt (Pattern 2; designated Form K) of Compound (I)

A new XRPD pattern corresponding to the HBr salt was obtained upon storage of HBr Pattern 1 (Form J) at 40° C./75% relative humidity. HBr Pattern 1 (Form J) showed deliquescence after 15 h, but crystallisation was observed upon extended storage of 7 days.

Summary of Data for Hydrobromide (Form K) of Compound (I)

| Analysis | Result |
|---|---|
| XRPD | Different to HBr pattern 1 (Form J) - HBr Pattern 2 (Form K) (inconsistent with HCl 1 (Form H)) |
| DSC | Broad endotherm 51.0° C. ($\Delta$H 70 J · g$^{-1}$) followed immediately by a sharp endotherm 90.3° C. ($\Delta$H 75 J · g$^{-1}$) |
| TGA | 3.0% wt loss from 45 to 70° C. equates to 0.8 equiv water |
| IC | 1.0 |

Analysis suggests HBr Pattern 2 (Form K) to be a monohydrated mono-bromide salt, exhibiting dehydration with an onset of approximately 50° C. Further scale up and analysis of this material may be beneficial to further confirm these observations.

Example 12

Preparation of Mesylate salt (Form L) of Compound (I)

Methanesulfonic acid (59 μl, 0.91 mmol, 0.9 equiv) was added dropwise to a stirring solution of free base compound (I) (400.08 mg, 1.0 mmol, 1 equiv) in TBME (20 ml, 50 relative volumes) at RT—a sticky white solid formed instantaneously—and the mixture was stirred at RT for 16 h. A precipitate appeared to have formed and an aliquot was taken and isolated by vacuum filtration. A sticky solid was obtained from the isolated sample that did not improve with drying. The remaining sample was stirred at RT for a further 8 h, heated to 40° C. and stirred for a further 1.5 h, then cooled to RT and stirred for 14 h. An aliquot was taken and the solid was isolated by vacuum filtration yielding a sticky solid. THF (1 ml) was added to the remaining mixture and the sample was stirred for 3 h. The mixture was stored in a shaker on a heat/cool cycle (40° C./RT, 4 h at each) for 63 h—evaporation was observed. TBME (10 ml) was added and the solid was isolated by vacuum filtration and washed with TBME (2×2 ml). The solid was dried under suction and in a vacuum oven at 30° C./3 mbar for 20 h to yield the mesylate salt (Form L) as a white solid (256.73 mg, 51% based on mono-mesylate salt formation).

Summary of Data for Mesylate (Form L) of Compound (I)

| Analysis | Result |
|---|---|
| $^1$H NMR | 1 equiv methanesulfonic acid, 0.4% TBME |
| XRPD | Consistent with Mesylate Pattern 1 |
| IC | 0.7 equiv methanesulfonic acid |
| DSC | Sharp endotherm onset 126.1° C. ($\Delta$H 86 J · g$^{-1}$) |
| TGA | 0.2% wt loss from 110 to 135° C. associated with endotherm - loss of TBME |
| HSM | Melt observed with an onset of 121° C. |
| HPLC | 98.8% (largest % imp 0.45 @ 1.11 RRT) |
| AQ Solubility | 137 mg · ml$^{-1}$, pH 4.53 |
| 40° C./75% RH | 15 h - Deliquesced<br>7 d - No change |

XRPD information on the mesylate salt (Form L) of compound (I) is found in Table 11 and FIG. 22.

Analysis suggested Mesylate Pattern 1 to be a non-solvated mono mesylate salt with a melt at approximately 126° C. The aqueous solubility was determined to be ~140 mg. ml$^{-1}$, the highest of the salts obtained during the course of this work. The sample was found to be hygroscopic as deliquescence was observed inside 15 h at 40° C. and 75% RH.

Example 13

Preparation of Maleate salt (Form M) of Compound (I)

Free base compound (I) (400.85 mg, 1.01 mmol, 1 equiv), maleic acid (117.01 mg, 1.01 mmol, 1 equiv) and TBME (20 ml, 50 relative volumes) were charged to a flask and stirred at RT for 16 h. A fine yellow suspension along a few lumps of yellow solid was observed. An aliquot was taken, the solid was isolated by vacuum filtration, dried under suction and analysed by XRPD (consistent with Maleate Pattern 1). The remaining mixture was stirred at RT for a further 8 h. The solid was isolated by vacuum filtration, dried under suction and in a vacuum oven at 30° C./3 mbar for 15 h to yield the maleate salt (Form M) as a yellow solid (279.67 mg, 54% yield based on mono-maleate salt formation).

Summary of Data for Maleate (Form M) of Compound (I)

| Analysis | Result |
|---|---|
| $^1$H NMR | ~1 equiv maleic acid (peak overlaps with Compound (I)), 1.3% TBME |
| XRPD | Consistent with Maleate Pattern 1 |
| IC | 1.1 equiv maleic acid |
| DSC | Sharp endotherm, onset 116.1° C. ($\Delta$H 75 J · g$^{-1}$) |
| HSM | Melt observed with an onset of 112° C. |
| TGA | 11.1% wt loss from 135 to 195° C. (~0.4 equiv Maleic acid) |
| HPLC | 99.0% (largest % imp 0.31 @ 1.11 RRT) |
| AQ Solubility | 73 mg · ml$^{-1}$, pH 3.9 |
| 40° C./75% RH | 7 d - Sticky solid, XRPD consistent with Maleate Pattern 1 |

XRPD information on the maleate salt (Form M) of compound (I) is found in Table 12 and FIG. 23.

Analysis suggested Maleate Pattern 1 to be a non-solvated mono maleate salt with a melt at approximately 116° C. Material giving Maleate Pattern 1 appears to be hygroscopic above 75% RH, deliquescence was observed at 25° C./97% and a sticky solid, though consistent with Maleate Pattern 1 by XRPD, was obtained at 40° C./75% RH.

Example 14

Preparation of Gentisate Salt (Form N) of Compound (I)

Free base compound (I) (400.27 mg, 1.01 mmol, 1 equiv), gentisic acid (155.25 mg, 1.01 mmol, 1 equiv) and EtOAc (8 ml, 20 relative volumes) were charged to a flask at RT. The mixture was stored in a shaker on a heat/cool cycle (40° C./RT, 4 h at each) for 63 h to give a light yellow solution. The mixture was cooled to 5° C. for 24 h—no precipitation was observed. The mixture was cooled to −18° C. for 24 h—a light yellow solid was formed. The solid was isolated by vacuum filtration using glassware pre-cooled to −18° C. Upon isolation and warming towards RT the sample became a yellow oil. The damp sample was dried in a vacuum oven at 30° C./3 mbar for 20 h to yield the gentisate salt as a yellow foam (160.61 mg, 29% based on mono-gentisate salt formation).

Summary of Data for Gentisate (Form N) of Compound (I)

| Analysis | Result |
|---|---|
| $^1$H NMR | 1.1 equiv Gentisic acid, 11.8% EtOAc (~0.5 equiv) |
| XRPD | Amorphous |
| mDSC | Tg 29° C. (limits 14 and 42° C.) |

Formation of the desired partially crystalline Gentisate Pattern 1 was not observed, instead formation of an amorphous mono-gentisate salt was observed. In an attempt to crystallise the material samples were matured in a small range of solvent and the results are summarised in the table below.

Example 15

Preparation of Gentisate Salt (Form O) of Compound (I)

The amorphous gentisate salt (Form N) as prepared in example 14 (15 mg) was dissolved in acetonitrile (20 vol) to give a solution at room temperature. The solvent was allowed to evaporate slowly to half the original volume to give crystalline gentisate salt (Form O).

Summary of Data for Gentisate (Form O) of Compound (I)

| Analysis | Result |
| --- | --- |
| $^1$H NMR | 1.0 equiv Gentisic acid, 5.3% MeCN (0.5 equiv) |
| DSC | Endotherm, onset 92.1° C. ($\Delta$H 54 J · g$^{-1}$) |
| TGA | 1.7% wt loss from 85 to 115° C. |

The XRPD peak list and labelled XRPD diffractogram for Gentisate Pattern 2, using Bruker AXS C2 GADDS instrument, can be found below in Table 13 and FIG. 24 respectively.

These results suggest Gentisate Pattern 2 (Form O) material to be a mono Gentisate acid salt containing approximately 0.5 equiv of acetonitrile that is lost in conjunction with an endothermic event. Further analyses to elucidate if the sample is a hemi-solvate or contains trapped solvent were not possible due to the minor amount of material produced.

Example 16

Preparation of Fumarate Salt (Form P) of Compound (I)

Free base compound (I) (400.18 mg, 1.01 mmol, 1 equiv), fumaric acid (116.71 mg, 1.01 mmol, 1 equiv) and EtOAc (4 ml, 10 relative volumes) were charged to a flask and stirred at RT for 16 h. A very thick white suspension was obtained. EtOAc (2 ml) was added and an aliquot was taken. The solid was isolated by vacuum filtration, dried under suction and analysed by XRPD (consistent with Fumarate Pattern 1). The remaining mixture was stirred at RT for a further 3 h. The solid was isolated by vacuum filtration, washed with EtOAc (3×2 ml), dried under suction and in a vacuum oven at 30° C./3 mbar for 15 h to yield the fumarate salt as a yellow solid (261.35 mg, 50% yield based on mono-fumarate salt formation).

Summary of Data for Fumarate (Form P) of Compound (I)

| Analysis | Result |
| --- | --- |
| $^1$H NMR | 1.0 equiv fumaric acid, no residual solvent |
| XRPD | Consistent with Fumarate Pattern 1 |
| DSC | Sharp endotherm 139.5° C. ($\Delta$H 102 J · g$^{-1}$) |
| TGA | 16.3% wt loss from 170 to 250° C. (~0.7 equiv Fumaric acid) |
| HSM | Melt observed with an onset of 135° C. |
| HPLC | 99.1% (largest % imp 0.28 @ 1.1 RRT) |
| AQ Solubility | 54 mg · ml$^{-1}$, pH 4.1 |
| 40° C./75% RH | 7 d - No visual change, XRPD consistent with Fumarate Pattern 1 |
| GVS | Non-hygroscopic, reversible uptake of <0.4 wt % from 0 to 90% RH |

XRPD information on the fumarate salt (Form P) of compound (I) is found in Table 14 and FIG. 25.

Analysis suggested Fumarate Pattern 1 to be a non-solvated mono fumarate salt with a melt at approximately 140° C. The aqueous solubility was determined to be approximately 50 mg. ml$^{-1}$ and was amongst the lowest of the salts obtained during this work. GVS analysis confirmed the material to be non-hygroscopic with less than 0.4 wt % water adsorbed from 0 to 90% RH.

Example 17

Preparation of L-malate Salt (Form Q) of Compound (I)

Free base compound (I) (400.19 mg, 1.01 mmol, 1 equiv), L-malic acid (135.35 mg, 1.01 mmol, 1 equiv) and EtOAc (20 ml, 50 relative volumes) were charged to a flask and stirred at RT for 24 h. Incomplete dissolution of the acid was observed. The mixture was heated to 40° C. and stirred for 1.5 h, then cooled to RT and stirred for a further 14 h. The mixture was cooled to 5° C. for 72 h—no major precipitation was observed. The mixture was cooled to −18° C. for 30 h—some precipitate had formed. The sample was stirred at RT for 1 h to yield a mobile suspension. The solid was isolated by vacuum filtration, washed with EtOAc (2×3 ml), dried under suction and in a vacuum oven at 30° C./3 mbar for 14 h to yield the L-malate salt as a white solid (325.99 mg, 61% yield based on mono-L-malate salt formation).

Summary of Data for L-malate (Form Q) of Compound (I)

| Analysis | Result |
| --- | --- |
| $^1$H NMR | 1.0 equiv malic acid, 0.6% residual EtOAc |
| XRPD | Consistent with L-malate pattern 1 |
| DSC | Endotherm 80.9° C. ($\Delta$H 30 J · g$^{-1}$) |
| TGA | 18.7% wt loss from 150 to 250° C. (~0.7 equiv Malic acid) |
| HSM | Melt observed with an onset of 83° C. |
| HPLC | 98.8% (largest % imp 0.52 @ 1.1 RRT) |
| AQ Solubility | 92 mg · ml$^{-1}$, pH 4.3 |
| 40° C./75% RH | 15 h - Deliquescence<br>7 d - White solid, XRPD showed crystallisation of a new pattern; L-malate Pattern 2 (Form R) |

XRPD information on the L-malate salt (Form Q) of compound (I) is found in Table 15 and FIG. 26.

Analysis suggested L-malate Pattern 1 material to be a non-solvated mono malate salt with a melt at approximately 81° C. L-malate Pattern 1 material appeared to be hygroscopic, as deliquescence occurred within 15 h at 40° C./75% RH. However, upon extended storage at 40° C./75% RH (72 h) crystallisation of a new solid form was observed. XRPD analysis confirmed this material to be inconsistent with L-malate Pattern 1 (Form Q) and was given the identification of L-malate Pattern 2 (Form R).

Example 18

Preparation of L-malate Salt (Form R) of Compound (I)

A sample of L-malate Form Q (75.45 mg) was stored at 40° C./75% RH for 72 h—deliquescence was observed inside 2 h and crystallisation had occurred inside 72 h. The sample was dried in a vacuum oven at 40° C./3 mbar for 18 h to yield the L-malate (Form R) as a white solid. NMR analysis of the sample of Form R formed during the storage of Form Q at 40° C./75% RH confirmed it to be a mono-malate salt. Interestingly, DSC analysis appeared to suggest the material to be non-solvated with a higher melting point (103.5° C.) than L-malate Form Q.

Summary of Data for L-malate (Form R) of Compound (I)

| Analysis | Result |
| --- | --- |
| $^1$H NMR | 1.1 equiv Malic acid, no residual solvent |
| DSC | Endotherm 103.5° C. (81 J·g$^{-1}$) |

Formation of a larger quantity of L-malate Pattern 2 was attempted. A sample of compound (75.45 mg) was stored at 40° C./75% RH for 72 h—deliquescence was observed inside 2 h and crystallisation had occurred inside 72 h. The sample was dried in a vacuum oven at 40° C./3 mbar for 18 h to yield the product as a white solid.

Summary of Data for L-malate (Form R) of Compound (I)—Scale Up

| Analysis | Result |
| --- | --- |
| $^1$H NMR | 1.1 equiv Malic acid, no residual solvent |
| XRPD | Consistent with L-malate Pattern 2 (Form R) |
| DSC | Endotherm 103.6° C. (ΔH 84 J·g$^{-1}$) |
| TGA | 17.5% wt loss from 175 to 255° C. (~0.6 equiv Malic acid) |
| GVS | Reversible uptake of ~2.5 wt % H$_2$O from 0 to 90% RH |

XRPD information on the L-malate salt (Form R) of compound (I) is found in Table 16 and FIG. 27.

These results appear to confirm L-malate Pattern 2 (Form R) to be an anhydrous mono L-malate salt. GVS analysis showed the material to be less hygroscopic than the benzensulfonate and citrate salts.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

XRPD peaks for crystalline free base (Form A) of compound (I)

| Pos. [°2 Th.] | Height [cts] | FWHM [°2 Th.] | d-spacing [Å] | Rel. Int. [%] | Tip width [°2 Th.] |
| --- | --- | --- | --- | --- | --- |
| 7.5313 | 21162.64 | 0.0768 | 11.73852 | 100.00 | 0.0921 |
| 9.6026 | 846.92 | 0.0768 | 9.21066 | 4.00 | 0.0921 |
| 10.2275 | 400.15 | 0.1023 | 8.64925 | 1.89 | 0.1228 |
| 11.2954 | 1863.94 | 0.1023 | 7.83384 | 8.81 | 0.1228 |
| 11.6652 | 300.53 | 0.1023 | 7.58631 | 1.42 | 0.1228 |
| 12.2672 | 3812.02 | 0.1023 | 7.21534 | 18.01 | 0.1228 |
| 12.6242 | 497.83 | 0.1023 | 7.01205 | 2.35 | 0.1228 |
| 13.1780 | 953.85 | 0.1023 | 6.71859 | 4.51 | 0.1228 |
| 14.0653 | 4092.77 | 0.1023 | 6.29672 | 19.34 | 0.1228 |
| 14.8535 | 1458.15 | 0.0768 | 5.96431 | 6.89 | 0.0921 |
| 15.1515 | 343.64 | 0.0768 | 5.84765 | 1.62 | 0.0921 |
| 15.5775 | 2894.50 | 0.1279 | 5.68868 | 13.68 | 0.1535 |
| 16.9914 | 2108.17 | 0.1023 | 5.21838 | 9.96 | 0.1228 |

TABLE 1-continued

XRPD peaks for crystalline free base (Form A) of compound (I)

| Pos. [°2 Th.] | Height [cts] | FWHM [°2 Th.] | d-spacing [Å] | Rel. Int. [%] | Tip width [°2 Th.] |
| --- | --- | --- | --- | --- | --- |
| 17.6862 | 1501.97 | 0.1279 | 5.01490 | 7.10 | 0.1535 |
| 18.3040 | 644.51 | 0.0591 | 4.84701 | 3.05 | 0.0709 |
| 18.3954 | 1212.49 | 0.0768 | 4.82314 | 5.73 | 0.0921 |
| 18.6301 | 1666.18 | 0.1023 | 4.76289 | 7.87 | 0.1228 |
| 18.9784 | 1639.81 | 0.1279 | 4.67626 | 7.75 | 0.1535 |
| 19.3292 | 475.31 | 0.1023 | 4.59219 | 2.25 | 0.1228 |
| 20.2061 | 1067.39 | 0.1023 | 4.39483 | 5.04 | 0.1228 |

TABLE 2

XRPD peaks for L-tartrate salt (Form D) of compound (I)

| Angle 2-Theta ° | Intensity % |
| --- | --- |
| 3.82 | 51.2 |
| 7.57 | 100.0 |
| 8.12 | 14.6 |
| 10.53 | 17.1 |
| 11.39 | 15.0 |
| 12.00 | 15.3 |
| 13.54 | 27.4 |
| 15.15 | 52.6 |
| 16.35 | 20.2 |
| 16.88 | 41.0 |
| 17.37 | 21.7 |
| 18.51 | 24.8 |
| 18.98 | 20.6 |
| 19.77 | 69.9 |
| 21.06 | 31.6 |
| 22.70 | 55.2 |
| 23.47 | 77.1 |
| 24.66 | 43.7 |
| 28.73 | 59.2 |

TABLE 3

XRPD peaks for citrate salt (Form F) of compound (I)

| Angle 2-Theta ° | Intensity % |
| --- | --- |
| 5.14 | 21.4 |
| 7.73 | 17.5 |
| 10.24 | 30.8 |
| 12.70 | 19.8 |
| 13.06 | 23.2 |
| 14.42 | 10.0 |
| 15.30 | 22.7 |
| 15.98 | 11.4 |
| 16.74 | 23.9 |
| 17.24 | 33.1 |
| 18.05 | 42.3 |
| 19.04 | 35.8 |
| 20.23 | 17.0 |
| 21.04 | 22.7 |
| 22.45 | 40.3 |
| 22.75 | 37.9 |
| 24.01 | 82.5 |
| 25.43 | 100.0 |
| 26.51 | 29.7 |
| 27.48 | 24.0 |
| 28.77 | 28.8 |
| 29.71 | 27.0 |

TABLE 4

XRPD peaks for benzenesulfonate salt (Form G) of compound (I)

| Angle 2-Theta ° | Intensity % |
|---|---|
| 5.72 | 17.5 |
| 11.45 | 22.8 |
| 11.79 | 24.3 |
| 15.56 | 100.0 |
| 16.57 | 61.1 |
| 18.04 | 63.9 |
| 19.14 | 52.7 |
| 20.02 | 71.1 |
| 21.05 | 57.5 |
| 22.80 | 85.1 |
| 23.16 | 86.6 |
| 24.44 | 68.9 |
| 25.40 | 49.7 |
| 28.74 | 54.7 |

TABLE 5

XRPD peaks for phosphate salt from ethanol (Form C) of compound (I)

| Angle 2-Theta ° | Intensity % |
|---|---|
| 6.49 | 100.0 |
| 8.91 | 14.7 |
| 9.75 | 16.8 |
| 10.52 | 15.6 |
| 13.03 | 7.1 |
| 15.44 | 11.7 |
| 16.27 | 68.6 |
| 17.85 | 15.5 |
| 18.29 | 20.7 |
| 19.52 | 72.1 |
| 20.02 | 32.5 |
| 21.11 | 20.7 |
| 22.80 | 21.1 |
| 24.92 | 47.1 |
| 28.33 | 18.6 |
| 29.41 | 21.4 |

TABLE 6

XRPD peaks for phosphate salt from IPA (Form B) of compound (I)

| Angle 2-Theta ° | Intensity % |
|---|---|
| 6.46 | 100.0 |
| 8.88 | 15.3 |
| 9.67 | 14.6 |
| 10.47 | 13.3 |
| 12.78 | 9.5 |
| 15.33 | 9.3 |
| 16.12 | 48.1 |
| 16.82 | 9.8 |
| 18.13 | 22.5 |
| 19.38 | 46.8 |
| 19.95 | 19.2 |
| 20.97 | 17.9 |
| 24.11 | 17.4 |
| 24.83 | 28.7 |
| 26.54 | 14.7 |
| 28.11 | 16.8 |

TABLE 7

XRPD peaks for L-tartrate salt (Form E) of compound (I)

| Pos. [° 2 Th.] | Height [cts] | FWHM [° 2 Th.] | d-spacing [Å] | Rel. Int. [%] | Tip width [° 2 Th.] |
|---|---|---|---|---|---|
| 6.6675 | 15483.76 | 0.0768 | 13.25733 | 100.00 | 0.0921 |
| 8.2340 | 241.15 | 0.1023 | 10.73824 | 1.56 | 0.1228 |
| 9.7722 | 479.22 | 0.1023 | 9.05118 | 3.09 | 0.1228 |
| 11.9598 | 926.89 | 0.1023 | 7.40005 | 5.99 | 0.1228 |
| 12.3792 | 494.24 | 0.0768 | 7.15029 | 3.19 | 0.0921 |
| 13.0632 | 4104.92 | 0.0768 | 6.77739 | 26.51 | 0.0921 |
| 13.3777 | 2386.00 | 0.1023 | 6.61876 | 15.41 | 0.1228 |
| 13.9359 | 413.30 | 0.0768 | 6.35490 | 2.67 | 0.0921 |
| 14.9035 | 1349.55 | 0.1023 | 5.94439 | 8.72 | 0.1228 |
| 15.4032 | 975.17 | 0.0768 | 5.75266 | 6.30 | 0.0921 |
| 15.9507 | 949.23 | 0.1023 | 5.55642 | 6.13 | 0.1228 |
| 16.2665 | 488.77 | 0.1023 | 5.44926 | 3.16 | 0.1228 |
| 16.5423 | 792.08 | 0.1023 | 5.35902 | 5.12 | 0.1228 |
| 17.3614 | 2687.54 | 0.1023 | 5.10799 | 17.36 | 0.1228 |
| 17.5690 | 1410.91 | 0.1023 | 5.04809 | 9.11 | 0.1228 |
| 17.8630 | 201.26 | 0.1023 | 4.96566 | 1.30 | 0.1228 |
| 19.6395 | 1756.56 | 0.0768 | 4.52032 | 11.34 | 0.0921 |
| 19.8636 | 777.97 | 0.0768 | 4.46982 | 5.02 | 0.0921 |
| 20.1195 | 549.42 | 0.1023 | 4.41355 | 3.55 | 0.1228 |
| 20.7288 | 1423.91 | 0.1279 | 4.28518 | 9.20 | 0.1535 |
| 21.1373 | 389.18 | 0.1279 | 4.20327 | 2.51 | 0.1535 |
| 21.5804 | 674.89 | 0.1535 | 4.11797 | 4.36 | 0.1842 |
| 22.5683 | 459.02 | 0.1535 | 3.93989 | 2.96 | 0.1842 |
| 22.9541 | 780.05 | 0.1279 | 3.87454 | 5.04 | 0.1535 |
| 23.2869 | 904.34 | 0.1023 | 3.81992 | 5.84 | 0.1228 |
| 23.5693 | 1652.40 | 0.1535 | 3.77478 | 10.67 | 0.1842 |
| 24.0730 | 899.56 | 0.1535 | 3.69692 | 5.81 | 0.1842 |
| 24.6316 | 316.32 | 0.1791 | 3.61434 | 2.04 | 0.2149 |
| 25.2971 | 1357.36 | 0.1535 | 3.52074 | 8.77 | 0.1842 |
| 26.3772 | 346.67 | 0.1023 | 3.37898 | 2.24 | 0.1228 |
| 27.0905 | 141.69 | 0.1023 | 3.29160 | 0.92 | 0.1228 |
| 27.6723 | 474.86 | 0.1023 | 3.22371 | 3.07 | 0.1228 |
| 27.9727 | 708.87 | 0.1535 | 3.18977 | 4.58 | 0.1842 |
| 28.9051 | 262.52 | 0.1535 | 3.08896 | 1.70 | 0.1842 |
| 29.2843 | 136.18 | 0.1535 | 3.04982 | 0.88 | 0.1842 |
| 30.0801 | 73.71 | 0.1535 | 2.97092 | 0.48 | 0.1842 |
| 30.4059 | 137.17 | 0.1279 | 2.93982 | 0.89 | 0.1535 |
| 31.9006 | 27.79 | 0.1535 | 2.80541 | 0.18 | 0.1842 |
| 34.4898 | 70.18 | 0.2047 | 2.60050 | 0.45 | 0.2456 |

TABLE 8

XRPD peaks for Hydrochloride (Form H) of compound (I)

| Angle/2-Theta ° | Intensity/% |
|---|---|
| 5.6 | 100.0 |
| 8.6 | 8.0 |
| 9.5 | 6.2 |
| 10.9 | 10.2 |
| 11.2 | 12.2 |
| 12.7 | 20.5 |
| 13.0 | 8.9 |
| 14.3 | 5.9 |
| 16.0 | 10.9 |
| 17.3 | 8.0 |
| 17.7 | 9.4 |
| 18.8 | 15.9 |
| 19.1 | 9.8 |
| 20.3 | 8.5 |
| 20.7 | 9.4 |
| 22.9 | 8.1 |
| 23.6 | 10.1 |
| 24.5 | 10.7 |
| 25.0 | 8.4 |
| 25.5 | 9.9 |
| 25.8 | 10.2 |
| 26.4 | 8.4 |
| 29.1 | 10.2 |

TABLE 9

XRPD peaks for Hydrochloride (Form I) of compound (I)

| Angle/2-Theta ° | Intensity/% |
|---|---|
| 4.9 | 41.7 |
| 6.4 | 100.0 |
| 7.5 | 65.5 |
| 12.1 | 19.0 |
| 14.4 | 30.3 |
| 19.8 | 25.1 |
| 21.5 | 31.0 |
| 23.4 | 26.2 |
| 25.7 | 28.8 |

TABLE 10

XRPD peaks for Hydrobromide (Form J) of compound (I)

| Angle/2-Theta ° | Intensity/% |
|---|---|
| 6.4 | 100.0 |
| 7.2 | 57.0 |
| 12.0 | 20.5 |
| 14.4 | 38.7 |
| 17.1 | 22.7 |
| 19.6 | 35.3 |
| 21.4 | 37.9 |
| 25.5 | 40.4 |

TABLE 11

XRPD peaks for Mesylate (Form L) of compound (I)

| Angle/2-Theta ° | Intensity/% |
|---|---|
| 6.3 | 100.0 |
| 7.9 | 6.4 |
| 12.5 | 18.6 |
| 13.4 | 3.7 |
| 14.6 | 9.5 |
| 15.9 | 5.4 |
| 16.5 | 26.4 |
| 17.5 | 23.5 |
| 18.1 | 18.6 |
| 18.7 | 4.1 |
| 19.3 | 5.5 |
| 20.0 | 12.9 |
| 20.6 | 10.5 |
| 20.9 | 8.3 |
| 21.7 | 20.2 |
| 22.6 | 18.0 |
| 23.8 | 9.8 |
| 24.5 | 5.6 |
| 25.1 | 10.5 |
| 25.5 | 7.0 |
| 26.1 | 10.4 |
| 27.5 | 5.1 |
| 29.1 | 4.9 |
| 29.7 | 6.3 |
| 30.3 | 4.2 |

TABLE 12

XRPD peaks for Maleate (Form M) of compound (I)

| Angle/2-Theta ° | Intensity/% |
|---|---|
| 3.8 | 21.7 |
| 7.6 | 100.0 |
| 8.5 | 28.0 |
| 10.8 | 5.6 |

TABLE 12-continued

XRPD peaks for Maleate (Form M) of compound (I)

| Angle/2-Theta ° | Intensity/% |
|---|---|
| 11.4 | 8.6 |
| 12.2 | 37.2 |
| 15.2 | 48.5 |
| 15.8 | 11.1 |
| 17.0 | 10.0 |
| 18.0 | 18.1 |
| 18.8 | 13.5 |
| 19.4 | 24.1 |
| 20.3 | 8.9 |
| 21.6 | 6.0 |
| 22.6 | 6.2 |
| 23.6 | 23.2 |
| 24.3 | 22.0 |
| 24.8 | 20.5 |
| 26.0 | 14.7 |
| 27.2 | 10.6 |
| 27.9 | 16.2 |
| 28.2 | 8.6 |
| 28.8 | 4.8 |
| 29.9 | 5.9 |
| 30.2 | 5.0 |
| 31.7 | 5.1 |
| 32.7 | 4.2 |
| 33.2 | 4.7 |

TABLE 13

XRPD peaks for Gentisate (Form O) of compound (I)

| Angle/2-Theta ° | Intensity/% |
|---|---|
| 6.318 | 20.5 |
| 12.161 | 21.3 |
| 12.449 | 19.6 |
| 13.13 | 59.5 |
| 14.414 | 21.2 |
| 14.831 | 18.5 |
| 16.369 | 17.2 |
| 17.122 | 18.1 |
| 18.787 | 25.7 |
| 19.485 | 19 |
| 20.419 | 17.2 |
| 23.371 | 100 |
| 23.769 | 54.1 |

TABLE 14

XRPD peaks for Fumarate (Form P) of compound (I)

| Angle/2-Theta ° | Intensity/% |
|---|---|
| 3.8 | 14.1 |
| 7.7 | 100.0 |
| 8.1 | 14.6 |
| 8.8 | 44.6 |
| 10.2 | 11.2 |
| 11.3 | 9.9 |
| 13.1 | 45.4 |
| 15.2 | 28.7 |
| 15.5 | 16.7 |
| 16.5 | 27.1 |
| 17.7 | 60.0 |
| 19.1 | 13.7 |
| 19.6 | 10.9 |
| 20.0 | 6.0 |
| 20.9 | 5.0 |
| 21.5 | 5.4 |
| 21.9 | 11.2 |
| 22.7 | 9.9 |

TABLE 14-continued

XRPD peaks for Fumarate (Form P) of compound (I)

| Angle/2-Theta ° | Intensity/% |
| --- | --- |
| 23.3 | 28.6 |
| 23.8 | 25.4 |
| 24.1 | 18.3 |
| 25.0 | 20.0 |
| 25.3 | 9.6 |
| 26.7 | 17.7 |
| 27.9 | 8.8 |
| 28.9 | 8.9 |

TABLE 15

XRPD peaks for L-malate (Form Q) of compound (I)

| Angle/2-Theta ° | Intensity/% |
| --- | --- |
| 6.7 | 39.7 |
| 8.6 | 60.0 |
| 9.3 | 44.4 |
| 11.0 | 19.7 |
| 12.7 | 100.0 |
| 13.6 | 41.4 |
| 14.1 | 37.1 |
| 15.1 | 47.5 |
| 15.8 | 27.5 |
| 16.5 | 26.9 |
| 17.8 | 38.2 |
| 18.7 | 56.4 |
| 19.5 | 41.9 |
| 19.8 | 43.9 |
| 21.2 | 28.2 |
| 22.5 | 33.2 |
| 23.5 | 29.4 |
| 24.9 | 37.3 |
| 25.7 | 42.3 |

TABLE 16

XRPD peaks for L-malate (Form R) of compound (I)

| Angle/2-Theta ° | Intensity/% |
| --- | --- |
| 6.773 | 100 |
| 9.851 | 10.7 |
| 12.191 | 6.9 |
| 13.364 | 39.3 |
| 13.587 | 37.3 |
| 14.145 | 6.3 |
| 15.883 | 17.5 |
| 16.44 | 22.9 |
| 17.331 | 22.2 |
| 17.753 | 17.8 |
| 19.733 | 27.6 |
| 20.118 | 13.4 |
| 20.496 | 29.8 |
| 20.837 | 15.7 |
| 21.299 | 12.4 |
| 22.231 | 29.3 |
| 23.273 | 28.7 |
| 23.828 | 11.5 |
| 24.19 | 15 |
| 24.606 | 11.8 |
| 25.182 | 14.7 |
| 25.673 | 13.6 |
| 26.026 | 23.3 |
| 26.31 | 13.9 |
| 26.905 | 10.2 |
| 27.779 | 9.9 |
| 28.775 | 17.9 |
| 31.109 | 8.9 |
| 32.352 | 7 |
| 33.239 | 9.3 |

TABLE 17

XRPD peaks for bromide (Form K) of compound (I)

| Angle/2-Theta ° | Intensity/% |
| --- | --- |
| 5.732 | 100 |
| 16.386 | 32.1 |
| 17.675 | 31.8 |
| 18.369 | 46.3 |
| 19.633 | 45.9 |
| 20.542 | 59 |
| 24.136 | 85.3 |
| 25.272 | 59.5 |
| 25.976 | 46.4 |
| 28.119 | 45.2 |

The invention claimed is:

1. A crystalline form of compound (I),

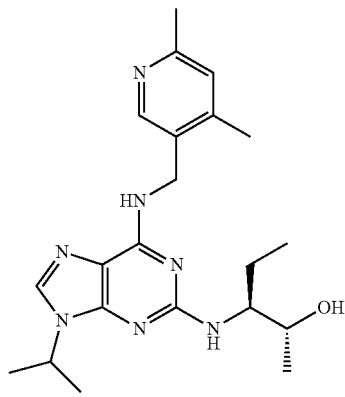

(I)

which is an L-tartrate salt; and which is characterized by an x-ray powder diffraction pattern having two or more diffraction peaks at 2[theta] values selected from 6.67 ±0.2, 8.237±0.2, 9.777 ±0.2, 11.96 ±0.2, 12.38 ±0.2, 13.06 ±0.2, 13.38 ±0.2, 13.94 ±0.2, 14.90 ±0.2, 15.40 ±0.2, 15.95 ±0.2, 16.27 ±0.2, 16.54 ±0.2, 17.36 ±0.2, 17.57 ±0.2, 17.86 ±0.2, 19.64 ±0.2, 19.86 ±0.2, 20.12 ±0.2, 20.73 ±0.2, 21.14 ±0.2, 21.58 ±0.2, 22.57 ±0.2, 22.95 ±0.2, 23.29 ±0.2, 23.57 ±0.2, 24.07 ±0.2, 24.63 ±0.2, 25.30 ±0.2, 26.38 ±0.2, 27.09 ±0.2, 27.67 ±0.2, 27.97 ±0.2, 28.91 ±0.2, 29.28 ±0.2, 30.08 ±0.2, 30.41 ±0.2, 31.90 ±0.2 and 34.49 ±0.2 (Form E).

Figure 1:
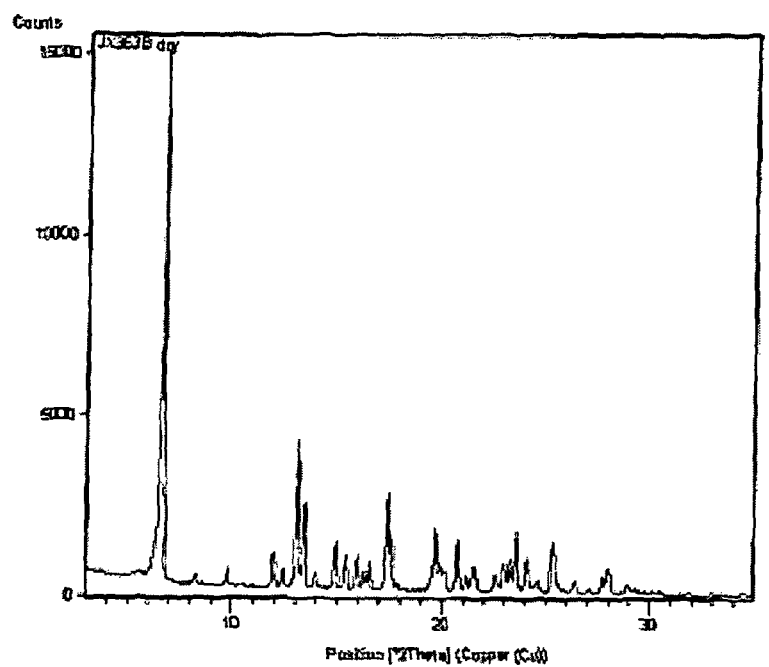
FIG. 1 shows the X-ray powder diffraction pattern of Form E of the L-tartrate salt of compound (I), as obtained by Example 5.2. The diffraction pattern was obtained by irradiation of the crystalline product using a PANalytical diffractometer.
Figure 2:
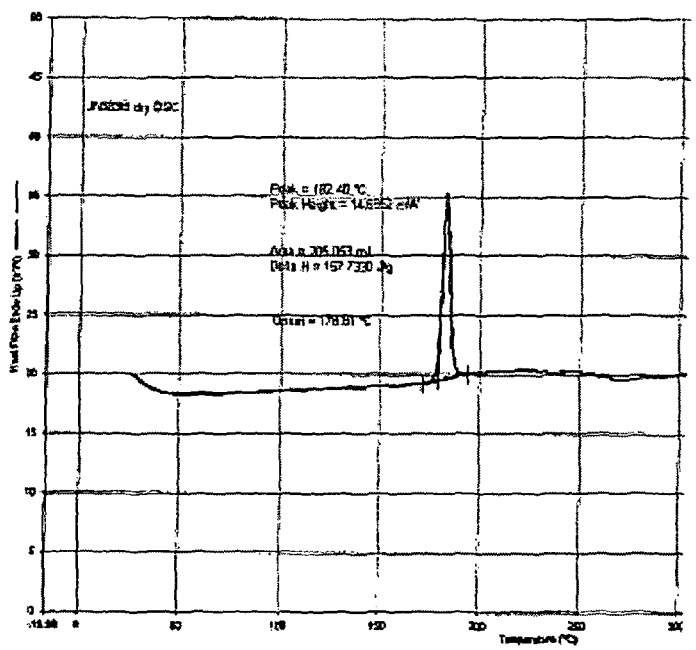
FIG. 2 is a DSC thermogram of Form E of the L-tartrate salt of compound (I) obtained using a PerkinElmer DSC4000 at a heating rate of 20° C. min$^{-1}$. Peak max is observed at 182.40° C.
Figure 3:
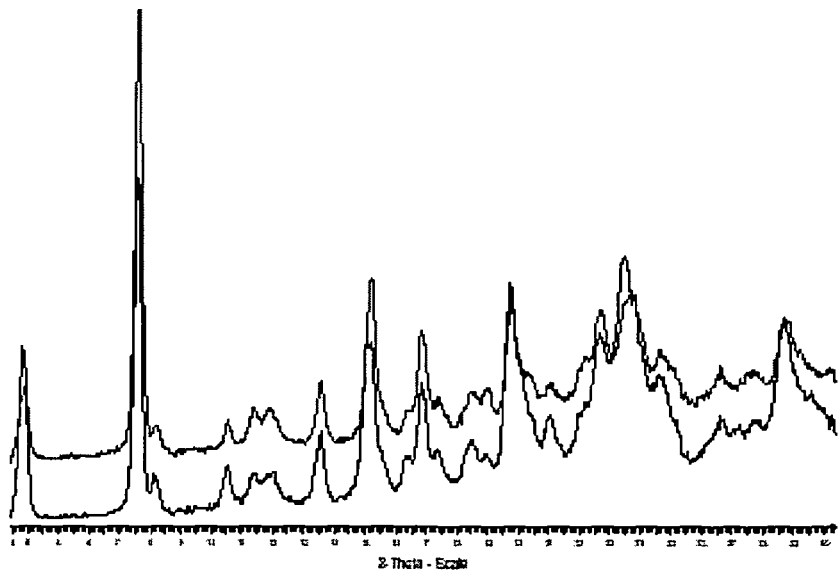
FIG. 3 shows the X-ray powder diffraction pattern of Form D of the L-tartrate salt of compound (I) as obtained by Example 4. The diffraction pattern was obtained by irradiation of the crystalline product using Bruker AXS C2 GADDS.

2. The crystalline form of claim 1 which is further characterized by a differential scanning calorimetry trace recorded at a heating rate of 20° C. per minute which shows a maximum endothermic peak at a temperature between about 176° C. and about 185° C., or a differential scanning calorimetry trace substantially in accordance with that shown in FIG. 2.

3. A crystalline form of compound (I),

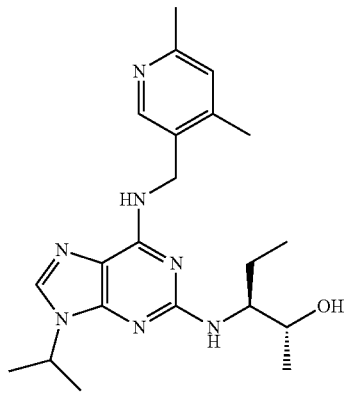

(I)

which is an L-tartrate salt; and which is characterized by an x-ray powder diffraction pattern having two or more diffraction peaks at 2[theta] values selected from 3.82 ±0.2, 7.57 ±0.2, 8.12 ±0.2, 10.53 ±0.2, 11.39 ±0.2, 12.00 ±0.2, 13.54 ±0.2, 15.15 ±0.2, 16.35 ±0.2, 16.88 ±0.2, 17.37 ±0.2, 18.51 ±0.2, 18.98 ±0.2, 19.77±0.2, 21.06 ±0.2, 22.70 ±0.2, 23.47 ±0.2, 24.66 ±0.2 and 28.73 ±0.2 [Form D].

Figure 4:
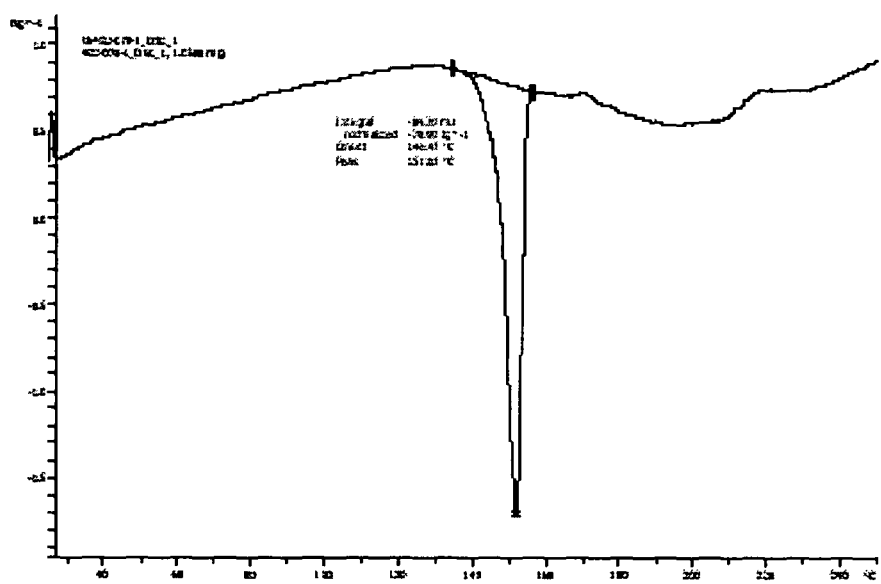
FIG. 4 is a DSC thermogram of Form D of the L-tartrate salt of compound (I) as obtained by Example 4, using Mettler DSC823e at a heating rate of 20° C. min$^{-1}$. Peak max is observed at 151.83° C.

4. The crystalline form of claim 3 which is further characterized by a differential scanning calorimetry trace recorded at a heating rate of 10° C. per minute which shows a maximum endothermic peak at a temperature between about 145° C. and about 154° C., or a differential scanning calorimetry trace substantially in accordance with that shown in FIG. 4.

* * * * *